US012802218B2

(12) United States Patent
Van Der Zaag et al.

(10) Patent No.: US 12,802,218 B2
(45) Date of Patent: Nov. 17, 2026

(54) METHOD AND DEVICE OF INSPECTING A FLUORESCENCE IMAGE OF A MAMMAL TISSUE

(71) Applicants: Rijksuniversiteit Groningen, Groningen (NL); Academisch Ziekenhuis Groningen, Groningen (NL)

(72) Inventors: Pieter Jan Van Der Zaag, Waalre (NL); Leander Marten Van Boven, Groningen (NL); Jesper Siemen Kuiper, Groningen (NL); Bas Keizers, Groningen (NL); Thomas Sebastiaan Nijboer, Groningen (NL); Floris Jan Voskuil, Groningen (NL)

(73) Assignees: RIJKSUNIVERSITEIT GRONINGEN, Groningen (NL); ACADEMISCH ZIEKENHUIS GRONINGEN, Groningen (NL)

( * ) Notice: Subject to any disclaimer, the term of this patent is extended or adjusted under 35 U.S.C. 154(b) by 213 days.

(21) Appl. No.: 18/780,009

(22) Filed: Jul. 22, 2024

(65) Prior Publication Data

US 2024/0412362 A1 Dec. 12, 2024

Related U.S. Application Data

(63) Continuation-in-part of application No. PCT/NL2024/050114, filed on Mar. 8, 2024.

(30) Foreign Application Priority Data

Mar. 8, 2023 (NL) ..................................... 2034294

(51) Int. Cl.

| | |
|---|---|
| ***G06T 7/00*** | (2017.01) |
| ***G01N 21/64*** | (2006.01) |

(Continued)

(52) U.S. Cl.

CPC ....... *G06T 7/0012* (2013.01); *G01N 21/6428* (2013.01); *G01N 21/6456* (2013.01);

(Continued)

(58) Field of Classification Search

CPC ......... A61B 1/043; G06T 7/0012; G06T 7/13; G06T 7/70; G06T 7/194; G06T 5/20;

(Continued)

(56) References Cited

U.S. PATENT DOCUMENTS

| | | | |
|---|---|---|---|
| 4,972,262 | A | 11/1990 | Nichols |
| 2005/0094147 | A1 | 5/2005 | Yaroslavsky et al. |

FOREIGN PATENT DOCUMENTS

| | | | |
|---|---|---|---|
| EP | 2074933 A1 * | 7/2009 | .............. G06T 7/13 |

OTHER PUBLICATIONS

Hefti, et al. (Computer English Translation of European Pat. No. EP2074933 A1). (Year: 2009).*

(Continued)

*Primary Examiner* — Daniel G Mariam

(74) *Attorney, Agent, or Firm* — Harness, Dickey & Pierce, P.L.C.

(57) ABSTRACT

An inspection method is disclosed to inspect a fluorescent image of a mammal tissue that comprises an array of pixels having respective fluorescent signal values. A reference value is determined, such that a second number of fluorescent signal values, as a predetermined fraction of a first number of fluorescent signal values, is smaller than or equal to the reference value and the remainder of the first number of fluorescent signal values exceeds the reference value. The method comprises, in the second number of fluorescent signal values, determining an average fluorescent signal value and a standard deviation of those fluorescent signal values. An image segmentation is performed to distinguish in the fluorescent image a target region to denote a portion (Continued)

in the mammal tissue that is identified as tumorous tissue and a reference region to denote a remaining portion in the mammal tissue.

16 Claims, 53 Drawing Sheets

(51) Int. Cl.

| | |
|---|---|
| ***G01N 33/483*** | (2006.01) |
| ***G06T 5/20*** | (2006.01) |
| ***G06T 5/70*** | (2024.01) |
| ***G06T 7/13*** | (2017.01) |
| ***G06T 7/194*** | (2017.01) |
| ***G06T 7/70*** | (2017.01) |

(52) U.S. Cl.
CPC .......... *G01N 33/4833* (2013.01); *G06T 5/20* (2013.01); *G06T 5/70* (2024.01); *G06T 7/13* (2017.01); *G06T 7/194* (2017.01); *G06T 7/70* (2017.01); *G01N 2021/6439* (2013.01); *G06T 2207/10064* (2013.01); *G06T 2207/30024* (2013.01); *G06T 2207/30096* (2013.01); *G06T 2207/30168* (2013.01)

(58) Field of Classification Search
CPC . G06T 2207/10064; G06T 2207/30024; G06T 2207/30096; G06T 2207/30168; G01N 21/6428; G01N 21/6456; G01N 33/4833; G01N 2021/6439
See application file for complete search history.

(56) References Cited

OTHER PUBLICATIONS

Haidi et al., Computers in biology and medicine, 85 (2017) 75-85, XP085046083.
Anonymous, “Otsu’s method—Wikipedia”, (2017), XP055468978.
Li L et al Academic radiology vol. 8 No. 7 (2001) 629-638, XP027112680.
Suhail M Odeh et al Analysis and recognition lecture notes in computer science (2006) 648-659, XP019043823.

* cited by examiner

α = 0

α = 45

α = 90

FIG. 27A
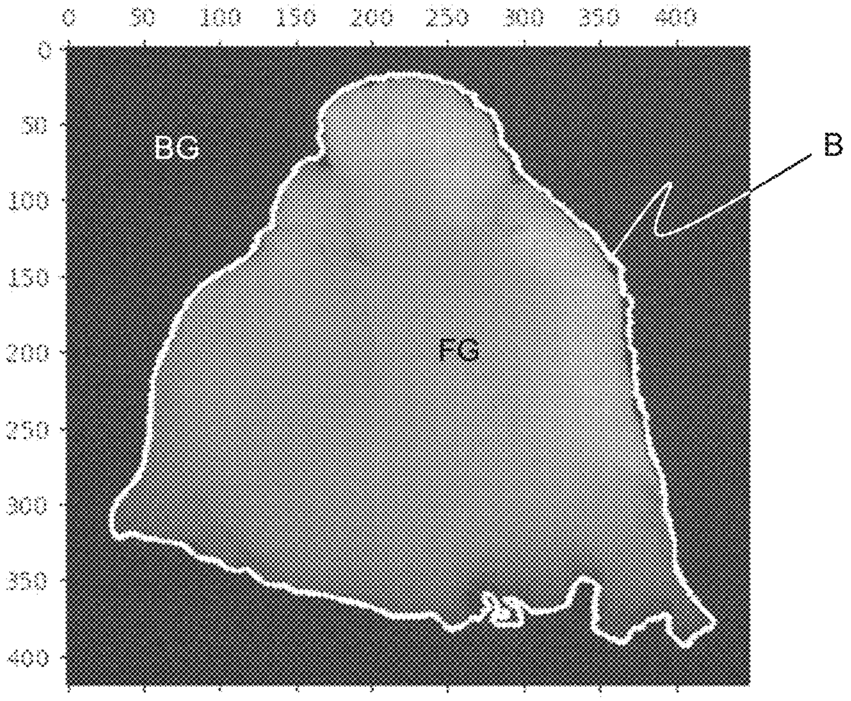
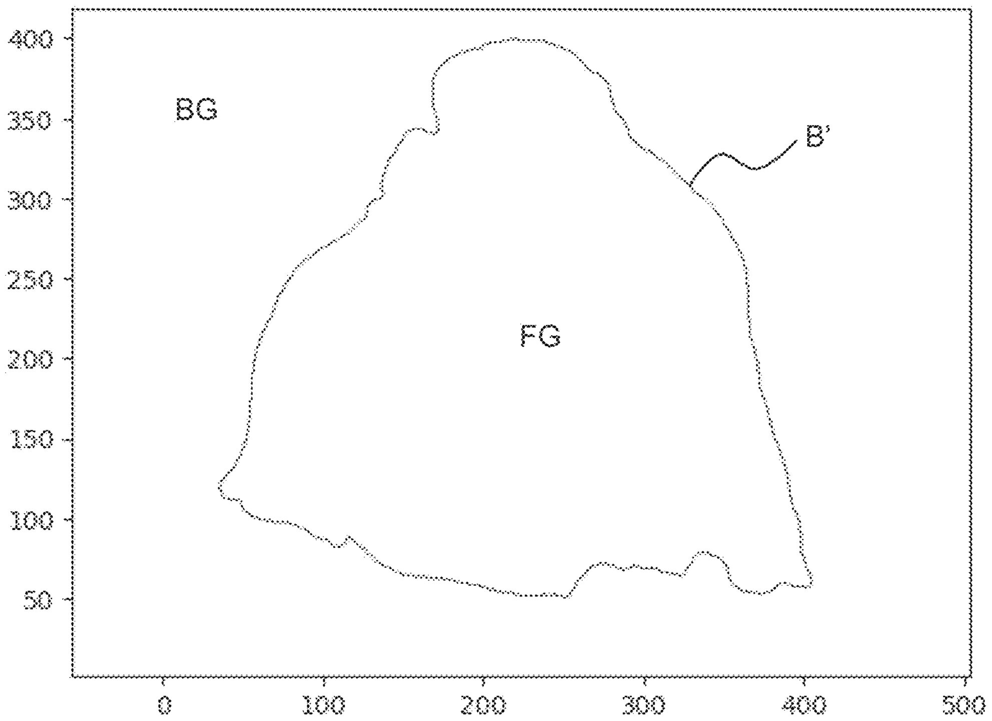
FIG. 27B

METHOD AND DEVICE OF INSPECTING A FLUORESCENCE IMAGE OF A MAMMAL TISSUE

CROSS-REFERENCE TO RELATED APPLICATIONS

This application is a continuation-in-part of International Application PCT/NL2024/050114, filed Mar. 8, 2024, which claims the benefit of priority to Application EP 23154545.0, filed Feb. 1, 2023, and to Application NL 2034294, filed Mar. 8, 2023. Benefit of the filing date of these prior applications is hereby claimed. Each of these prior applications is hereby incorporated by reference in its entirety.

BACKGROUND

The present application pertains to an image inspection method.

The present application pertains to an image inspection device.

Treatment for most types of solid cancers consists of a radical surgical resection of all tumor tissue. However, differentiation between normal and tumor tissue intraoperatively remains difficult. Therefore, it is not uncommon that a tumor-positive margin is found during pathology assessment two to five days after surgery. According to literature, rates of tumor-positive margins (TPM) range from 10 to 35 percent depending on tumor type. See e.g. Orosco, R. K. et al. Positive surgical margins in the 10 most common solid cancers. Sci. Rep. 8, 56-86 (2018). https://doi.org/10.1038/s41598-018-23403-5. If tumor tissue is present at, or near, the rim of the resected tissue, the risk of local recurrence and distant metastasis is increased which implies a decrease in survival. Consequently, a TPM necessitates additional treatment such as re-operation, radiation therapy and/or systemic therapy. Unfortunately, this is associated with increased morbidity and higher psychological burden to the patient. Therefore, it is crucial to be able to correctly visualize tumor tissue during surgery, however, current optical techniques as well as visual and tactile information obtained by the practitioner are not sufficient to determine tumor margins adequately. Therefore, new techniques in which real-time tumor visualization is obtained are investigated, aiming to reduce the number of TPMs and thereby decrease additional treatments and morbidity.

One of the imaging techniques gaining interest is fluorescence molecular imaging (FMI) because of the possibility for real-time tumor visualization deployed both in the patient (i.e. in-vivo) and immediately after excision (ex-vivo). Therewith the tissue to be inspected is prepared with a fluorescent agent, either by administering the fluorescent agent (FA) to the patient or by impregnating the tissue therewith. The fluorescent agent (FA) may be an untargeted fluorescent dye such as Indocyanine green (ICG), or a targeted fluorescent dyes for imaging tumor tissue and infection and track medicinal therapy. Even though research into FMI in the near-infrared (NIR) spectral range (700-900 nm) has showed promising results, it has been found that there are still complications. For example, scattering of light and absorbance by biological components such as water and blood contribute to attenuation of the excitation light, therewith causing a decrease in sensitivity and contrast of the fluorescence images. These factors may contribute to false-positive TPMs on fluorescence images, even though no TPM is present in the patient. Therewith the obtained fluorescence image (FI) is not always directly suitable as a guidance for the surgeon or other medical specialist or for use with a medical treatment device.

W. Heeman et al., A Guideline for Clinicians Performing Clinical Studies with Fluorescence Imaging, J. Nucl. Med., 63 (2022) 640 describe a method wherein a CNR ratio is determined for a tissue sample after it has been inspected by a pathologist. The CNR therein is the contrast-to-noise ratio computed for the target region as a whole determined by the pathologist.

SUMMARY

According to a first object, an improved inspection method is provided for inspecting a fluorescence image of a mammal tissue so as to facilitate a specialist or a surgery device to perform a therapy.

According to a second object, an improved inspection device is provided for inspecting a fluorescence image of a mammal tissue so as to facilitate a specialist or a surgery device to perform a therapy.

According to the present disclosure a border between the target region, e.g. representing a lesion or a tumour, is identified on the basis of pixels at which the excess contrast-to-noise ratio is larger than what may be expected on the basis of global image aspects of the statistical variations represented by the standard deviation of a luminescence signal value (pixel-value) in the reference region and the luminescence signal value relative the average background signal level. In practice, the luminescence may be bioluminescence based on biological processes generating ultraviolet, optical light or infrared emission from the lesion. In general, the principal chemical reaction in bioluminescence involves a light-emitting molecule and an enzyme. Also, good results are achieved on the basis of fluorescence in which in response to an optical excitation fluorescence emission is generated at a longer wavelength.

For example, in a preliminary steps the mammal tissue, e.g. a human tissue, is irradiated with excitation light, after it is rendered photosensitive with a fluorescent agent, and the fluorescence image is captured from the irradiated and photosensitive tissue. The fluorescent agent serves to visualize different types of tissue such as tumor tissue and tumor free tissue. In one example the fluorescent agent is a targeted fluorescent tracer such as Cetuximab-IRDye800CW or hexvix for imaging tumor tissue and/or infection and track medicinal therapy. In another example, the fluorescent agent is an untargeted fluorescent dye such as Indocyanine green (ICG) for imaging tissue perfusion. The excitation light with which the tissue is to be irradiated, in-vivo or ex-vivo is typically in the infra-red range. A fluorescent agent can be administered to the patient or may be used to impregnate the tissue.

According to the invention, the excess contrast-to-noise ratio is represented by a preset threshold value for the excess contrast to which a modified contrast-to-noise ratio is compared. The modified contrast-to-noise ratio is a ratio that is in fact an amended form of the usual contrast-to-noise ratio and formed from the fluorescence signal value compared to the average background signal level and relative to the variation level represented by the standard deviation which represents the noise over the reference region. In other words an insight of the present disclosure is that the excess contrast-to-noise ratio that represents additional local contrast-to-noise ratio over the global contrast-to-noise ration that is associated with global contrast aspects in the reference region may characterise the border between the target and reference region, e.g. the border of the tumour. That is, where the contrast-to-noise form (in a modified form) is markedly higher than what is to be statistically expected from the standard deviation and the average over the fluorescence signal values over the reference region, there is a high likelihood of being due to a border between reference and target regions.

The excess contrast-to-noise ratio may be represented in alternative mathematical expressions. The adjustable regularisation parameter may be employed in these various alternatives as a scale factor to the standard deviation and effects a weighting of the noise variations that are inherent to the fluorescence signal level's stochastic random variations that are not associated with image structure, like a border. The preset threshold value for the excess contrast-to-noise ratio effects to avoid erroneous identification of border pixels due to occurrence of an inherent signal variation. Appropriate values of the regularisation parameter and the preset threshold may be obtained by calibration from data sets for which a gold standard determination of the border is available e.g. from pathology analysis. Particularly favourable results for the border are obtained when the regularisation parameter c is set to c=2 and the excess contrast-to-noise threshold $CNR_{th}=1$. Experimental results achieve accurate identification of the border for different tumour types that have the basis tissue type in common in which they occur.

A particular simple implementation for the excess contrast-to-noise ratio is given by the mathematical formula $$mCNR_L(p) = \frac{F_L(p) - F_B - cS}{cS}, \tag{1a}$$

Therein $mCNR_L$ is the excess contrast-to-noise ratio at pixel position p along a scan trajectory L, $F_L(p)$ is the fluorescence level at pixel-position p, $F_B$ is a background fluorescence level associated with the scan trajectory L, S is the standard deviation of the fluorescence levels along the scan trajectory and c is a scalar regularisation parameter that may be set by the user. For the threshold $CNR_{th}=1$ and the regularization parameter c=2 the fluorescence level exceeds the background by at least twice the noise level at the border.

However, variations are possible depending on further requirements. For example, if it is required that a safety margin is taken into account when determining the target region, a predetermined threshold value less than 1 and/or a regularization parameter value less than 2 may be chosen. In that case the estimated target region (TR) will be larger, so that it not only indicates a portion in the mammal tissue (MT) that is identified as tumorous tissue but also a portion of the mammal tissue surrounding the portion indicated as tumorous tissue that has a risk of becoming tumorous tissue.

An alternative excess contrast-to-noise ratio may be defined by the mathematical formula $$\tilde{m}CNR(p) = \frac{F_I(p) - \mu_R}{c\sigma_R}. \tag{1b}$$

Therein $\tilde{m}$CNR is a slightly different excess contrast-to-noise ratio, where $F_I(p)$ is the fluorescence intensity at pixel position and $\mu_R$ is an average fluorescence signal of an estimate of the pixel value in the background region. This background region is determined from some form of histogram analysis of the statistical distribution on the pixel-values in the fluorescence image as a whole (i.e. comprising background and target regions of healthy and tumour tissue, respectively). For example, the background region may be determined as a region with (i) intensities that are less than a reference value and (ii) there are fewer of these values than values exceeding the reference value. Fewer may be defined as a fraction (0<f<1) of the number of intensity values larger than the reference Further $\sigma_R$ is the standard deviation of the pixel's values in the target region. Notably this defines the invention independently of the use of scan trajectories to sample the pixel values.

In one example a histogram is obtained of the fluorescence signal values comprised in the first number of fluorescence signal values and the reference value is the value for a predetermined k-th q-quantile of the histogram. The predetermined k-th q-quantile should be chosen in accordance with an expected tumorous tissue area ratio re of a tumorous tissue area to the total tissue area in the fluorescence image (FI). The ratio k/q should not exceed that tumorous tissue area ratio. Also the ratio k/q should not be too small. For example $$0.1 * r_e \leq \frac{k}{q} \leq 0.95 * r_e \tag{2}$$

The improved method is used for example for ex-vivo inspection of mammal tissue which has been resected by a medical specialist to remove tumorous tissue. Typically the mammal tissue removed by the medical specialist also includes a substantial portion of normal tissue to take into account that the tissue that is readily identified as tumorous is surrounded by tissue that at first sight looks normal, but could later develop also into tumorous tissue. Also it may be practically impossible to exactly follow the border of the tumorous tissue when performing a resection.

Accordingly, in these cases the ratio k/q is often selected as:

$$0.5 \leq \frac{k}{q} \leq 0.9 \tag{2a}$$

An average fluorescence signal value $F_B$ and a standard deviation S is computed of the fluorescence signal values comprised in the second number of fluorescence signal values. Due to the fact that the ratio k/q is selected not too small, i.e. at least $0.1*r_e$, and preferably 0.2 a sufficient amount of data is available to reliably estimate the average fluorescence signal value and the standard deviation of the fluorescence signal for normal tissue. Due to the fact that the ratio k/q is selected not too large, i.e. at most $0.95*r_e$, and preferably 0.9 it is avoided that the estimation of this statistical data is affected by fluorescence signal data of tumorous tissue.

Yet a further alternative mathematical expression for an excess contrast-to-noise ratio is $$\hat{m}CNR(p) = \frac{\left(\sqrt[\alpha]{\left||F_I(p)|^\alpha - |\mu_R|^\alpha\right|}\right)}{c\sigma_R} \tag{1c}$$

Here the adjustable parameter a operates to emphasize differences at low fluoresces signal levels relative to differences at higher fluorescence levels (and vice versa).

It has appeared that in practice similar results for the identified border may be obtained for suitable settings of the threshold value, regularisation, and emphasis parameters. The emphasis parameter may be set according to the distribution of signal differences in the image to be processed and the regularisation parameter and the contrast-to-noise threshold for identification of the border may be calibrated on the basis of pathology information.

A further alternative approach is given by a variation of equation (1a):

$$mCNR_L(p) = \frac{\sqrt[\alpha]{|F_L(p)|^\alpha - |F_B - cS|^\alpha}}{cS} \tag{1d}$$

The excess contrast-to-noise ratio that represents additional local contrast-to-noise ratio over the global contrast-to-noise ratio that is associated with global contrast aspects in the reference region may or may not include the specific simple examples of equations (1a) and (1b).

In most embodiments of the invention, an optical (including infrared) arrangement is provided to detect the luminescent, in particular fluorescence signal in a spatially resolved way, e.g. in the form of an image of the luminescent or fluorescent tissue to be inspected. A simple camera with a single lens or even a pinhole camera may be employed. Alternatively, a more sophisticated optical arrangement with a multiple-lens assembly, such as known per se from the field of endoscopy may be employed.

Further, the optical arrangement may be provided with an electrical power supply e.g. based on (re-chargeable) batteries or based on an appropriate power conversion from main power.

As noted the improved image inspection methods as disclosed herein are particular suitable for inspecting a fluorescence image captured of a mammal tissue that has been rendered photosensitive with a fluorescent agent and irradiated with excitation light. In this application, the fluorescence signal values of the fluorescence image (FI) represent the mammal tissue. The method may further comprise a step of performing an image segmentation to distinguish in the fluorescence image (FI) a target region (TR) to denote a portion in the mammal tissue (MT) that is identified as tumorous tissue or infected tissue and a reference region (RR) to denote a remaining portion in the mammal tissue (MT). This step comprises determining per pixel (p) that it is part of the target region (TR) if an excess contrast-to-noise ratio mCNR (p) for said pixel exceeds a predetermined threshold value ($T_{CNR}$) and determining that the pixel is part of the reference region (RR) otherwise, wherein the excess contrast-to-noise ratio mCNR (p) of a pixel is defined as $$\hat{m}CNR(p) = \frac{FI(p) - \mu_R}{c \cdot \sigma_R} \tag{1b}$$

wherein FI(p) is the fluorescence signal value of the pixel (p) and c is a regularization parameter.

The method may further comprise identifying at least one contour (B) of the target region (TR).

In this application the fluorescence image (FI) may further capture a background. Then a preliminary image segmentation may be performed on the fluorescence image to distinguish in the fluorescence image (FI) a foreground region (FR) representing the mammal tissue (MT) and a background region (BR) representing the background. The segmentation step may comprise determining per pixel that it is part of the foreground region (FR) if the fluorescence signal value (FSV) significantly exceeds an average fluorescence signal value determined for the background taking into account a standard deviation of fluorescence signal values (FSV) in the background and determining that the pixel is part of the background region (BR) otherwise. In an example the average fluorescence signal value and the standard deviation of fluorescence signal values are determined from a portion (BP) of the fluorescence image (FI) that is designated as representing the background. In an example the preliminary image segmentation further comprises a dilation operation. Therein the foreground region is extended with one or more pixels to mitigate a risk of edge-effects. Also other corrections may be applied, such as removal of regions identified in the preliminary image segmentation that have an area smaller than a threshold area value. For example isolated small areas that initially are identified as foreground or that initially are identified as background. Typically the largest initially identified foreground area is selected for further processing and any smaller initially identified foreground area are considered as part of the background.

In case a preliminary image segmentation is applied then the subsequent image segmentation to determine one or more target regions are applied to the portion of the image determined as foreground region.

In some examples the fluorescence image of the mammal tissue is captured in-vivo. In other examples the fluorescence image of the mammal tissue is captured ex-vivo with the mammal tissue arranged on the background.

In one example the background is formed by a carrier surface on which a mammal tissue (for example a complete resected tissue or a slice thereof) is arranged for ex-vivo inspection. In another example the fluorescence image is captured in-vivo while a background is placed in the field of view of the camera as a reference. In the preliminary image segmentation it is determined per pixel whether or not its fluorescence signal value (FSV) significantly exceeds an average background fluorescence signal value. If it is determined that a fluorescence signal value (FSV) of a pixel significantly exceeds the average background fluorescence signal value then that pixel is classified as part of the foreground region otherwise it is determined as part of the background region. As an example it is determined that a fluorescence signal value (FSV) of a pixel significantly exceeds the average background fluorescence signal value if a difference between its fluorescence signal value (FSV) and the background fluorescence signal value exceeds a predetermined factor times the standard deviation of the fluorescence signal values of the background. The predetermined factor is for example greater than 1, e.g. in a range from 1.05 to −5, for example about 2.

In one example the average fluorescence signal value and the standard deviation are estimated in a calibration step, wherein prior to capturing the fluorescence image a calibration fluorescence image is captured of the background only and the average fluorescence signal value and the standard deviation are determined are determined of the fluorescence signal values in the calibration fluorescence image.

A rough but useful estimation of the average fluorescence signal value can obtained as follows:

$$\mu_{est} = \frac{\min + \max}{2} \tag{3a}$$

-continued $$\sigma_{est} = \frac{\max - \min}{2\sqrt{3}} \quad (3b)$$

Therein min, max respectively are the minimum fluorescence value and the maximum fluorescence value of all fluorescence values in the fluorescence image.

In another example the average fluorescence signal value and the standard deviation of fluorescence signal values are determined from a portion (BP) of the fluorescence image (FI) that is designated as representing the background. An operator may for example a rectangular region in the fluorescence image (FI) that is part of the background represented in the fluorescence image (FI). Based on the average fluorescence signal value and the standard deviation of fluorescence signal values in this region a complete preliminary image segmentation can then be performed.

In an example the inspection method further comprises a scan trajectory based evaluation that includes obtaining at least one fluorescence signal value vector of fluorescence signal values in the fluorescence image (FI) along a scan trajectory. Then for each threshold value of a plurality of threshold values a respective set of candidate scan trajectory sections is determined in which the fluorescence signal value exceeds the threshold value and statistical properties of sections of the scan trajectory are determined that are not candidate scan trajectory sections. Subsequently it is determined for which threshold value of the plurality of threshold values the respective set of candidate scan trajectory sections best matches the image segmentation of the fluorescence image (FI) along the scan trajectory according to an excess contrast-to-noise ratio based segmentation using the determined statistical properties.

In an example the improved method further comprises determining at least one main axis for at least one contour. Subsequently at least one fluorescence signal value vector of fluorescence signal values in the fluorescence image (FI) along a scan line is obtained that is orthogonal to the main axis. Based on information of the contour at points of intersection with the scan line, one or more sections of the scan line are identified where an excess contrast-to-noise ratio exceeds a predetermined level. These scan line sections each comprise a respective first end point indicative for a transition (NT) from normal tissue to tumorous tissue or infected tissue and a respective second end point indicative for a transition (TN) from tumorous tissue or infected tissue to normal tissue.

The present disclosure further provides a further image inspecting method to inspect a luminescence image, in particular a fluorescence image, represented as an array of pixels, $N_I$ in number, and having respective fluorescence signal values ($F_I$(p)). The further image method comprising a procedure for indicating in the fluorescence image a border between a target region representing a tumour and a reference region outside the target region. The further image inspection method obtains at least one sequence of respective logarithmic fluorescence signal values of respective subsequent pixels that are arranged along a scan trajectory within the fluorescence image, wherein the scan trajectory starts in a position identified as being part of the reference region in the fluorescence image. The method subsequently computes an indicator for a local linearity of the logarithmic fluorescence signal value as a function of the position in the at least one sequence. The method then identifies a position in the sequence wherein the indicator indicates that the logarithmic fluorescence signal value as a function of the position in the sequence is no longer linear, the identified position being a candidate border position for the border between the normal tissue and the tumor tissue or infected tissue. The method then indicates the border by pixels having an excess contrast-to-noise ratio larger than a predetermined threshold value.

In some examples, an identified contour of the target region is shown on a display, for example superposed on the fluorescence image. This may serve as an aid to a medical specialist to perform an intervention to a selected portion of the tissue corresponding to the target region in the fluorescence image, for example by treating the selected tissue portion with therapeutic radiation, by supplying a pharmaceutical agent for treatment in the selected tissue portion represented in the target region, by selectively activating a pharmaceutical agent for treatment in the selected tissue portion or by excising the selected tissue portion. Instead of superposing the contour on the fluorescence image it also possible to superpose the contour on a natural image of the tissue, i.e. an image that appears to have been taken under ambient light conditions. Therewith the medical specialist can monitor the tissue while performing the medical intervention as if he/she were directly seeing the tissue under ambient light conditions instead of monitoring the fluorescence response of the image. In a still further example the contour is projected onto the tissue.

The present disclosure also provides an improved inspection device for inspection of a luminescence, in particular fluorescence image represented as an array of pixels having respective fluorescence signal values (FI(p)) and configured to carry-out a method as disclosed herein.

In an example, the improved inspection device is further configured to perform the following operations for indicating the border:

First the inspection device obtains respective fluorescence signal vectors ($F_L$( . . . )) for respective scan trajectories (L). Each scan trajectory (L) extends through a tissue area (TA). A scan trajectory is typically a scan line, but may alternatively be a curve.

Respective values of a respective fluorescence signal vector ($F_L$( . . . )) are an indication of a magnitude of the fluorescence signal in the fluorescence image (FI) at respective positions (p) of the scan trajectory (L).

In this example the inspection device evaluates respective excess contrast-to-noise ratio vectors ($mCNR_{LM}$( . . . )) for respective fluorescence signal vectors ($F_L$( . . . )). Respective values of respective excess contrast-to-noise ratio vectors ($mCNR_{LM}$( . . . ) are computed for respective positions (p) of the scan trajectory (L) as follows.

$$mCNR_{LM}(p) = \frac{F_L(p) - F_B - c \cdot S}{c \cdot S} \quad (1a)$$

Therein $F_B$ is a reference fluorescence signal value being an average value of reference fluorescence signal values of the fluorescence image, S being a standard deviation of the reference fluorescence signal values and c being a regularization parameter.

The exemplary image inspection device is configured to repeat the following steps for each of a plurality of positions along the scan trajectory:

- tentatively assign a position (ps) from said plurality of positions along the scan trajectory as a presumed point of the border indicating the border of the target region;

compute the average of the fluorescence signal values of the fluorescence signal vector ($F_L(\ldots)$), corresponding to positions of the scan trajectory at a first side of the tentatively assigned position to obtain the quantity FB0;

compute the average of the fluorescence signal values of the fluorescence signal vector ($F_L(\ldots)$), corresponding to positions of the scan trajectory at a second side opposite the first side of the tentatively assigned position to obtain the quantity FB1;

If FB0>FB1 then it is presumed that the tumor is represented in the first side and the value FB1 represents the reference fluorescence signal value FB and the standard deviation(S) is the standard deviation of the fluorescence signal values at the second side;

If FB0 < FB1 then it is presumed that the tumor is represented in the second side and the value FB0 represents the reference fluorescence signal value FB and the standard deviation(S) is the standard deviation of the fluorescence signal values at the first side;

identifying a tentatively assigned position as a candidate border position if the excess contrast-to-noise ratio vector ($mCNR_{LM}(\ldots)$) has a zero-crossing at the tentatively assigned position;

indicating the border based on the set of candidate border positions obtained for the respective scan trajectories.

In an embodiment the image inspection device is configured to indicate the border as a primary curve that interconnects peripheral candidate border positions.

In another embodiment the image inspection device is configured to indicate the border with a secondary curve that encloses a primary curve that interconnects the peripheral candidate border position, and that extends at a distance outside the primary curve dependent on the type of tumor present in the tissue. Guidelines for the distance to be selected i.e. the tumor-free margin depend on the type of tumor, and are presented in Table 1 of Voskuil et al. "Intraoperative imaging in pathology-assisted surgery", Nat Biomed Eng. 6 (2022) 503, https://doi.org/10.1038/s41551-021-00808-8. In a further elaboration of this embodiment the image inspection device is configured to construct the secondary curve in a manner that avoids an intersection of specified anatomical structure(s). In an embodiment of the image inspection device the indication of the magnitude of the fluorescence signal in the fluorescence image at a position of the scan trajectory is an average value of fluorescence signal values of pixels in the fluorescence image within a one-dimensional window comprising that position and being directed transverse to a direction of the scan trajectory. This operation results in a magnitude indication with an improved signal to noise ratio in particular in case the scan trajectory crosses the border to be determined in a substantially transverse direction thereof. In a specific example the average value is determined as a weighted sum of the fluorescence signal values of the pixels within a one-dimensional window in accordance with a Gaussian function having its maximum at the position of the scan trajectory.

In an embodiment the image inspection device is configured to repeat the following steps for each of a plurality of positions along the scan trajectory.

The image inspection device tentatively assigns a position from the plurality of positions along the scan trajectory as a presumed point of the border of the target region.

The image inspection device computes the reference fluorescence signal value as the average of the fluorescence signal values of the fluorescence signal vector corresponding to positions of the scan trajectory at a side of the tentatively assigned position.

The image inspection device computes the standard deviation as the standard deviation of the fluorescence signal values along that side of the scan trajectory.

In an example a respective average fluorescence signal value is computed for the scan trajectory positions on the scan trajectory at each side of the tentatively assigned position and the side having the lowest average fluorescence signal value is presumed to be in the reference region. Hence, the lowest average fluorescence signal value is used as the reference fluorescence signal value and the standard deviation used is the standard deviation of the fluorescence signal values along the side of the scan trajectory with the lowest average fluorescence signal value.

The image inspection device identifies the tentatively assigned position as a candidate border position if the excess contrast-to-noise ratio vector has a zero-crossing at the tentatively assigned position.

In this embodiment the plurality of positions may typically include all positions of the scan trajectory except the ends thereof, so that at least two signal values are available to estimate the standard deviation. In an example the image inspection device is configured to perform a low-pass filtering of the excess contrast-to-noise ratio vector. Therewith occurrences of spurious zero-crossings are mitigated.

In an embodiment of the image inspection device the respective scan trajectories comprise at least two scan trajectories with a mutually different direction. The candidate border positions will typically indicate positions where the scan trajectory crosses the border in a direction transverse to the scan trajectory. Accordingly, a more complete set of candidate border position is obtained with scan trajectories of mutually different directions. For example the scan trajectories comprise a first set of scan trajectories in a horizontal direction and a second set of scan trajectories in a vertical direction. This embodiment is computationally very efficient. At the cost of an increased computational effort, additional candidate border positions can be computed with a larger number of scan trajectory directions. For example sets of scan trajectories may be used for each direction being a multiple of n degrees, wherein n for example is 10.

As noted above, the image inspection device may be applied both for in-vivo and ex-vivo analysis. In case the image inspection device is used for ex-vivo analysis, the fluorescence image is obtained from a tissue sample that is taken from the subject and subsequently arranged on a background, typically a dark background. In an embodiment the image inspection device is configured to identify an area in the fluorescence image that represents the tissue sample as the tissue area and to identify an area in the fluorescence image of the background as the background area. In an example of this embodiment the image inspection device is further configured to determine a first maximum intensity in the target area of the fluorescence image, to determine a second maximum intensity along a scan trajectory and to skip further processing steps for the scan trajectory if the second maximum intensity is less than a predetermined fraction of the first maximum intensity.

In an embodiment the image inspection device is alternatively or additionally configured to reject a candidate border position for further processing if an indicated value for the fluorescence intensity is less than a threshold value. The indicated value can be the intensity value of the fluorescence image at the location of the candidate border position to be decided about. However, a reduced noise sensitivity in this candidate border position filtering operation can be achieved in an implementation wherein the indicated value is the maximum of the fluorescence intensities within a window centered around the candidate border position. This is the value that is indicated by the "movmax" function, wherein the size of the window may be selected in a range of 2 to 10 pixels, for example 5 pixels.

In an embodiment the image inspection device comprises a camera for obtaining a fluorescence image from tissue in a subject, and further comprising a display device to display the tissue and one or more indications of the border, e.g. as a primary curve and/or as a secondary curve that encloses the primary curve. This embodiment is particular suitable for use during treatment to guide the medical specialist in the process of excising the tumor or irradiating the tumor. In this case the patient to which the treatment is performed has been administered a fluorescent agent.

In an embodiment, the inspection device is further configured to:

determine an average fluorescence signal value (PR) and a standard deviation ($\sigma_R$) of the fluorescence signal values comprised in the second number of fluorescence pixel values;

perform an image segmentation to distinguish in the fluorescence image (FI) a target region (TR) to denote a portion in the mammal tissue (MT) that is identified as tumorous tissue or infected tissue and a reference region (RR) to denote a remaining portion in the mammal tissue (MT), wherein the device is configured to determine per pixel (p) that it is part of the target region (TR) if an excess contrast-to-noise ratio mCNR (p) for said pixel exceeds a predetermined threshold value ($T_{CNR}$) and to determine that the pixel is part of the reference region (RR) otherwise, wherein the excess contrast-to-noise ratio mCNR (p) of a pixel is defined as $$\tilde{m}CNR(p) = \frac{FI(p) - \mu_R}{c \cdot \sigma_R} \quad (1b)$$

wherein FI(p) is the fluorescence signal value of the pixel (p) and c is a regularization parameter;

identify a contour of the target region (TR).

The improved inspection method and the inspection device carrying out the inspection method are for example applicable to process a fluorescence image obtained from a tissue of a subject so as to facilitate a specialist or a surgery device to perform a therapy.

BRIEF DESCRIPTION OF THE DRAWINGS

These and other aspects of the present disclosure are described in more detail with reference to the drawings. Therein FIG. 1 schematically shows an embodiment of an image inspection device according to the first aspect;

FIGS. 27A and 27B shows a further optional step of the improved inspection method;

DETAILED DESCRIPTION OF EMBODIMENTS

Figure 1:
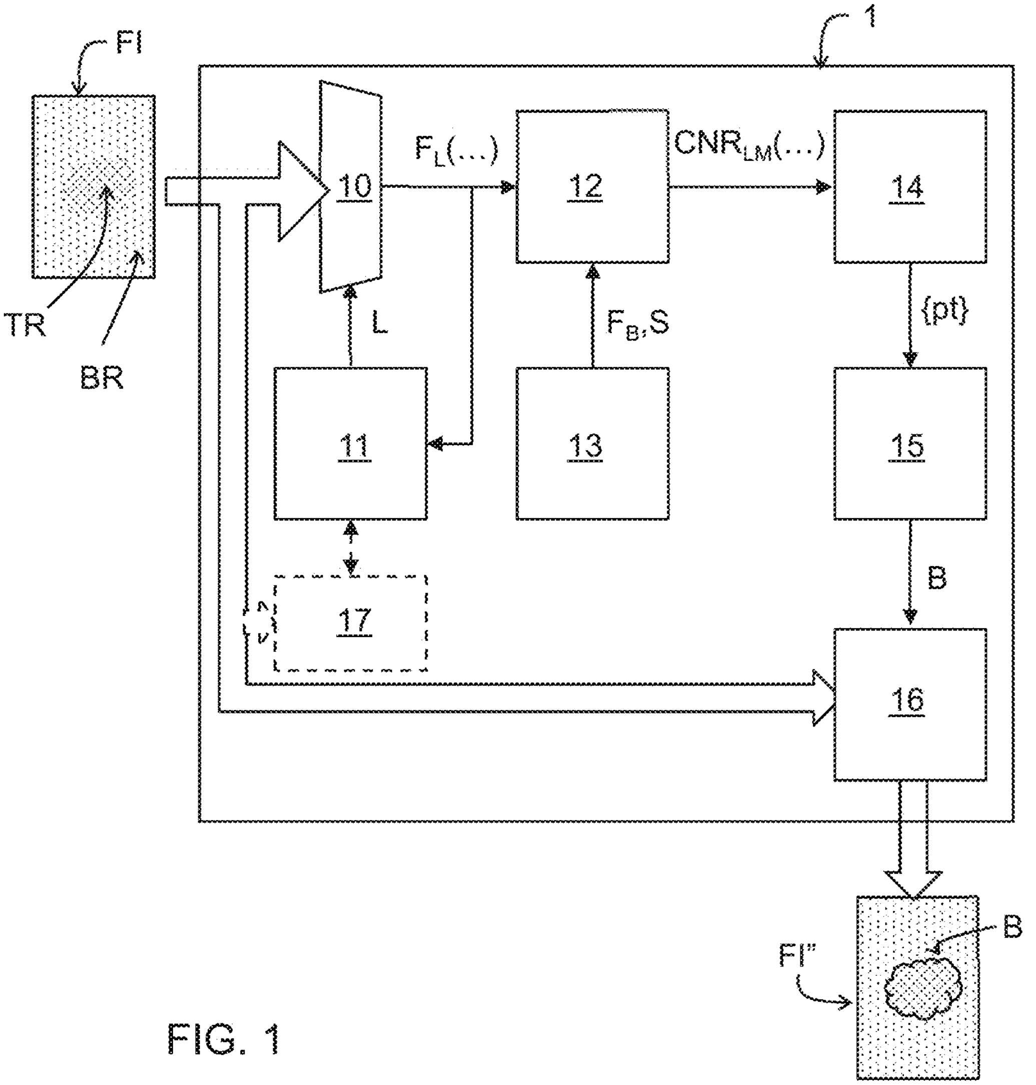

FIG. 1 schematically shows an image inspection device 1 that is configured to process a fluorescence image FI of a tissue of a subject. The tissue is rendered photosensitive with a fluorescent agent, e.g. a contrast agent and is irradiated with excitation radiation. The fluorescence image FI so obtained comprises an array of pixels having respective fluorescence signal values. The image inspection device 1 is configured for determining a border in the fluorescence image between a target region TR representing a portion of the tissue comprising a tumor and a reference region RR outside the target region.

The image inspection device 1 has a signal vector retrieval module 10 configured to obtain respective fluorescence signal vectors $F_L(\ldots)$ for respective scan trajectories L as indicated by scan trajectory selection module 11. Respective values of a fluorescence signal vector FI ( . . . ) indicate a magnitude of the fluorescence signal in the fluorescence image FI at respective positions p of the scan trajectory L.

An excess contrast-to-noise ratio computation module 12 computes a respective excess contrast-to-noise ratio vector $mCNR_{LM}(\ldots)$ for each fluorescence signal vector $F_L(\ldots)$. The corresponding respective values contained in an excess contrast-to-noise ratio vector $mCNR_{LM}(\ldots)$ are computed from a fluorescence signal vector $F_L(\ldots)$ for respective positions p of the scan trajectory L as $$mCNR_{LM}(p) = \frac{F_L(p) - F_B - c \cdot S}{c \cdot S} \tag{1a}$$

Therein a statistic module 13 provides a reference fluorescence signal $F_B$ which is an average value of reference fluorescence signal values of the fluorescence image and a standard deviation S of the reference fluorescence signal values. Furthermore, c is a regularization parameter. For example c=2.

Zero crossing detection module 14 identifies a respective set of transition positions {pt} along each scan trajectory. These are the positions where the excess contrast-to-noise ratio vector $mCNR_{LM}(\ldots)$ has a zero-crossing.

The scan trajectory selection module 11 selects a plurality of mutually different scan trajectories and for each selected scan trajectory a respective set of transition positions is determined.

The border indication module 15 subsequently indicates the border between the target region TR the reference region RR based on the sets of transition positions obtained for the respective scan trajectories.

In the embodiment shown, the image inspection device 1 further comprises a display module 16, that generates a modified fluorescence image FI" wherein the border B indicated by the border indication module 15 is superposed on the original fluorescence image FI. In case the original fluorescence image FI is obtained in-vivo, this image can assist the surgeon in the process of excising the tumor or irradiating the tumor with therapeutic radiation.

The scan trajectory selection module 11 subsequently selects scan trajectories L from a set of scan trajectories and instructs the signal vector retrieval module 10 to obtain a fluorescence signal vector of which respective fluorescence signal vector values are an indication of a magnitude of the fluorescence signal in the fluorescence image FI at respective positions p of the scan trajectory L with respective coordinates $x_p$, $y_p$ in the fluorescence image FI. In one example the fluorescence signal vector values correspond to the magnitudes of the fluorescence signal in the fluorescence image FI at the respective positions p of the scan trajectory L. In another example the indication FL(p) of the magnitude of the fluorescence signal in the fluorescence image FI at the position of the scan trajectory L is an average value of fluorescence signal values of pixels in the fluorescence image FI within a one-dimensional window comprising the position with coordinates $x_p$, $y_p$ and being directed transverse to a direction of the scan trajectory.

Accordingly $$FL(p) = \sum_{q=-n}^{q=n} w_q FI(x_q, y_q) \tag{4}$$

$$\text{wherein } \sum_{q=-n}^{q=n} w_1 = 1 \tag{5}$$

Therein the position $x_q$=0, $y_q$=0 coincides with the position $x_p$, $y_p$. By way of example the weight factors are mutually equal, i.e.

$$w_q = \frac{1}{2n+1}. \tag{5a}$$

In a preferred embodiment the average value is a weighted sum of the fluorescence signal values of the pixels within the one-dimensional window in accordance with a Gaussian function or a similar weighting function having its maximum at the position p of the scan trajectory L.

When using the image inspection device 1 in an intraoperative mode, the fluorescence image FI is obtained from a tissue sample taken from the subject and arranged on a background. In an embodiment the image inspection device 1 comprises a foreground identification module 17 (indicated in dashed lines) with which the image inspection device 1 is configured to identify an area in the fluorescence image that represents the tissue sample as the tissue area and to identify an area in the fluorescence image FI of the background as the non-tissue area. In an example of this embodiment the foreground identification module 17 (indicated by dashed lines) is further configured to determine a first maximum intensity in the tissue area of the fluorescence image FI, to determine a second maximum intensity along a scan trajectory and to skip further processing steps for the scan trajectory if the second maximum intensity is less than a predetermined fraction of the first maximum intensity.

In the embodiment of FIG. 1, it is presumed that reference fluorescence signal $F_B$ and the standard deviation S are predetermined values.

Figure 2:
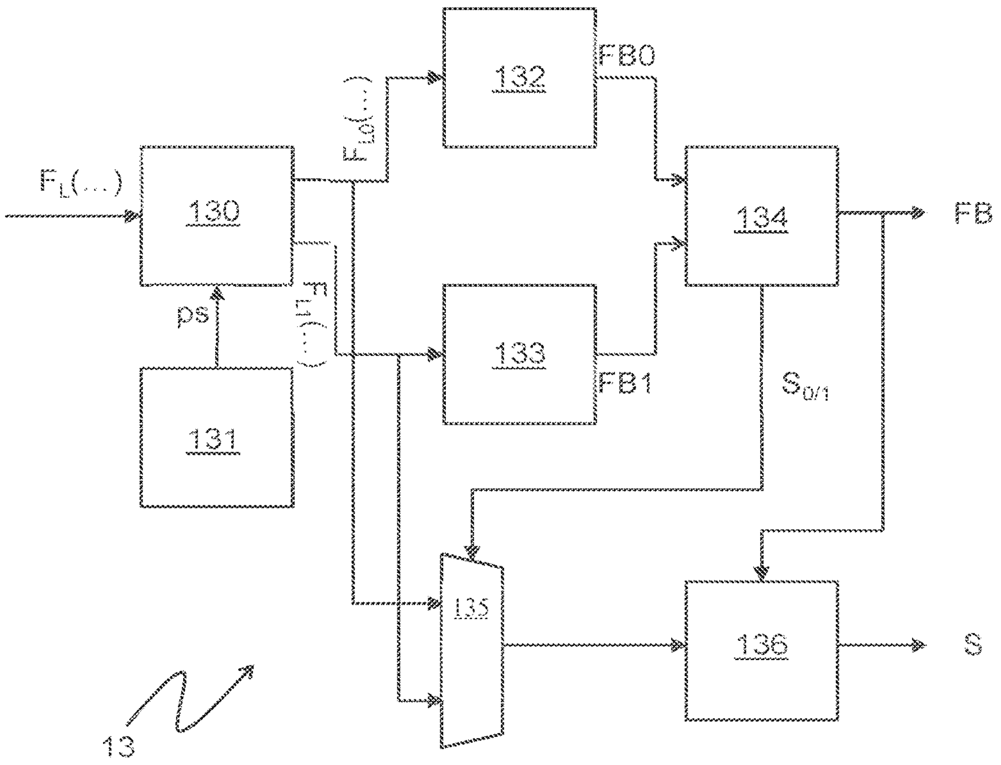
FIG. 2 shows an exemplary module in another embodiment thereof.

FIG. 2 shows an alternative embodiment for the statistic module 13 that dynamically determines these parameters $F_B$ and S as a function of the fluorescence signal vector data $F_L$.

The statistic module 13 comprises a vector splitting section 130 that splits the fluorescence signal vector $F_L$ ( . . . ) into a first portion $F_{L0}$ and a second portion $F_{L1}$. The first portion $F_{L0}$ comprises the fluorescence signal vector $F_L$( . . . ) data corresponding to a first side of the scan trajectory respective to a position ps of the scan trajectory that is tentatively assigned by position assigning section 131. The second portion $F_{L1}$ comprises the fluorescence signal vector $F_L$ ( . . . ) data corresponding to an opposite side of the scan trajectory respective to the position ps. Each of the portions may or may not include the fluorescence signal vector $F_L$ value for the position ps. A first average value computation section 132 computes the average value FB0 of the values of the first portion $F_{L0}$( . . . ) of the fluorescence signal vector $F_L$ ( . . . ). Analogously, the second average value computation section 133 computes the average value FB1 of the values of the second portion $F_{L1}$( . . . ) of the fluorescence signal vector $F_L$( . . . ). Alternatively a single section may subsequently compute these values FB0, FB1. Decision section 134 determines whether or not the value FB0 exceeds the value FB1. If this is the case it determines that FB=FB1. Otherwise it determines that FB=FB0. Decision section 134 also issues a control signal Son to data selector 135. In the first case, FB=FB1, it controls the data selector 135 to select the second portion $F_{L1}$( . . . ) of the fluorescence signal vector $F_L$ ( . . . ) as the input for the standard deviation computation section 136 so as to compute the standard deviation S from the fluorescence signal data of the second portion $F_{L1}$( . . . ) of the fluorescence signal vector $F_L$ ( . . . ). In the second case, FB=FB0, the data selector 135 is controlled to select the first portion $F_{L0}$( . . . ) of the fluorescence signal vector $F_L$ ( . . . ) as the input. In an embodiment the position assigning section 131 assigns subsequent positions ps of the scan trajectory, and for each tentatively assigned position the corresponding parameters $F_B$ and S are determined and used to compute a respective excess contrast-to-noise ratio. In addition, zero crossing detection module 14 specifically selects those tentatively assigned positions as candidate border positions if the excess contrast-to-noise ratio vector ($mCNR_{LM}$( . . . )) has a zero-crossing at the tentatively assigned position.

Figure 3:
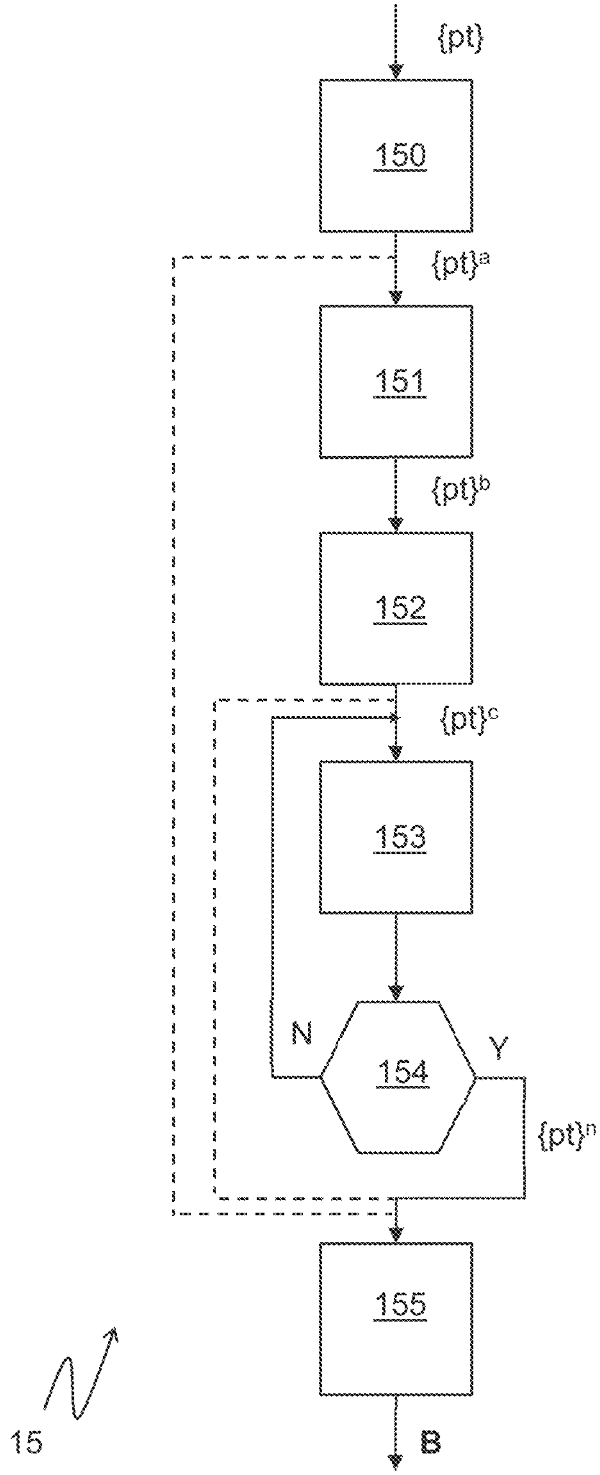
FIG. 3 shows a further exemplary module.

An embodiment of the border indication module 15 is shown in more detail in FIG. 3.

The border indication module 15 shown therein comprises a candidate border position filter section 150 that is configured to reject a candidate border position for further processing if an indicated value for the fluorescence intensity is less than a threshold value. In an example the indicated value is the maximum of the fluorescence intensities within a window centered around the candidate border position to be decided about. In an example the maximum value is obtained from an auxiliary image FIa that is derived once from the original fluorescence image and stored for subsequent references. The auxiliary image FIa is for example derived in a two-pass procedure, wherein in a first pass for each pixel (x,y) the value FIh(x,y) is determined as $$FIh(x, y) = \max\{FI(x-w, y), \ldots , FI(x+w, y)\} \tag{6a}$$

And in a second pass $$FIa(x, y) = \max\{FIh(x, y-w), \ldots , FIh(x, y+w)\} \tag{6b}$$

In an example the threshold value is selected as a percentage of the maximum value over the complete fluorescence image FI. The percentage may be selected in a range of 10-80, more preferably in a range from 40 to 60% depending on the tissue being imaged. For a sample with a smooth surface, such as a bread loaf slice of a tissue 40% is a suitable choice. For samples with a higher surface roughness the percentage should be higher. The size of the window 2w+1 is selected in a range from 2 to 10, wherein 5 was found to be optimal, i.e. corresponding to w=2.

The embodiment of the border indication module 15 shown in FIG. 3 further comprises a candidate border position matching section 151 that matches candidate border positions obtained from each pair of scan trajectories that mutually overlap but have mutually opposite scan directions. The candidate border position matching section 151 verifies whether a candidate border position obtained with a first scan trajectory of the pair has a corresponding candidate border position in the second scan trajectory of the pair. The candidate border positions are considered to correspond if their associated positions in the fluorescence image do not exceed a threshold distance, e.g. 1 or 2 pixels. Furthermore, it may be required that the candidate border positions are of mutually opposite polarities. That is to say if one of them indicates a crossing of the border in the direction from the reference region to the target region, then the other one should indicate a crossing in the direction from the target region to the reference region.

In the embodiment shown, the border indication module 15 comprises a further candidate border position matching section 152 that matches pairs of mutually non-coinciding but neighboring candidate border positions obtained from mutually different scan trajectories, i.e. having a relative angle other than 0 or 180 degrees. The further candidate border position matching section 152 identifies pairs of a first candidate border position obtained from a first scan trajectory and a second candidate border position obtained from a second scan trajectory that have a Euclidian distance less than a predetermined maximum, e.g. 3 pixels and replaces the pair of mutually neighboring candidate border positions with a single replacement candidate border position centrally between the mutually neighboring candidate border positions. It is noted that instead of the Euclidian distance measure also a different distance measure may be taken, for example the L1 measure that computes the distance as the sum of the distances along each of the main direction of the image or the L∞ measure that defines the distance as the maximum one of the distances in the main direction.

In the embodiment shown, the border indication module also comprises a candidate border position merging section 153. The candidate border position merging section 153 receives the remaining set $\{pt\}^b$ of candidate border positions from the further candidate border position matching section 152 and merges mutually neighboring ones of the remaining candidate border positions. As indicated by backwards directed arrow "N" the candidate border position merging section 153 may perform this operation a plurality of times. The decision section 154 determines whether the iteration should be stopped "Y" or not "N". In one example the iteration takes place a predetermined number of times, e.g. 3 to 5 times. In another example the decision section 154 determines whether a data dependent stop criterion is complied with, e.g. the number of remaining candidate border positions is reduced to below a threshold value. The threshold value may be predetermined or may depend on other information. For example the threshold value is a constant times the square root of the total number of pixels within a convex hull comprising all remaining candidate border positions. The border construction section 155 receives the set $\{pt\}^n$ of selected candidate border positions, based on the set of transition positions, from the candidate border position merging section 153 and constructs an indication of the border B.

In an example the border construction section 155 performs the MatLab function boundary (x,y,s). Therein the value s may be selected in a range of 0.1-1, typically in a range from 0.5-1. Best results were obtained a value selected in the range of 0.8 to 1. However the value s=0.5, which is the default value also provides good results.

As shown by dashed lines in FIG. 3, in some examples the border indication module 15 is configured to skip one or more of the operations specified above. For example the border construction section 155 directly constructs a border from a filtered set $\{pt\}^a$ of candidate border positions retrieved from candidate border position filter section 150. In another example the border construction section 155 constructs a border from a set $\{pt\}^c$ of candidate border positions retrieved from further candidate border position matching section 152.

In one example the border construction section 155 is configured to indicate the border B as a primary curve that interconnects the peripheral transition positions.

Figure 4:
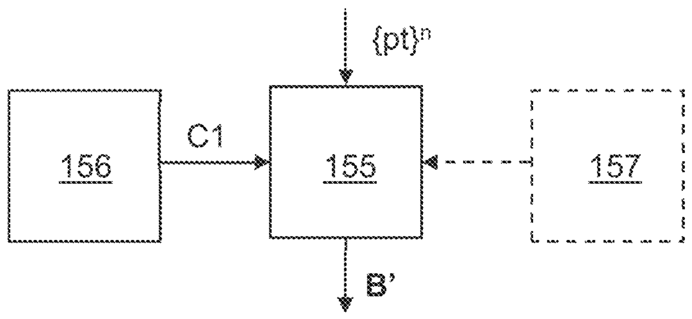
FIG. 4 shows a part of the module of FIG. 3 in more detail.

In another example as shown in FIG. 4, the border construction section 155 is configured to construct the border as a secondary curve B' that encloses a primary curve that interconnects the peripheral transition positions, and that extends at a distance outside the primary curve dependent on the type of tumor present in the tissue. To that end it receives a control signal C1 from a distance control section 156 that specifies the predetermined distance. In response thereto the border construction section 155 will indicate the border with a secondary curve B' that extends outside the primary curve such that the distance between each point of the secondary curve and the corresponding closest point of the primary curve is equal to the predetermined distance.

In a variation of the embodiment of FIG. 4 the border construction section 155 is further configured to construct the secondary curve in a manner that avoids an intersection of a specified anatomical structure. For that purpose, in that variation also a critical tissue protection section 157 is provided as shown in dashed lines in FIG. 4. The critical tissue protection section 157 comprises information about the location of critical tissues, such as vital organs and based on this information the border construction section 155 construct the secondary curve B' such that it extends by default outside the primary curve B at the predetermined distance, but locally at a smaller distance to avoid an intersection of vital organs.

Figure 5:
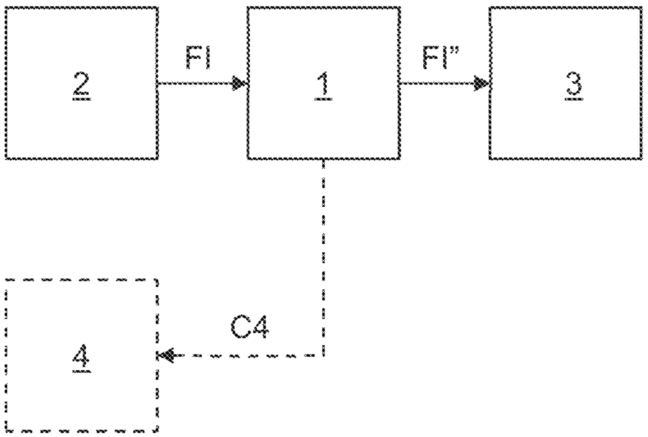
FIG. 5 shows a further embodiment of an image inspection device according to the first aspect of the invention.

FIG. 5 shows an embodiment of the image inspection device 1, that is particularly suitable for use as a tool during a treatment. Therewith it is presumed that the subject to be treated has been administered a fluorescent agent. In this embodiment the image inspection device 1 for example the embodiment of FIG. 1 or a variation thereof, is further extended with a camera 2 for obtaining a fluorescence image FI from tissue to be treated in the patient, and with a display device 3 to display the tissue and the indication B of the border as shown in the modified fluorescence image FI". In a variation the image inspection device 1 shows superposed on the fluorescence image the secondary curve B' as referred to above, optionally in combination with the indication by the primary curve B. In the example shown the image inspection device 1 is further configured to issue control signals C4 to control an excitation light source 4, which is for example a near-infrared (NIR) or a short-wave infrared (SWIR) source. Therewith the image inspection device 1 may control a wavelength and an intensity of the excitation light source 4 so as to optimize a contrast in the fluorescence image FI. Alternatively, a separate excitation light source 4 may be used having predetermined settings known to achieve good results.

Figure 6:
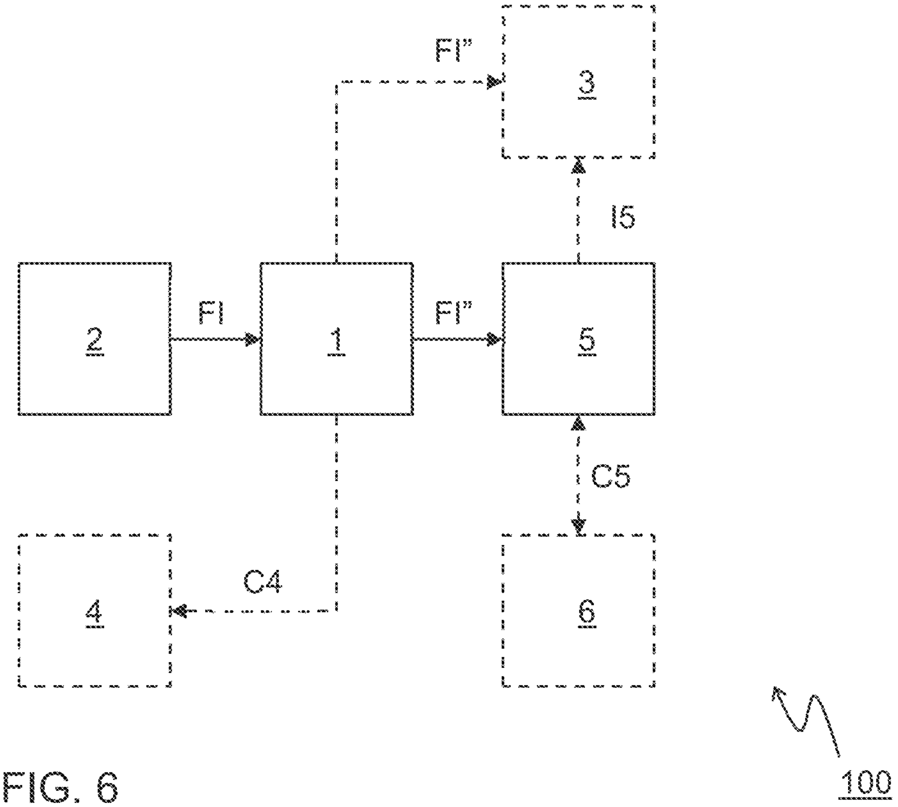
FIG. 6 shows an embodiment of a medical treatment device according to the second aspect.

FIG. 6 shows an embodiment of medical treatment device 100, that is suitable to automatically perform a medical treatment to a patient in order to treat a tumor present in a tissue. As in the case of FIG. 5, it is presumed that the subject to be treated has been administered a fluorescent agent. The medical treatment device 100 comprises in addition to the image inspection device 1, for example the embodiment of FIG. 1 or a variation thereof, a camera 2 for obtaining a fluorescence image FI from the tissue with the tumor and medical treatment equipment 5 to perform a treatment to excise or irradiate the tumor in accordance with the indicated border or to or to activate a therapeutic substance in the range specified by the indicated border.

As in the embodiment of FIG. 5, the image inspection device 1 may be further configured to issue control signals C4 to control an excitation light source 4, for example a near-infrared (NIR) or a short-wave infrared (SWIR) source. Even if the medical treatment device 100 is suitable to automatically perform a medical treatment it may be desired to monitor its operation. To that end a display device 3, as indicated by dashed lines, may be provided that displays the modified fluorescence image FI". In addition the medical treatment equipment 5 may provide an information signal 15 to the display device 3 to indicate a progress of the treatment. Also, the medical treatment equipment 5 may be coupled to a user interface 6 with which a medical specialist can fully or partly control the operation of the medical treatment equipment 5 via control signals C5.

Example I

Figure 7A:
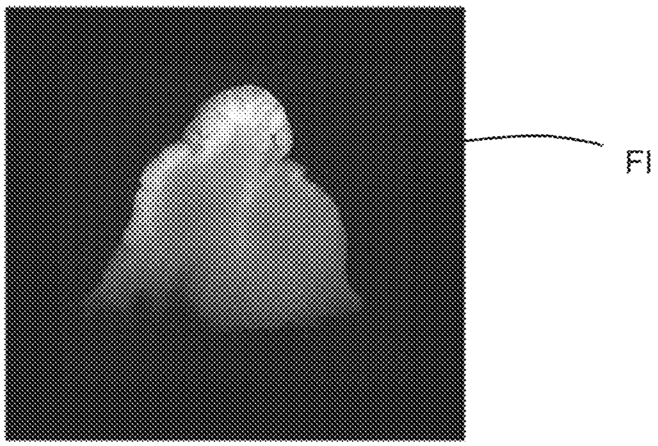
FIG. 7A shows a fluorescence image captured from a tissue comprising a tumor.

By way of example FIG. 7A shows a fluorescence image FI captured from a tissue comprising the tumor arranged on black background. In an example the fluorescence image has a width Nx of 400 pixels, a height Ny of 600 or 700 pixels and the resolution is for example in the order of 100 micron per pixel, e.g. 85 micron per pixel.

In the example shown, tissue from which the fluorescence image is obtained is a slice of the volume of tissue that is excised from a subject. The tumor in this case is a penile cancer and the subject was administered before treatment with cetuximab-IRDye800CW as a fluorescent agent.

Alternatively the fluorescence image is obtained from the excised volume of tissue, i.e. the resection-specimen itself.

In subsequent operations the image inspection device 1 identifies a first area in the fluorescence image that represents the tissue sample as the tissue area and identifies an area in the fluorescence image FI of the background as the background area BA. In an example these operations are performed by the foreground identification module 17.

Figure 7B:
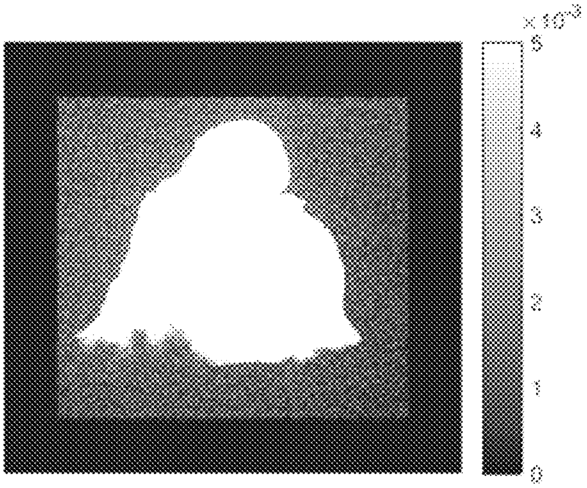
FIG. 7B shows the result of a first conversion step applied to the fluorescence image.

In a first exemplary operation the foreground identification module 17 converts the fluorescence image FI into a binary image, as shown in FIG. 7B, wherein pixels having an intensity in the fluorescence image exceeding a threshold value have a first binary value, represented as white pixels in FIG. 7B and the remaining pixels have a second binary value, represented are dark pixels in the figure. The threshold value to be selected for this purpose depends on the choice of the input device that provides the fluorescence image FI. For the PEARL imaging system the threshold maybe selected in the range of 0.001-0.01. For example a threshold value 0.005. For the SurgVision imaging system the threshold value may be selected in the range of 500-2000, for example a threshold value of about 800.

Areas formed by pixels with the first binary value are denoted candidate foreground areas. Areas formed by pixels with the second binary value are denoted candidate background areas.

Figure 7C:
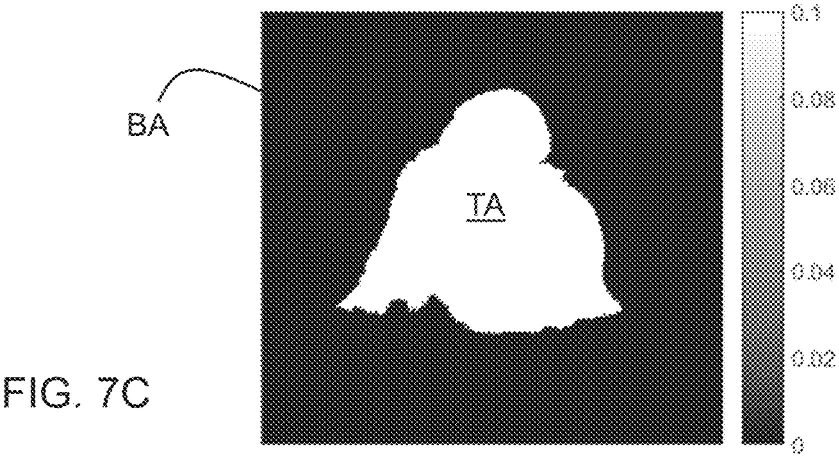
FIG. 7C shows the result of a second conversion step applied to the result shown in FIG. 7B.

Subsequently the foreground identification module 17 performs a dilation operation to dilate the candidate foreground areas. Typically a dilation by one pixel is sufficient to avoid that occasionally image data would be lost at edge portions of the tissue. As shown in FIG. 7B. due to noise, in addition to a single large candidate foreground area a plurality of small candidate foreground area is present. In order to mitigate this phenomenon, the foreground identification module 17 performs an additional operation wherein it selects the largest one of the candidate foreground areas as the foreground area TA representing the tissue. Therewith the result shown in FIG. 7C is obtained. The resulting binary image of FIG. 7C is used as a mask to indicate the boundary in the fluorescence image FI between the foreground area representing the tissue and the remaining background area therein.

Figure 8:
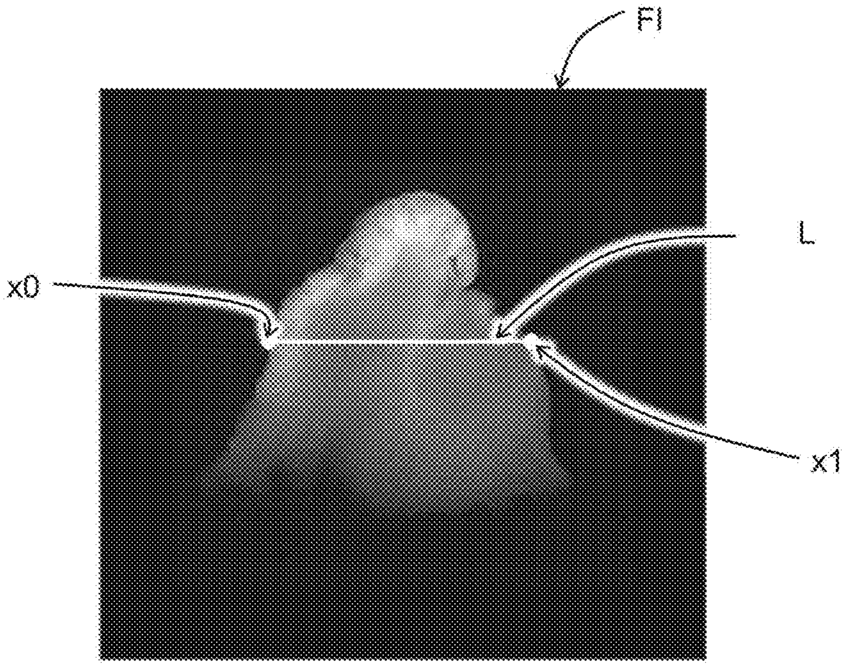
FIG. 8 illustrates a first data processing operation.

In an example the foreground identification module 17 also determines the maximum intensity Imax,fg of the fluorescence image FI in the foreground area (denoted as TA in FIG. 7C). It could also be contemplated to determine the maximum intensity over the complete area of the fluorescence image FI. This would however be more sensitive to noise, as even in the background area isolated pixels might have a high intensity As shown in FIG. 8, the scanline selection module 11 constructs at least one scan trajectory L that extends through the foreground area TA (as shown in FIG. 7C) and that is delimited by the boundary with the background area. In the example shown the scan trajectory is a line extending in the horizontal direction between a first boundary with the background at a position x0 and a second boundary with the background at a position x1. Based on the indication L of the scan trajectory the signal vector retrieval module 10 obtains a fluorescence signal vector $F_L(\ldots)$. Respective values of a fluorescence signal vector $F_L(\ldots)$ indicate a magnitude of the fluorescence signal in the fluorescence image FI at respective positions p of the scan trajectory L. A constructed scan trajectory may represent a strip having a width that exceeds 1 pixel. In that case each value of the fluorescence signal vector $F_L(\ldots)$ is a weighted sum of the intensities of the pixels within the width of the strip. I.e. if the line extends in a first direction x, the strip has a width in the direction y, and the weighted sum is computed of the pixels within the width of the strip having the same x-coordinate. The weighted sum can be a plain average wherein the weighting factor for each pixel is the same, but can alternatively be a gaussian weighting function. In case the foreground area is concave, more trajectories on a same line may be constructed that each have a respective pair of endpoints at a respective pair of points on the boundary. Experiments were performed for different values of the strip width in a range of 3-21 pixels. Best results were obtained for a strip width of 11 pixels, but other selections from this range were also found to be suitable.

In an example the scanline selection module 11 determines for each scan trajectory L the maximum of the values of the fluorescence signal vector $F_L(\ldots)$ which is denoted as Imax,ln. Also in this example it determines whether or not the maximum intensity Imax,ln is at least equal to a predetermined percentage, e.g. about 10%, of the maximum intensity Imax, fi of the foreground area of the fluorescence image as a whole. Experiments were performed for various values of the predetermined percentage selected from 0, 1, 10, 33 and 50%. Best results were obtained with 33 as the predetermined percentage.

If in this example, it is determined that the maximum intensity Imax, ln found among the values of the fluorescence signal vector $F_L(\ldots)$ is less than the predetermined percentage of the maximum intensity Imax, fi the scan trajectory L is not selected for further processing. This deselection is based on the assumption that the lack of high intensity pixels along the scan trajectory indicates the absence of tumor tissue in the path through the tissue corresponding to the scan trajectory. The predetermined percentage may be selected in a range of 10% to 50%. Experiments indicated a percentage of 40 as optimal.

However, if it is determined that the maximum intensity Imax, ln found among the values of the fluorescence signal vector $F_L(\ldots)$ is at least equal to the predetermined percentage of the maximum intensity Imax,fi, the excess contrast-to-noise ratio computation module 12 computes an excess contrast-to-noise ratio vector $mCNR_{LM}(\ldots)$ for a fluorescence signal vector $F_L(\ldots)$. Based on the excess contrast-to-noise ratio vector $mCNR_{LM}(\ldots)$ data one or more positions are estimated where the scan trajectory traverses a border between a sub-area with healthy tissue and a sub-area with tumor tissue. A position where the scan trajectory traverses a border in the direction from a sub-area with healthy tissue to a sub-area with tumor tissue is characterized by a zero-crossing in a direction from a negative polarity to a positive polarity of the excess contrast-to-noise ratio vector $mCNR_{LM}(\ldots)$ and a position where the scan trajectory traverses a border in the direction from a sub-area with tumor tissue to a sub-area with healthy tissue is characterized by a zero-crossing in a direction from a positive polarity to a negative polarity.

In one example the excess contrast-to-noise ratio computation module 12 computes the excess contrast-to-noise ratio vectors $mCNR_{LM}(\ldots)$ based on respective predetermined values for the background intensity $F_B$ and the standard deviation S. This implementation is advantageous for the sake of a relatively low computational complexity. An alternative implementation with which the border can be determined with improved precision comprises the following procedure which is repeated for each pixel xs along the scan trajectory, excluding the ends of the scan trajectory. For simplicity it is presumed now that the scan trajectory extends in the x-direction and that the boundaries of the scan trajectory on the foreground with the background are x0, x1 respectively. Nevertheless, this description is equally applicable for arbitrary directions.

In this improved procedure it is presumed that the selected pixel xs coincides with the border, and that all pixels on the scan trajectory on a first side of the selected pixel xs represent tumor tissue and all pixels on the scan trajectory on a second side (opposite to the first side) of the selected pixel represent healthy tissue.

Based on this presumption, the vector splitting section 130 splits the fluorescence signal vector $F_L(\ldots)$ into a first portion $F_{L0}$ and a second portion $F_{L1}$. The first portion $F_{L0}$ represents the portion of the scan trajectory between the first endpoint, here with x coordinate x0, and the tentatively assigned border position xs. The second portion $F_{L1}$ represents the portion of the scan trajectory between the tentatively assigned border position xs and the second endpoint, here with x coordinate x1.

Based on this presumption, the first average value computation section 132 computes an average value FB0 of the values of the first portion $F_{L0}$ of the fluorescence signal vector $F_L$ ( . . . ). Likewise the second average value computation section 133 computes an average value FB1 of the values of the second portion $F_{L1}$ of the fluorescence signal vector $F_L$ ( . . . ).

Hence if ps (here xs) is the tentatively selected position on the scan trajectory and p0 (here x0) and p1 (here x1) are the positions of the end pixels then at each side of that position ps the average value of the intensities is determined as follows.

$$FB0 = \frac{\sum_{p0}^{ps} FL(p)}{1 + ps - p0} \tag{7a}$$

$$FB1 = \frac{\sum_{ps}^{p1} I(p)}{1 + p1 - ps} \tag{7b}$$

The tumor is considered to be represented in the pixels of the scan trajectory at the side of ps having the highest average intensity. The pixels on the scan trajectory on the opposite side, having the lowest average intensity are considered to represent the background. This determined by decision section 134. Based on this presumption the average value FB and the standard deviation S of the pixel values of the pixels on the scan trajectory on the second side of the selected pixel are computed.

Hence, if FB0>FB1 then it is presumed that the tumor is represented in the range p0-*ps* and the value FB1 represents the presumed average background intensity level $F_B$. In this case decision section 134 by means of selection signal Son causes data selector 135 to select the second portion $F_{L1}$ of the fluorescence signal vector $F_L$ ( . . . ) as the input for the standard deviation computation section 136. Accordingly in that case the standard deviation S is estimated as:

$$S = \sqrt{\frac{\sum_{ps}^{p1} FL^2(p) - FB^2}{p1 - ps}} \tag{8a}$$

Alternatively, if FB0≤FB1 then it is presumed that the tumor is represented in the range ps-p1 and the value FB0 represents the presumed average background intensity level $F_B$. In this case decision section 134 by means of selection signal Son causes data selector 135 to select the first portion $F_{L0}$ of the fluorescence signal vector $F_L$ ( . . . ) as the input for the standard deviation computation section 136. Accordingly in that case the standard deviation S is estimated as:

$$S = \sqrt{\frac{\sum_{p0}^{ps} FL^2(p) - FB^2}{ps - p0}} \tag{8b}$$

Based on values for the average background intensity $F_B$ and the standard deviation S, estimated for a tentatively assigned position ps, the excess contrast-to-noise ratio computation module 12 computes the excess contrast-to-noise ratio $mCNR_{LM}$(p) as $$mCNR_{LM}(p) = \frac{F_L(p) - FB - c \cdot S}{c \cdot S} \tag{1a}$$

Accordingly, for each presumed ps a vector $mCNR_{LM}$( . . . ) is obtained, resulting in a matrix wherein each row represents the values of $mCNR_{LM}$( . . . ) computed for a particular tentatively assigned position ps.

Figure 9A:
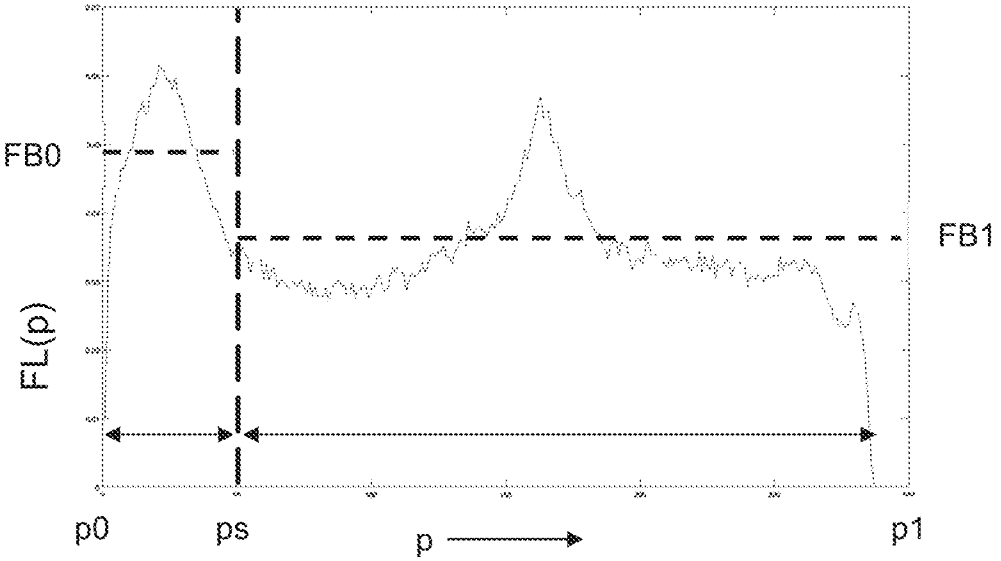
FIGS. 9A and 9B show results obtained in a second data processing operation.

By way of example FIG. 9A shows the values of the fluorescence signal vector FL(p) along a scan trajectory and the computed average values FB0 and FB1 for the first and the second portion of the fluorescence signal vector FL(p) based on the tentatively selected position ps. In this example the value FB1 is less than the value FB0, and it is presumed that the portion p0-*ps* extends within the image area representing the tumor and the portion ps-p1 extends within the area representing the healthy tissue. Accordingly, here the value FB1 is selected as the background value FB and the standard deviation S is computed from the values of the fluorescence signal vector FL(p) for the range ps-p1.

Figure 9B:
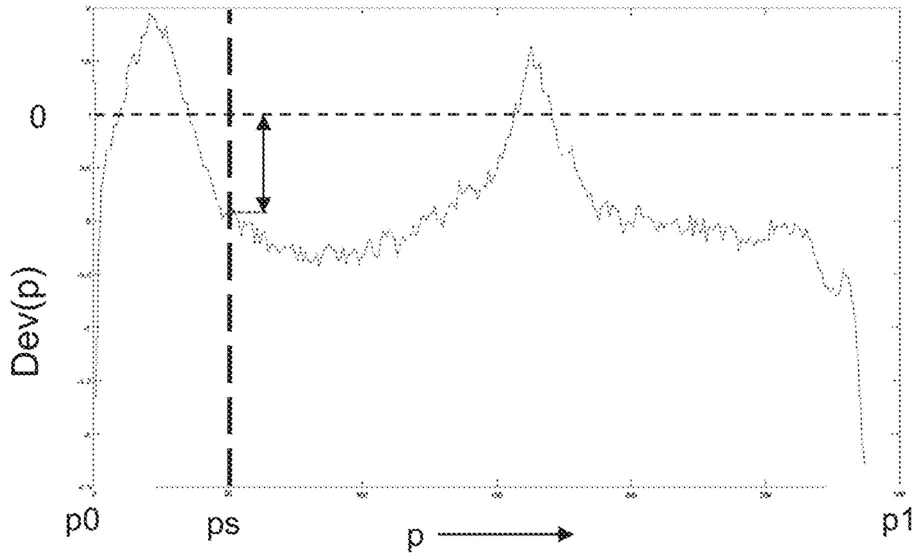

Therewith the excess contrast-to-noise ratio vector $mCNR_{LM}$( . . . ) is computed from the values of the fluorescence signal vector FL(p) as shown in FIG. 9B.

With this input, the zero crossing detection module 14 determines for which values of the tentatively assigned position ps the excess contrast-to-noise ratio vector $mCNR_{LM}$( . . . ) obtained for that position ps indeed has a zero-crossing. The corresponding positions of the scan trajectory in the fluorescence image FI are considered to represent candidate border positions. In the example shown in FIG. 9A, 9B, it can be seen that the excess contrast-to-noise ratio vector $mCNR_{LM}$( . . . ) obtained for the tentatively assigned position ps does not have a zero-crossing at that position ps. Therewith this position ps is not considered as a candidate border position.

It is noted that a low pass filter may be applied to each excess contrast-to-noise ratio vector $mCNR_{LM}$( . . . ) prior to identifying zero-crossings therein for the purpose of eliminating spurious zero-crossings resulting from noise. In an example the low pass filter has a normalized passband frequency of less than 0.5, typically less than 0.1. Optimum results were obtained with a normalized passband frequency of 0.045.

As such it is sufficient to determine only the presence of a zero-crossing at the position p of the excess contrast-to-noise ratio vector $mCNR_{LM}$( . . . ) coinciding with the tentatively assigned position ps. I.e. it is sufficient to compute the excess contrast-to-noise ratio vector $mCNR_{LM}$( . . . ) only in the neighborhood of the position ps, optionally taking into account a window of a low-pass filter. However, it can be advantageous to completely compute each excess contrast-to-noise ratio vector $mCNR_{LM}$( . . . ), so that subsequent operations can be easily performed in parallel using a vector processor.

It is noted that output of the zero crossing detection module 14 may comprise a set with a plurality of candidate border positions {pt}. A set of candidate border positions may comprise a first candidate border position where the scan trajectory crosses the border in the direction from the area in the image representing the healthy tissue to the area representing the tumor containing tissue and a second candidate border position where the scan trajectory crosses the border in the direction from the area representing the tumor containing tissue to the area in the image representing the healthy tissue. The set may be empty if the scan trajectory does not enter the area representing the non-healthy tissue. In some cases the border of the image area representing the tumor containing tissue and the image area representing the healthy tissue is concave. In these cases the zero crossing detection module 14 may identify a plurality of pairs of candidate border positions for a scan trajectory.

Figure 10A:
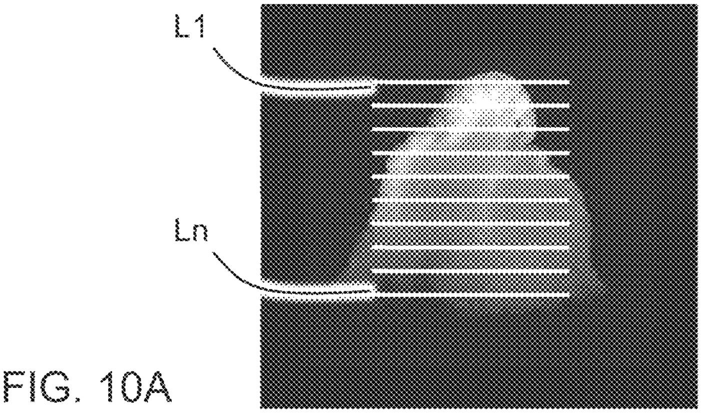
FIG. 10A, 10B, 10C illustrate aspects of a third data processing operation.

As shown in FIG. 10A, in operation the image inspection device 1 performs the above-mentioned procedure for a plurality of scan trajectories L1, . . . . Ln. A distance between the scan trajectories is typically related to the strip width as referred to above. The scan trajectories can be further apart if the width of the strip is larger. For example, the distance between the scan trajectories can be selected as equal to the strip width.

In some embodiments all scan trajectories are parallel. This complicates however the detection of a tissue border that extends in the same direction as the scan trajectories.

Figure 10B:
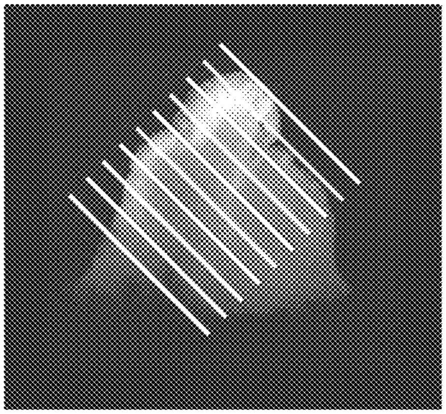
Figure 10C:
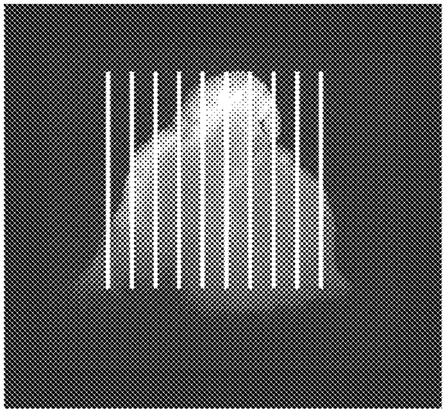

This can be avoided by performing the procedure with at least two sets of scan trajectories with a mutually different direction. In an example subsequent sets of scan trajectories have directions differing by 45 degrees. FIG. 10A, 10B, 10C show three of such sets. In another example the procedure is performed with two sets of scan trajectories in mutually orthogonal directions. In this case the choice of the directions x,y corresponds to the orientation of the principal axis in the fluorescence image, which is preferred for computational simplicity. Alternatively the procedure can be performed for a larger plurality of sets of scan trajectories, e.g. at angles of 0, 10, 20, . . . degrees with respect to a principle axis of the fluorescence image. It is possible to perform the procedure with an even larger set of scanning angles, for example with scanning angles that mutually differ by 1 degree. This is, however, not preferred, as it involves an additional computational burden and does not substantially contribute to performance in terms of accuracy. For practical purposes a difference of 10 degrees was found to be optimal.

The total number of pixels of the scan trajectories should cover at least a predetermined fraction of the total number of pixels in the foreground area.

If a scan trajectory represents a strip of pixels, the predetermined fraction can be relatively small.

Figure 11A:
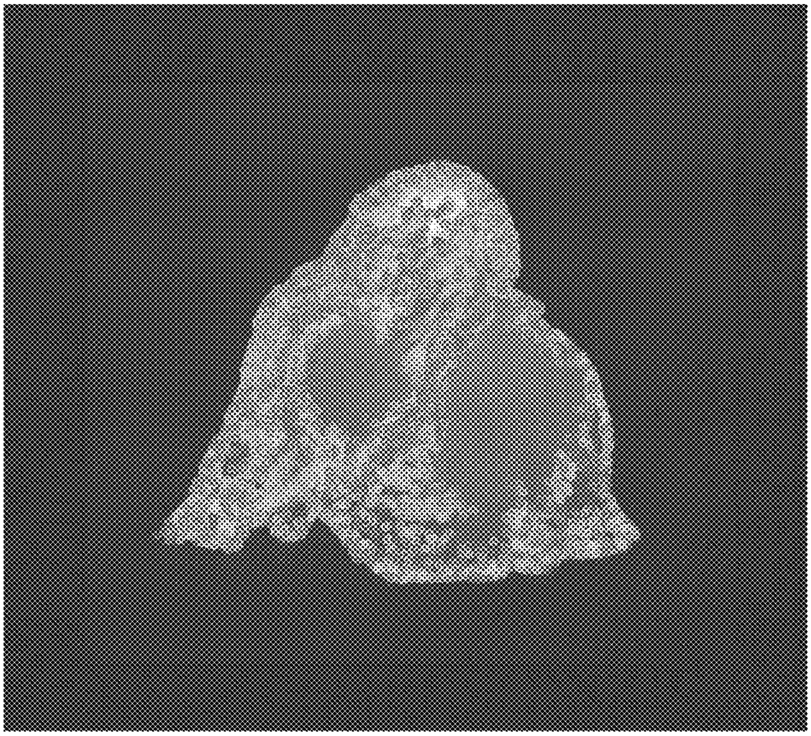
FIGS. 11A and 11B illustrate results of variations of a fourth data processing operation.
Figure 11B:
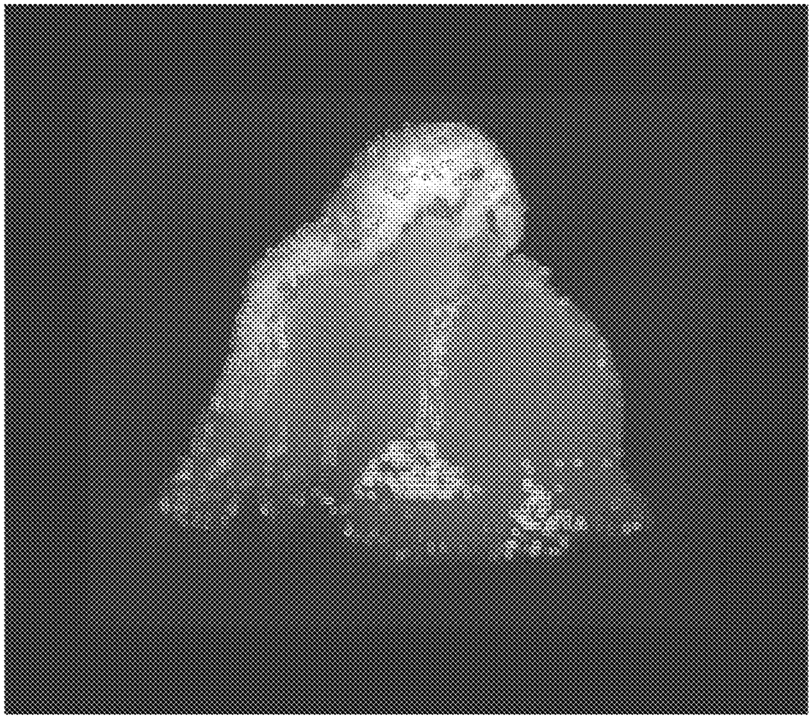

The zero crossing detection module 14 repeats the zero-crossing estimation procedure for all scan trajectories resulting in a plurality of candidate border positions of a border between healthy and non-healthy tissue. FIG. 11A shows the candidate border positions superposed on the original fluorescence image FI obtained with 36 sets of scan trajectories having angles differing by 10 degrees. FIG. 11B shows an alternative result obtained with 4 sets of scan trajectories having angles differing by 90 degrees. Based on the set of candidate border positions obtained from the zero crossing detection module 14, the border indication module 15 generates an indication of the border between the area in the image that represents the tumor tissue and the area with the healthy tissue.

Figure 12A:
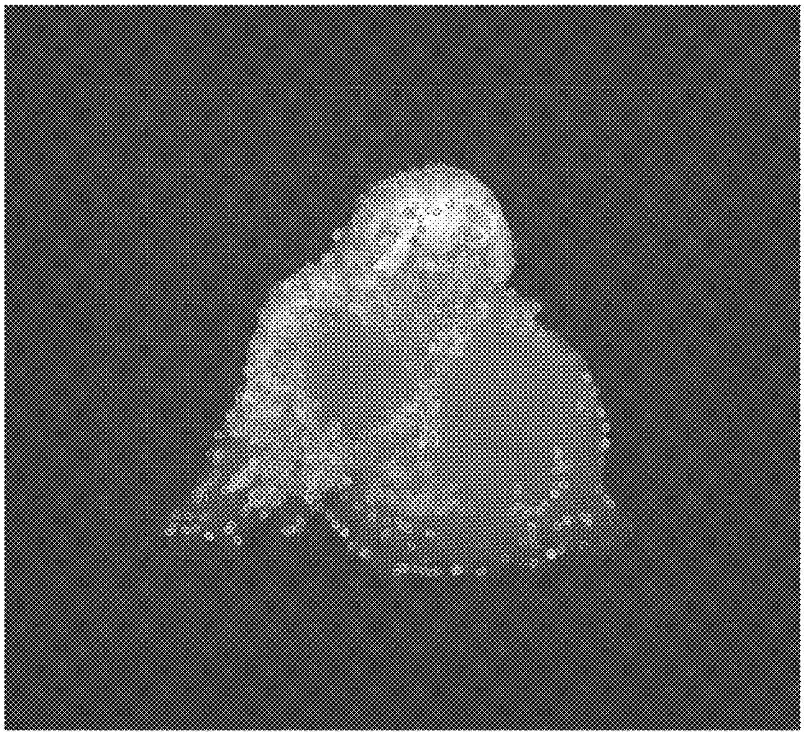
FIGS. 12A and 12B illustrate results of variations of a fifth data processing operation.
Figure 12B:
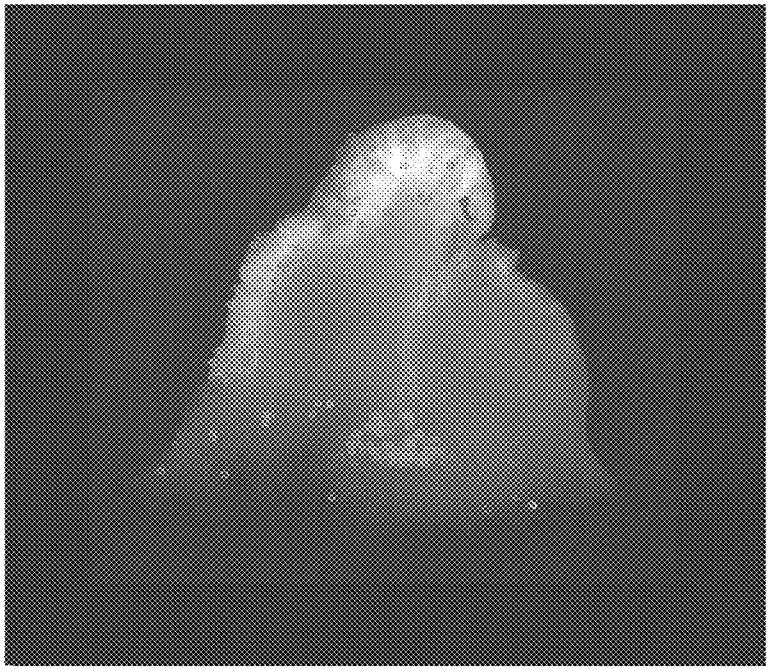

In an example the border indication module 15 compares candidate border positions of respective scan trajectories with candidate border positions of respective overlapping scan trajectories that extend in the opposite direction. In this example the border indication module 15 determines which candidate border positions of a first scan trajectory match with a candidate border position of the overlapping oppositely directed scan trajectory. A pair of candidate border positions is determined as matching if they coincide or are close to each other, that is their Euclidean distance is at most a distance threshold value, e.g. a value selected from the range of 1 to 10. Best results were obtained with a value in the range of 2-5. In case the mutually overlapping oppositely directed scan trajectories extend along a main coordinate axis x,y of the image the Euclidian distance measure reduces to the absolute difference between the coordinate values of the candidate border positions to be compared. In an implementation the border indication module 15 then eliminates those candidate border positions that do not have a matching candidate border position in the overlapping oppositely directed scan trajectory. Exemplary results of this operation are shown in FIG. 12A and FIG. 12B. FIG. 12A shows the result of the elimination procedure applied to the set of candidate border positions as shown in FIG. 11A obtained with the 36 sets of scan trajectories having angles differing by 10 degrees. FIG. 12B shows the result of the elimination procedure applied to the set of candidate border positions as shown in FIG. 11B obtained with the 4 sets of scan trajectories having angles differing by 90 degrees.

Figure 13A:
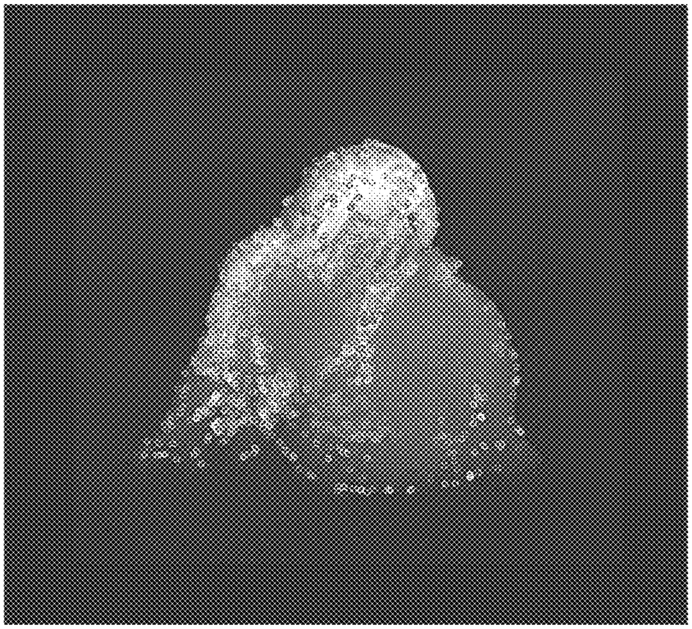
FIGS. 13A and 13B illustrate results of variations of a fifth data processing operation.
Figure 13B:
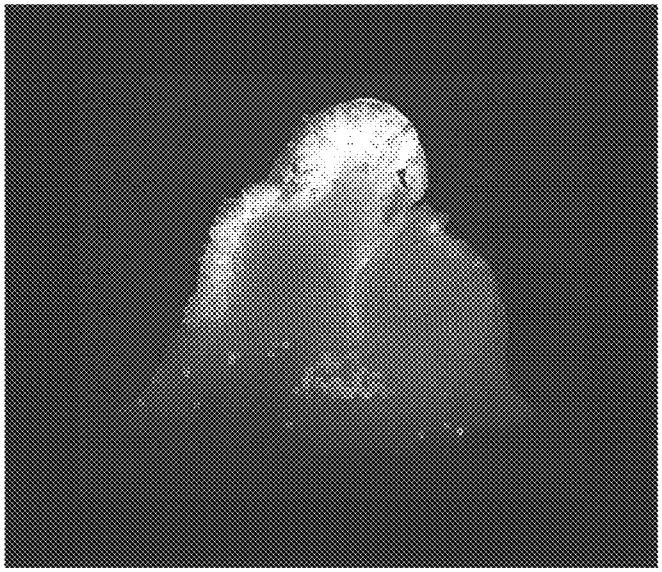

A further implementation of the border indication module 15 of this example also performs a merging operation. That is, if it detects a pair of candidate border positions obtained from a pair of mutually overlapping oppositely directed scan trajectories that do not coincide but that are close enough to comply with the distance threshold then it replaces the pair of candidate border positions with a single candidate border position having a position centered between the two original candidate border positions. Results of this operation are shown in FIG. 13A wherein the merging step is applied to the set of remaining candidate border positions as shown in FIG. 12A. Likewise FIG. 13B illustrates the results of the merging step applied to the set of remaining candidate border positions as shown in FIG. 12B.

In a variation the original candidate border positions are associated with a confidence indication. The confidence indication is based for example on the magnitude of the gradient found for the gradient of the fluorescence signal vector $F_L(\ldots)$ of the scan trajectory with which the original candidate border position was obtained. A higher magnitude of the gradient is indicative for a higher confidence of the location of the border position. In an example the single candidate border position is located closer to the original candidate border position having the highest confidence indication.

Figure 14:
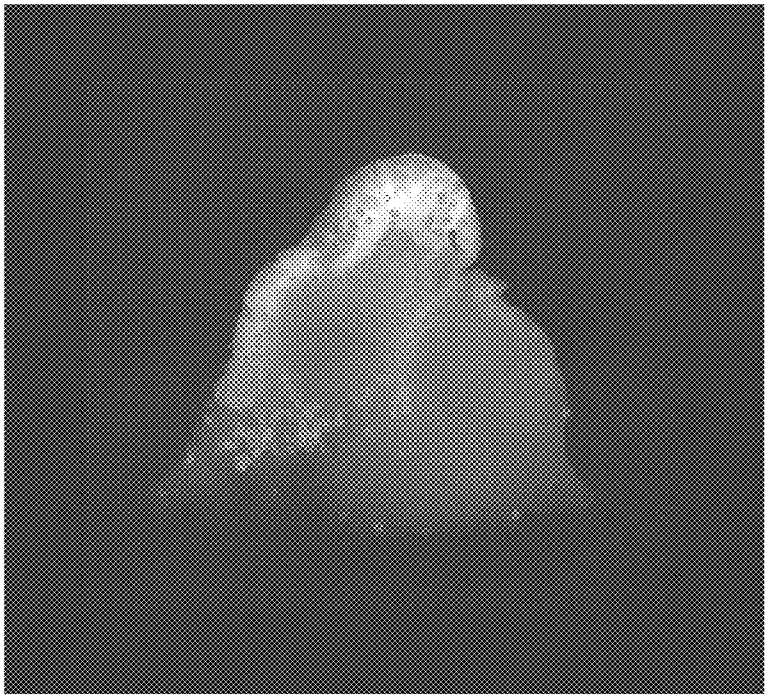
FIG. 14 shows results of a sixth data processing operation.

In an embodiment, the border indication module 15 performs an operation to eliminate isolated candidate border positions. In this embodiment the border indication module 15 identifies a candidate border position as an isolated candidate border position if there is no other candidate border position in the complete set of candidate border positions within a predetermined distance from that candidate border position. The predetermined distance may be the same as the predetermined distance in the previously mentioned operation wherein it is determined whether or not a candidate border position obtained with a scan trajectory matches a candidate border position of an overlapping scan trajectory in the opposite direction. Exemplary results of this elimination operation are shown in FIG. 14. In this example the elimination operation is applied to the set of remaining candidate border positions as shown in FIG. 13A.

Figure 15:
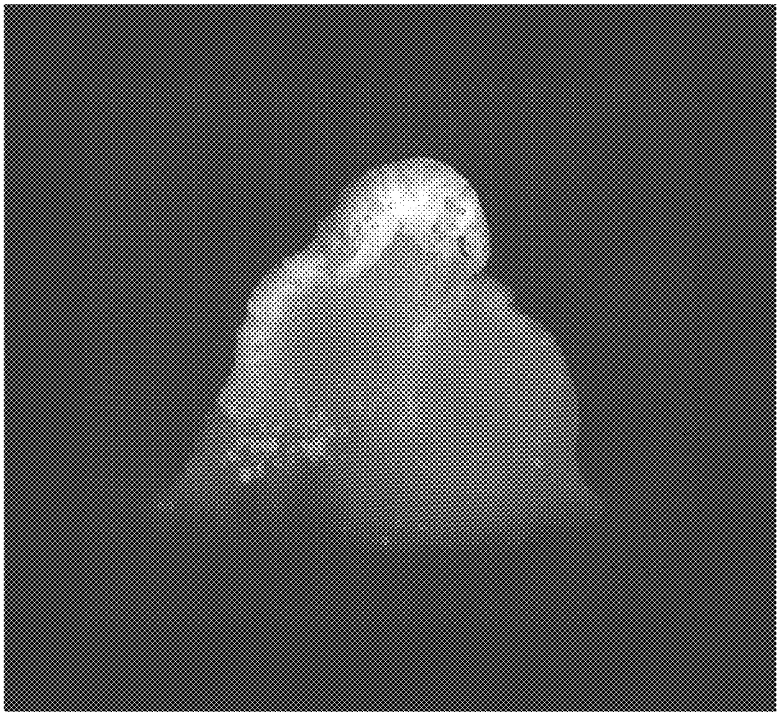
FIG. 15 shows results of a seventh data processing operation.

In an embodiment the border indication module 15 performs an operation wherein it merges respective pairs of candidate border positions that are within a threshold distance from each other into a respective single candidate border position. Contrary to the merging procedure described for merging pairs of candidate border positions obtained from mutually overlapping oppositely directed scan trajectories, the present merging procedure is applied to any pair of candidate border positions in the available set of candidate border positions that are within the specified threshold distance for this operation. The specified threshold distance for this operation may also be selected from a range of 2-5. FIG. 15 show exemplary results for the case wherein the merging operation is applied to the sets of candidate border positions shown in FIG. 14. In this example the merging operation is applied once, but alternatively this operation is repeated a predetermined number of times or is repeated until a stop criterion is complied with, e.g. a criterion that the number of candidate border positions is reduced to a specified threshold number. In practice it was found that a one time merging step is sufficient. In order to reduce computational effort while maintaining acceptable results the merging operation may be skipped. Considering this, also the merging operation described with reference to FIG. 13A, 13B may be skipped.

Subsequently a border is constructed in the fluorescence image based on the set of candidate border positions obtained for the respective scan trajectories. This border is indicative for a margin in the tissue between the tumor and the healthy part of the tissue.

In an embodiment the constructed border is a primary curve that interconnects the peripheral candidate border positions. The primary curve in the fluorescence image is to indicate the edge of the high fluorescence area itself. In an example wherein the fluorescence image is obtained from a tumor containing tissue that has been rendered fluorescent with a sufficiently specific tracer, the edge of the high fluorescent area is likely to coincide with the margin of the tumor.

In another embodiment the border is constructed as a secondary curve that encloses a primary curve that interconnects the peripheral transition positions, and that extends at a distance outside the primary curve dependent on the type of tumor present in the tissue. The secondary curve indicates a region that should be treated or be excised. Typically this secondary curve encloses the primary curve at a predetermined distance outside the primary curve dependent on the type of tumor tissue. In an embodiment locally the distance between the secondary curve and the primary curve is smaller than the predetermined distance, so as to avoid an intersection of a specified anatomical structure.

Figure 16:
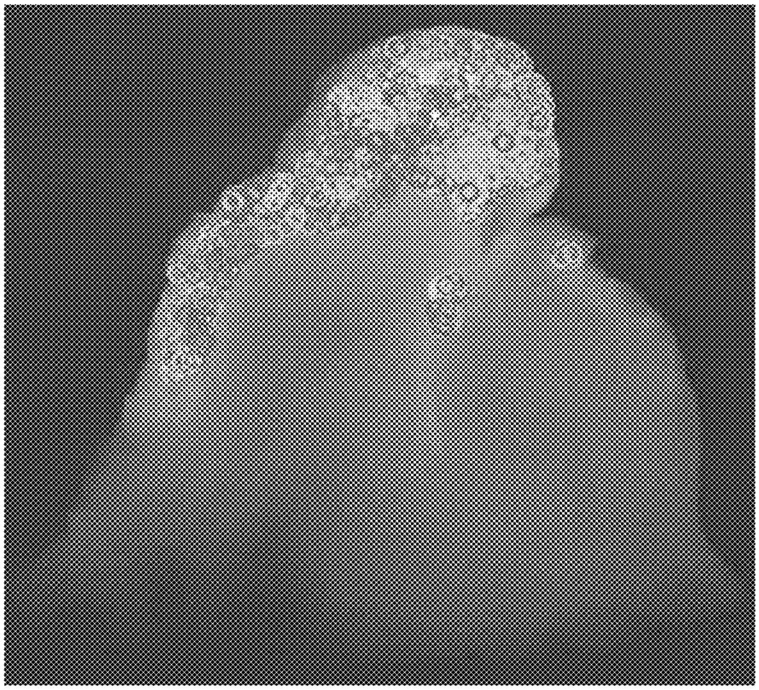
FIG. 16 shows results of an eighth data processing operation.
Figure 17:
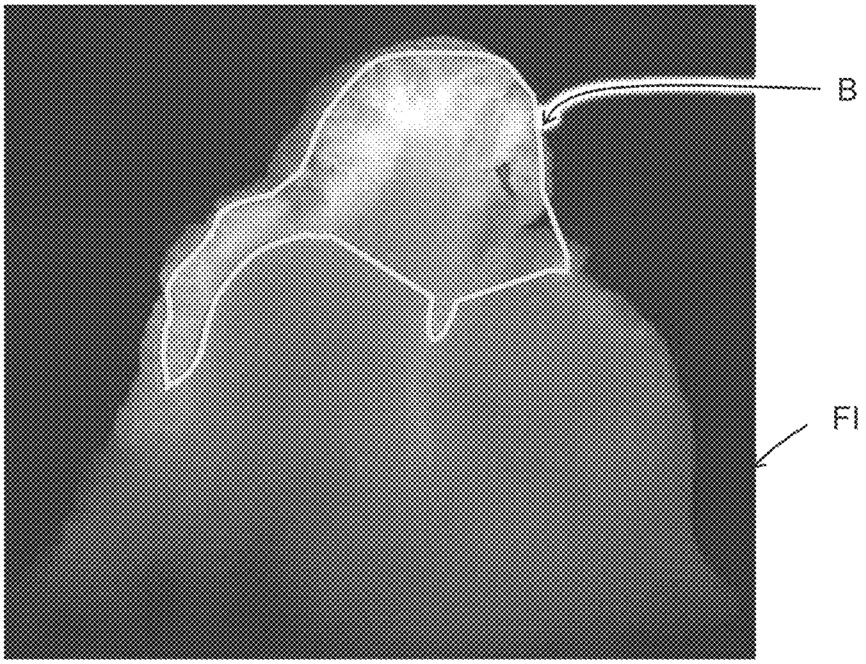
FIG. 17 shows an indication of a border superposed on the fluorescence image of FIG. 7A.

FIG. 17 shows an example of a border B constructed in the fluorescence image FI wherein the border construction section 155 directly constructs a border from a set $\{pt\}^a$ (see FIG. 16) of candidate border positions retrieved from candidate border position filter section 150. The border construction section 155 therewith applied the MatLab function boundary (x,y,s) with s=0.5 to a filtered set $\{pt\}^a$ (see FIG. 16) of candidate border positions retrieved from candidate border position filter section 150. This function constructs a boundary that interconnects the peripheral candidate border positions. The shape of the constructed boundary is intermediate between a shape that tightly follows all peripheral candidate border positions and a convex hull around the peripheral candidate border positions.

Example II

Figure 18A:
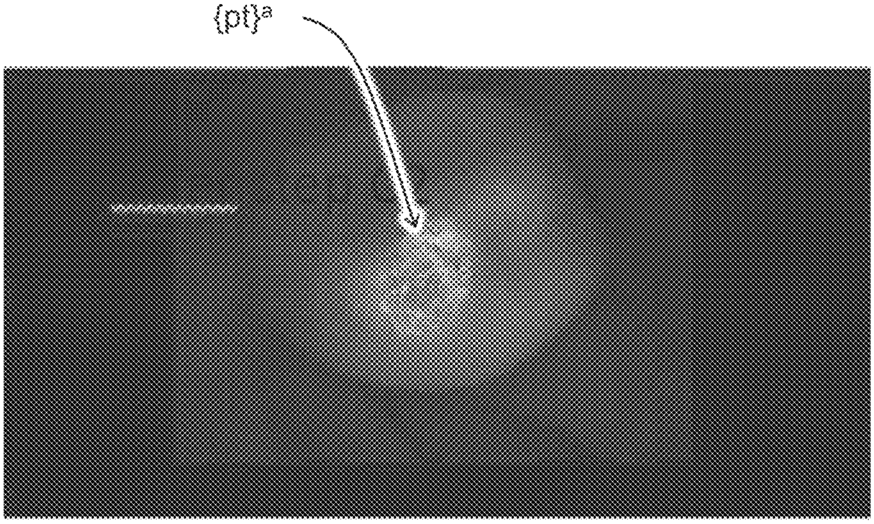
FIG. 18A-18F show first exemplary results derived with a fluorescence image obtained in-vivo from tissue of a patient.
Figure 18B:
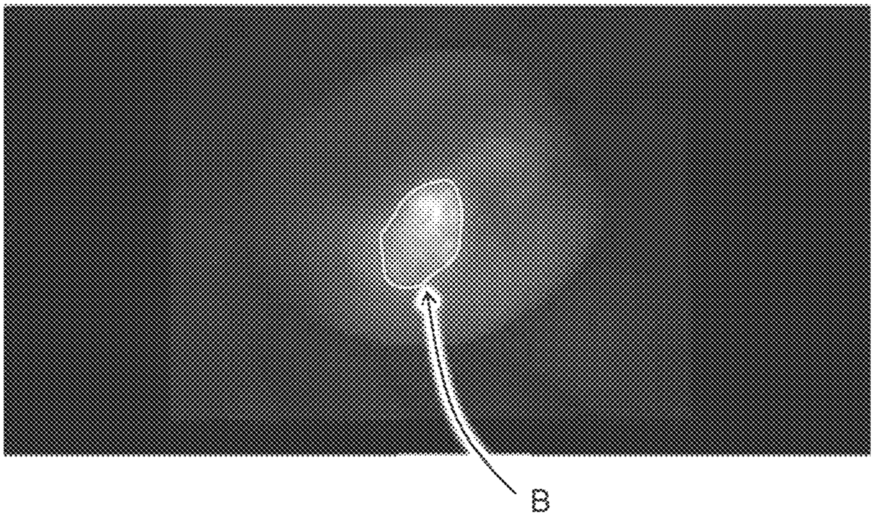
Figure 18C:
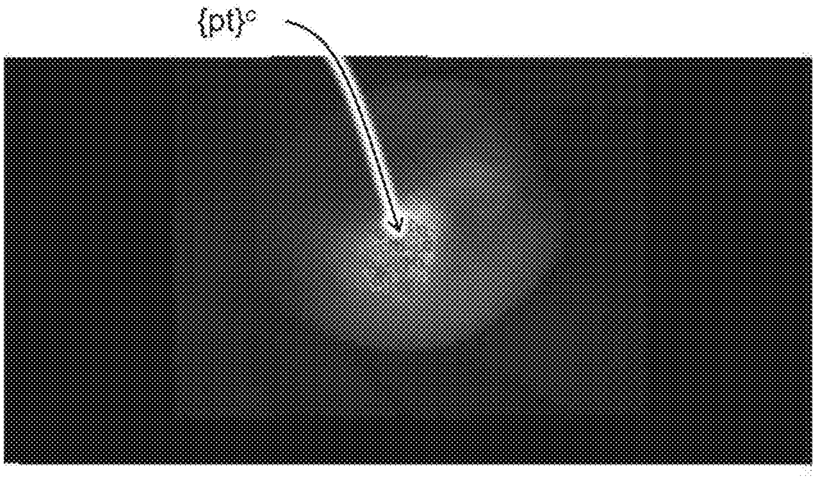
Figure 18D:
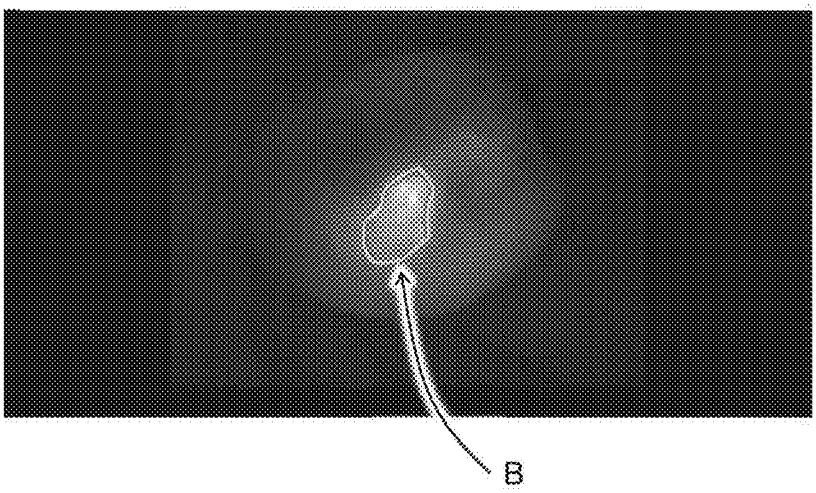
Figure 18E:
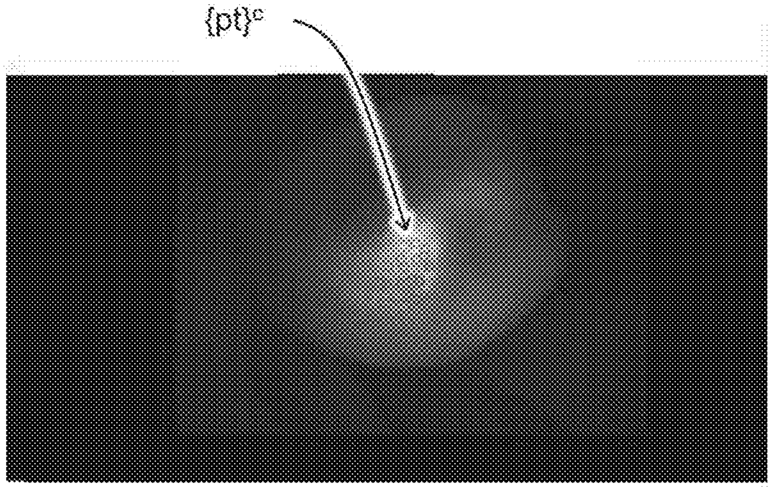
Figure 18F:
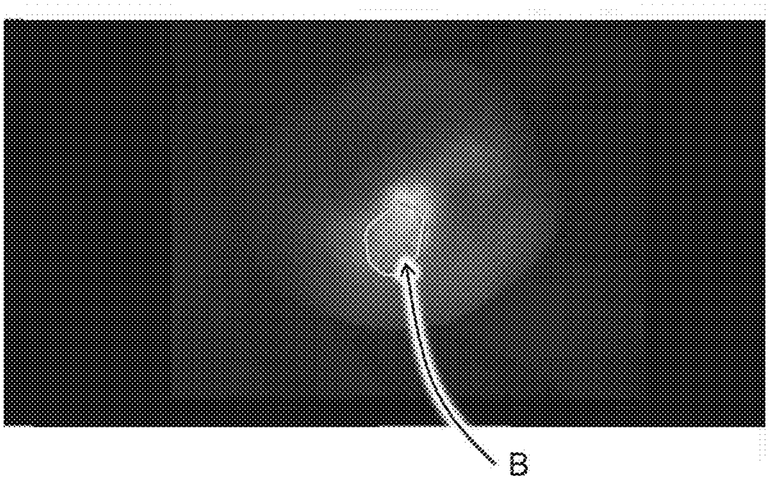

FIG. 18A, . . . , FIG. 18F show exemplary results obtained for a fluorescence image obtained in-vivo from tissue of a patient. In this case the tissue comprised a penile squamous cell carcinoma and the tissue was rendered fluorescent with the tracer Cetuximab-IRDye800CW.

FIG. 18A shows the filtered set $\{pt\}''$ of candidate border positions as output by the candidate border position filter section 150 superposed on the original fluorescence image FI.

FIG. 18B shows superposed on the fluorescence image a border B directly constructed from the filtered set $\{pt\}^a$ of candidate border positions retrieved from candidate border position filter section 150.

FIG. 18C shows, superposed on the fluorescence image a set $\{pt\}^c$ of candidate border positions retrieved from further candidate border position matching section 152.

FIG. 18D shows superposed on the fluorescence image a border B constructed from set $\{pt\}^c$ of candidate border positions shown in FIG. 18C.

FIG. 18E shows, superposed on the fluorescence image a set $\{pt\}''$ of candidate border positions retrieved from the candidate border position merging section 153.

FIG. 18F shows superposed on the fluorescence image a border B constructed from set $\{pt\}''$ of candidate border positions shown in FIG. 18E.

Figure 19A:
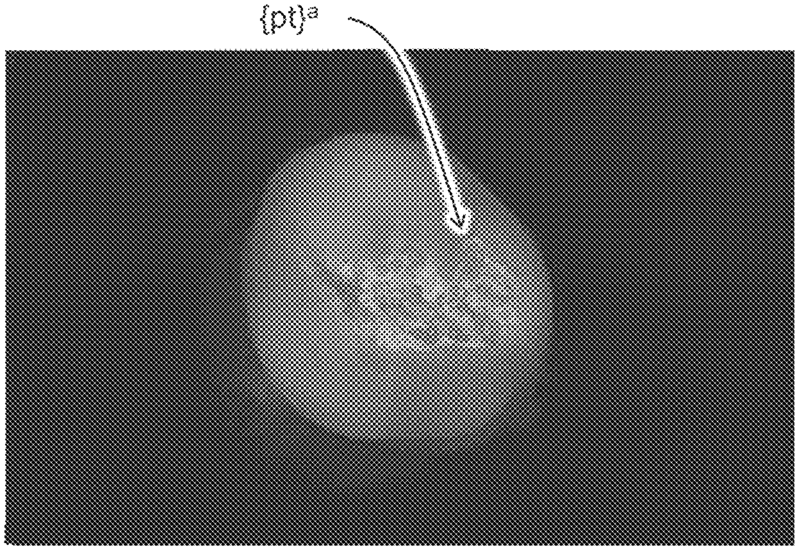
FIG. 19A-19F show second exemplary results derived with a fluorescence image obtained from said tissue after ex-vivo after it was completely resected from the patient.
Figure 19B:
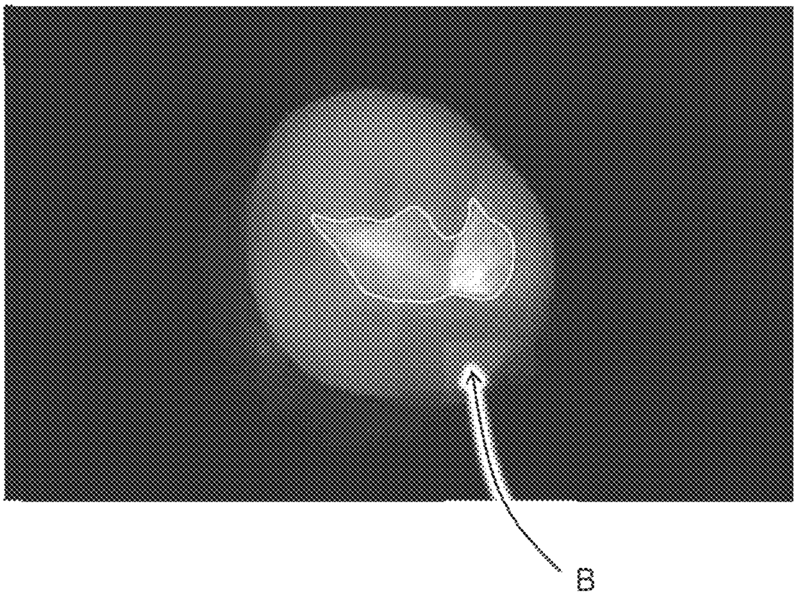
Figure 19C:
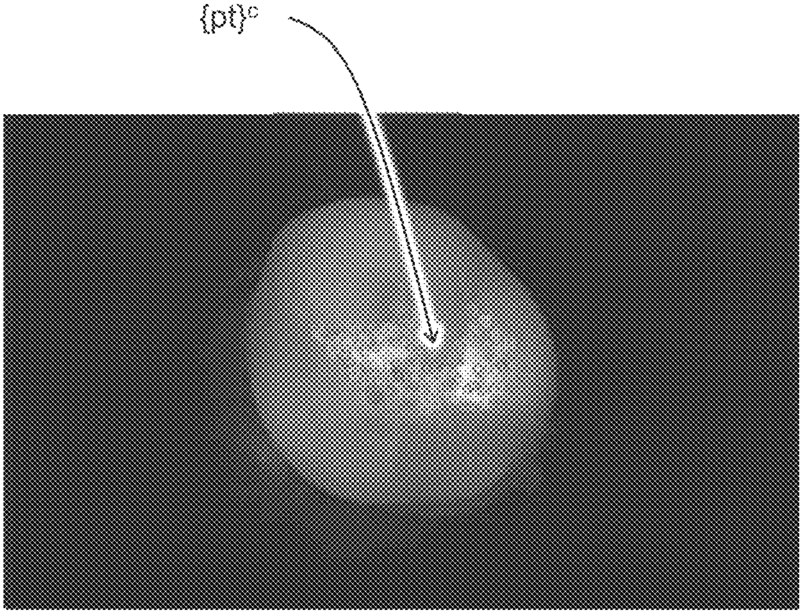
Figure 19D:
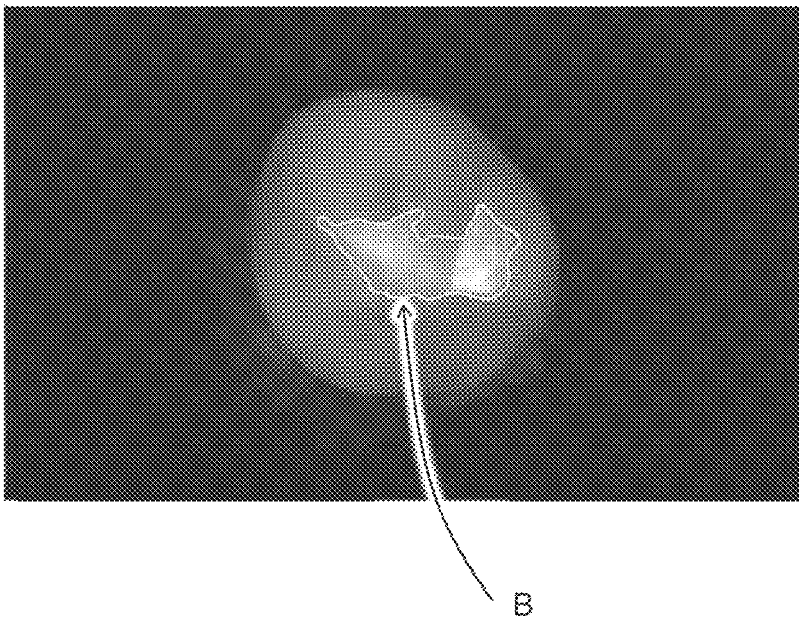
Figure 19E:
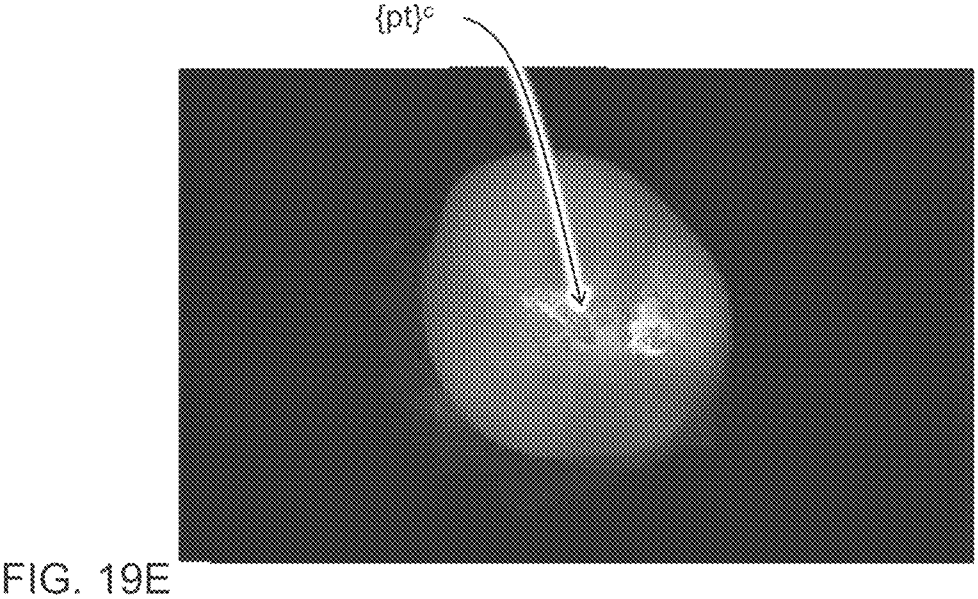
Figure 19F:
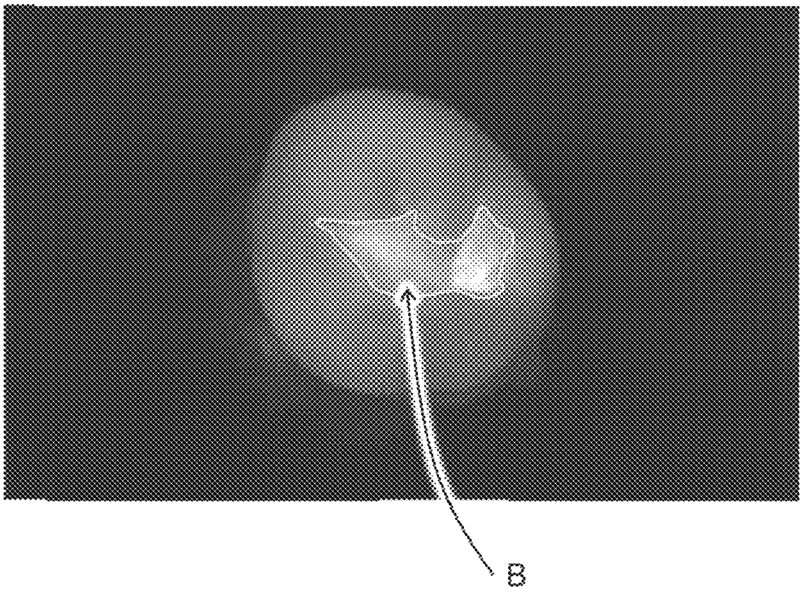

FIG. 19A, . . . , FIG. 19F show further exemplary results obtained for a fluorescence image obtained ex-vivo from the complete tissue resected from the patient.

FIG. 19A shows the filtered set $\{pt\}^a$ of candidate border positions as output by the candidate border position filter section 150 superposed on the original fluorescence image FI. FIG. 19B shows superposed on the fluorescence image a border B directly constructed from the filtered set $\{pt\}^a$ of candidate border positions retrieved from candidate border position filter section 150.

FIG. 19C shows, superposed on the fluorescence image a set $\{pt\}^c$ of candidate border positions retrieved from further candidate border position matching section 152.

FIG. 19D shows superposed on the fluorescence image a border B constructed from set $\{pt\}^c$ of candidate border positions shown in FIG. 19C.

FIG. 19E shows, superposed on the fluorescence image a set $\{pt\}''$ of candidate border positions retrieved from the candidate border position merging section 153.

FIG. 19F shows superposed on the fluorescence image a border B constructed from set $\{pt\}''$ of candidate border positions shown in FIG. 19E.

Figure 20A:
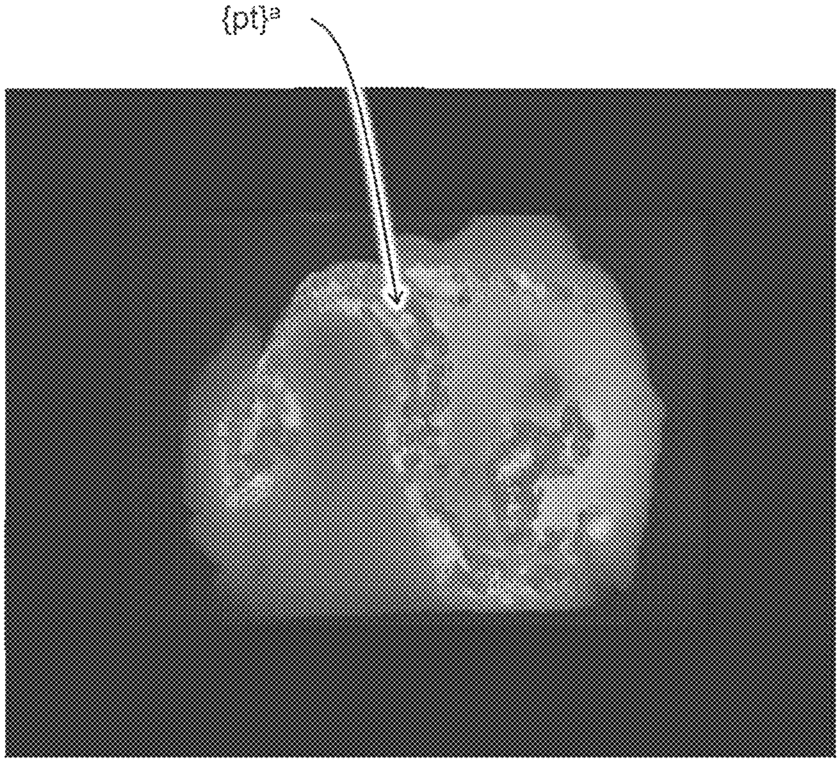
FIG. 20A-20F show third exemplary results derived from a fluorescence image obtained ex-vivo from a slice of said resected tissue.
Figure 20B:
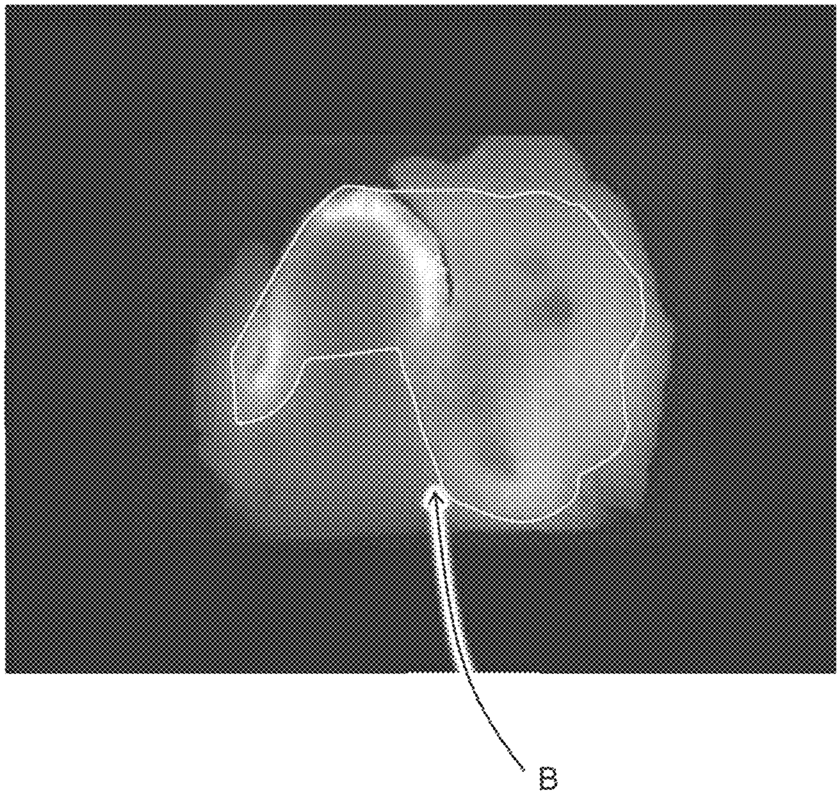
Figure 20C:
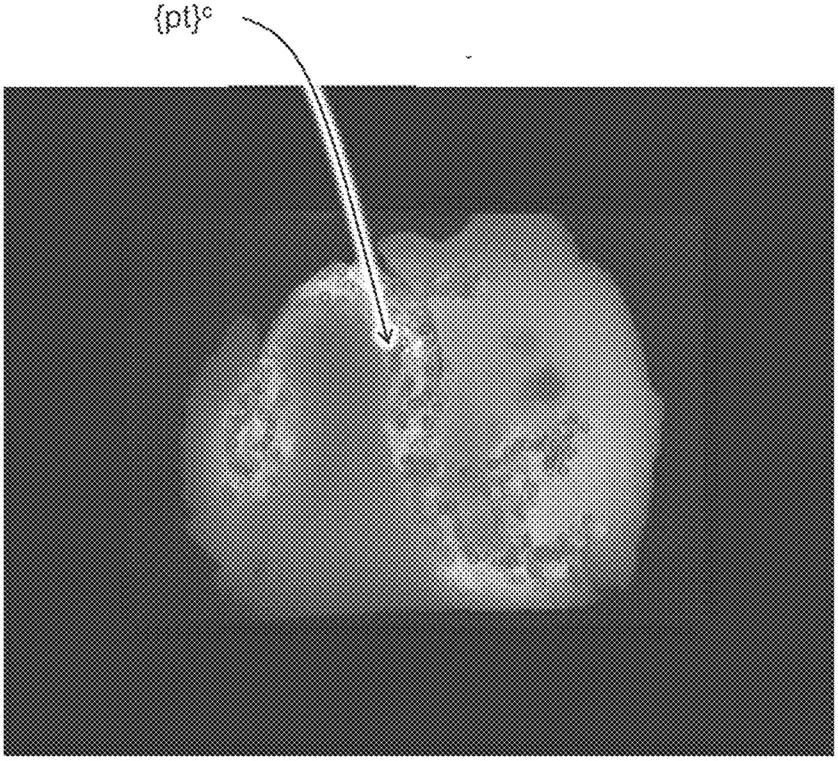
Figure 20D:
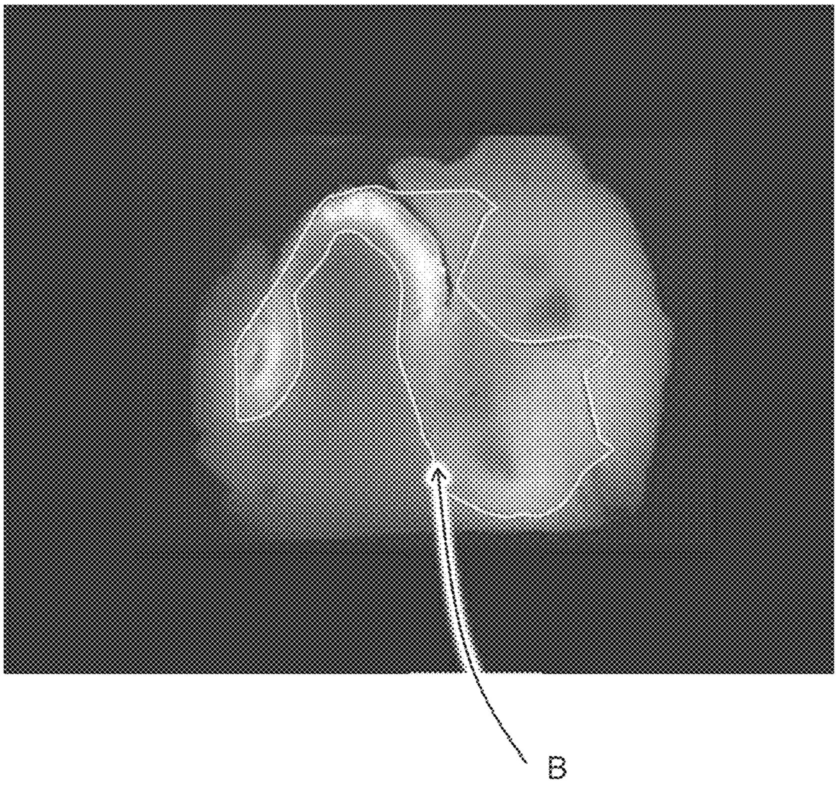
Figure 20E:
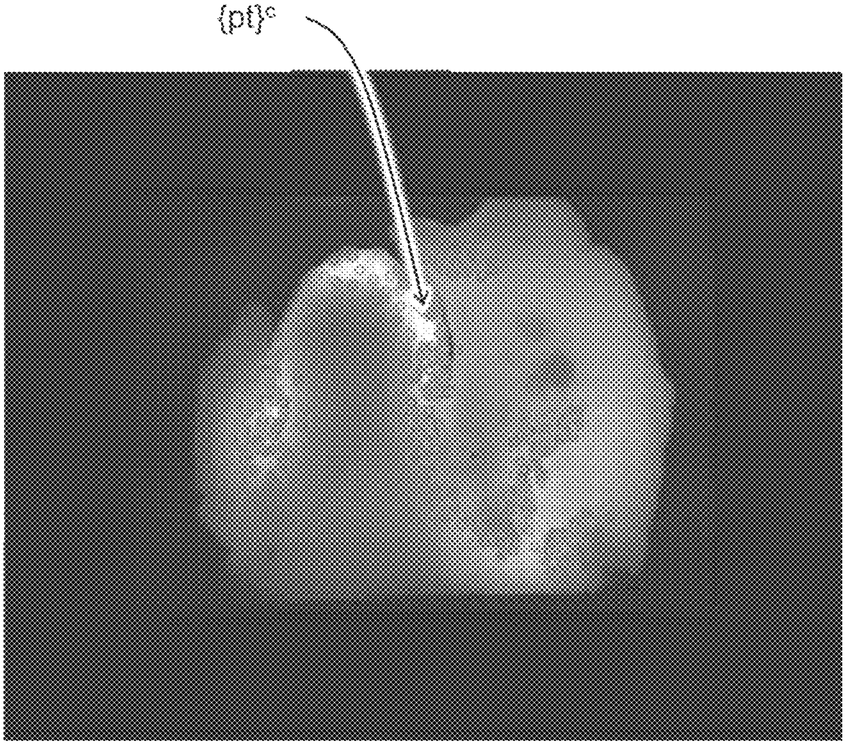
Figure 20F:
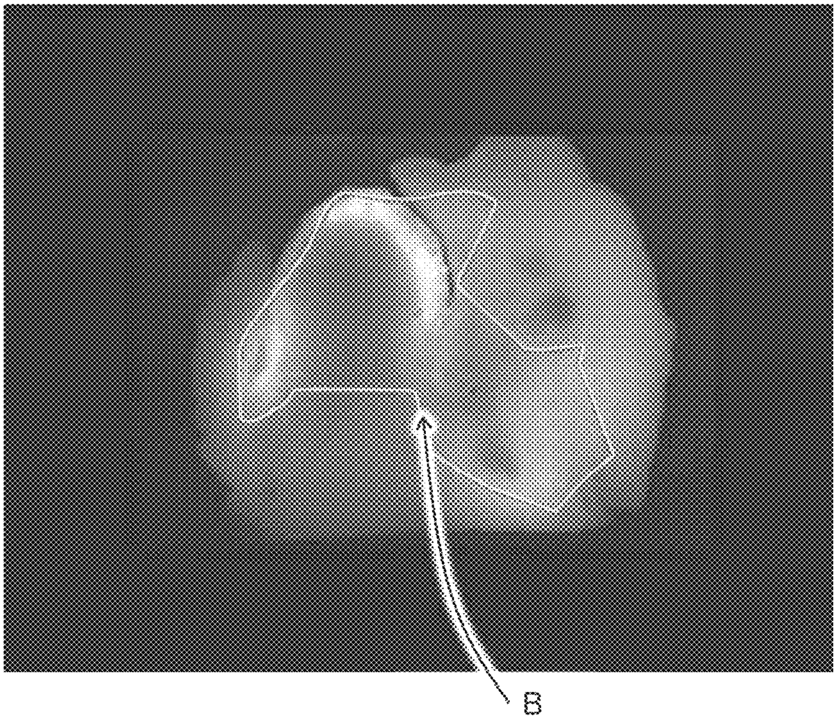

FIG. 20A, . . . , FIG. 20F show further exemplary results obtained for a fluorescence image obtained ex-vivo from a slice of the resected tissue.

FIG. 20A shows the filtered set $\{pt\}^a$ of candidate border positions as output by the candidate border position filter section 150 superposed on the original fluorescence image FI.

FIG. 20B shows superposed on the fluorescence image a border B directly constructed from the filtered set $\{pt\}^a$ of candidate border positions retrieved from candidate border position filter section 150.

FIG. 20C shows, superposed on the fluorescence image a set $\{pt\}^c$ of candidate border positions retrieved from further candidate border position matching section 152.

FIG. 20D shows superposed on the fluorescence image a border B constructed from set $\{pt\}^c$ of candidate border positions shown in FIG. 20C.

FIG. 20E shows, superposed on the fluorescence image a set $\{pt\}''$ of candidate border positions retrieved from the candidate border position merging section 153.

FIG. 20F shows superposed on the fluorescence image a border B constructed from set $\{pt\}''$ of candidate border positions shown in FIG. 20E.

From the exemplary results presented in this example, it was concluded that the border B constructed from the filtered set $\{pt\}^a$ of candidate border positions best matched the margin of the tumor indicated by a pathologist. For example for the fluorescence image obtained in-vivo the border constructed as shown in FIG. 18B provides the best correspondence with analysis of a pathologist.

Example III

Figure 21A:
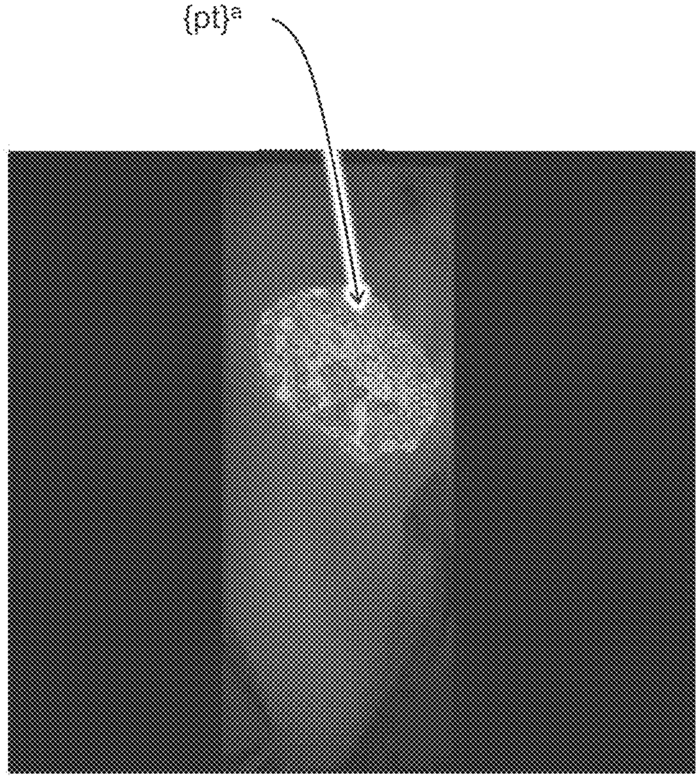
FIG. 21A-21F show fourth exemplary results derived with a fluorescence image obtained in-vivo from tissue of a further patient.
Figure 21B:
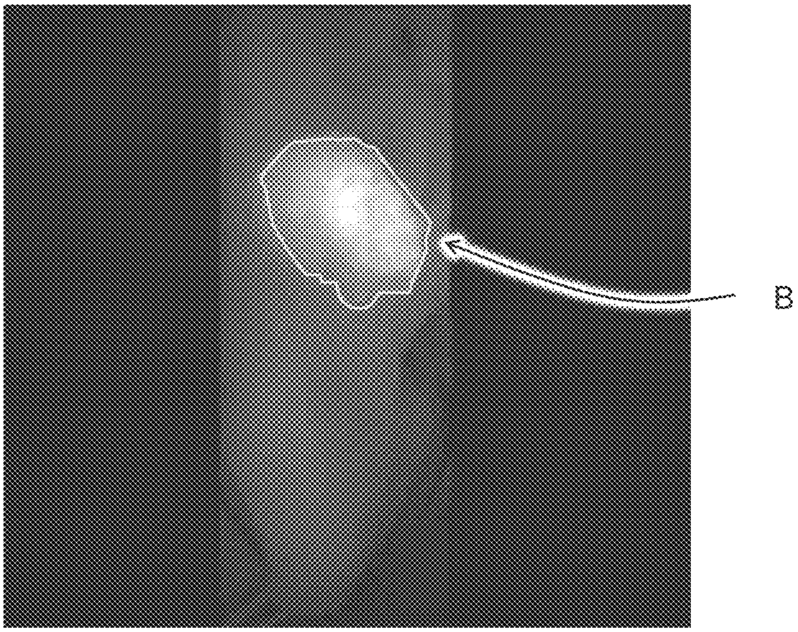
Figure 21C:
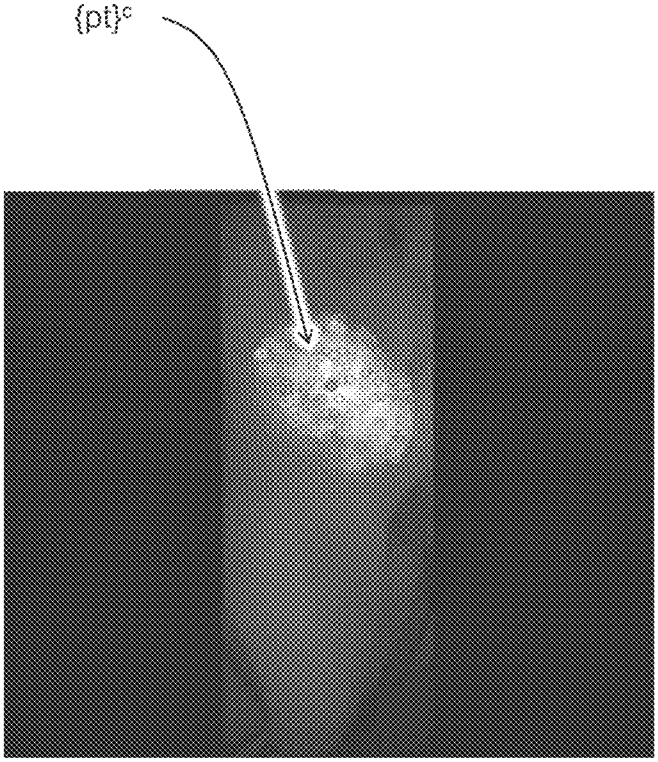
Figure 21D:
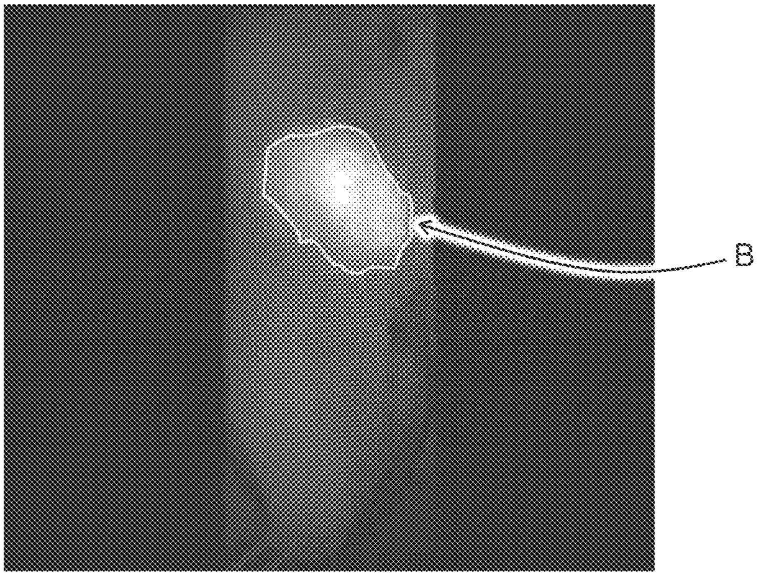
Figure 21E:
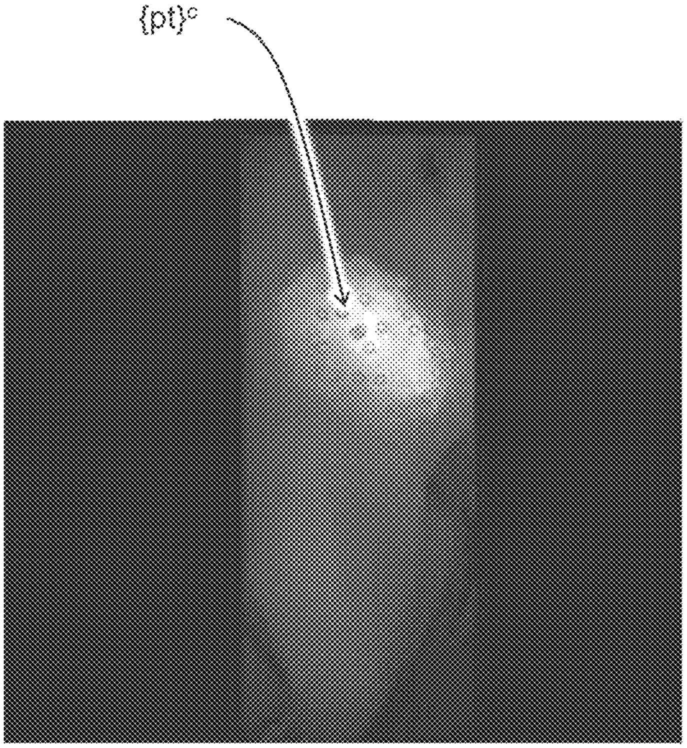
Figure 21F:
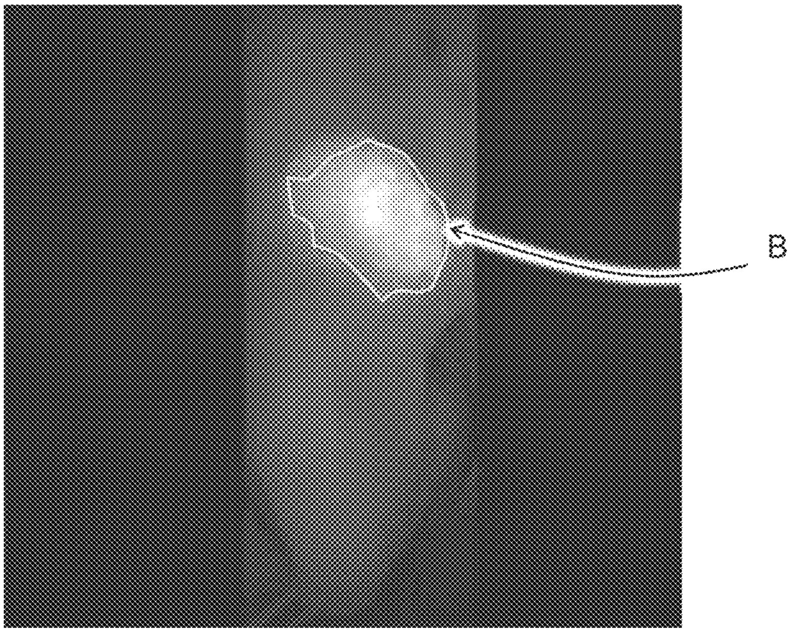

FIG. 21A, . . . , FIG. 21F show exemplary results obtained for a fluorescence image obtained in-vivo from tissue of a patient comprising a head and neck squamous cell carcinoma rendered fluorescent with the tracer Cetuximab-IRDye800CW.

FIG. 21A shows the filtered set $\{pt\}^a$ of candidate border positions as output by the candidate border position filter section 150 superposed on the original fluorescence image FI.

FIG. 21B shows superposed on the fluorescence image a border B directly constructed from the filtered set $\{pt\}^a$ of candidate border positions retrieved from candidate border position filter section 150.

FIG. 21C shows, superposed on the fluorescence image a set $\{pt\}^c$ of candidate border positions retrieved from further candidate border position matching section 152.

FIG. 21D shows superposed on the fluorescence image a border B constructed from set $\{pt\}^c$ of candidate border positions shown in FIG. 21C.

FIG. 21E shows, superposed on the fluorescence image a set $\{pt\}^n$ of candidate border positions retrieved from the candidate border position merging section 153.

FIG. 21F shows superposed on the fluorescence image a border B constructed from set $\{pt\}^n$ of candidate border positions shown in FIG. 21E.

Figure 22A:
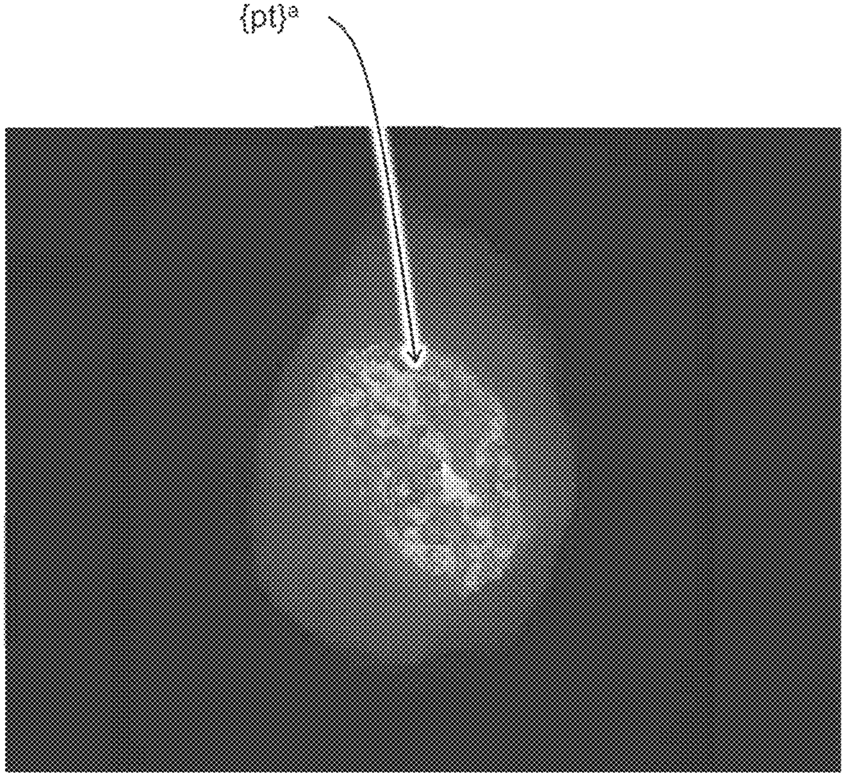
FIG. 22A-22F show fifth exemplary results derived with a fluorescence image obtained ex-vivo from the complete tissue resected from the patient.
Figure 22B:
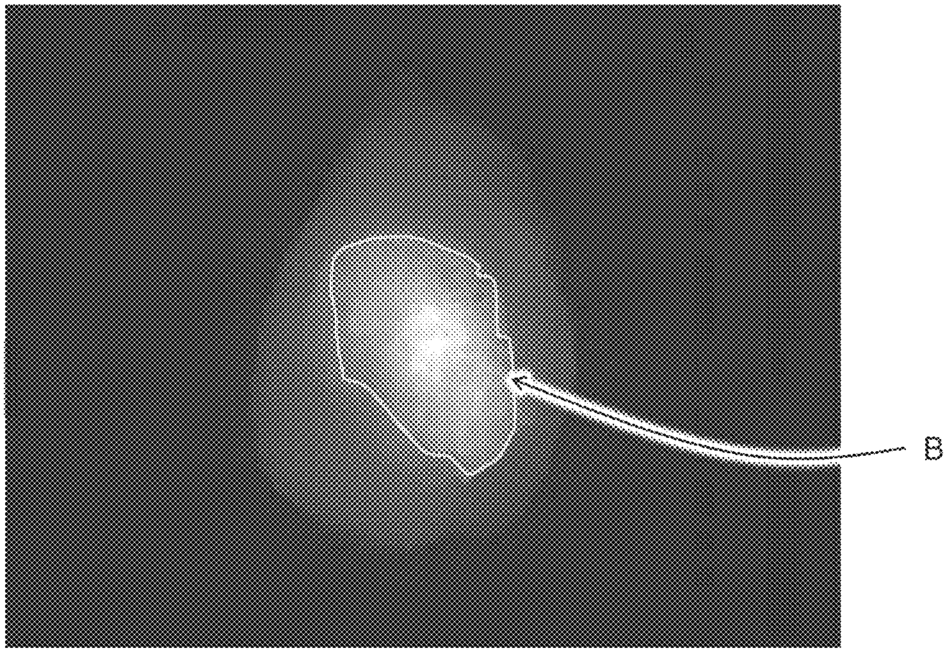
Figure 22C:
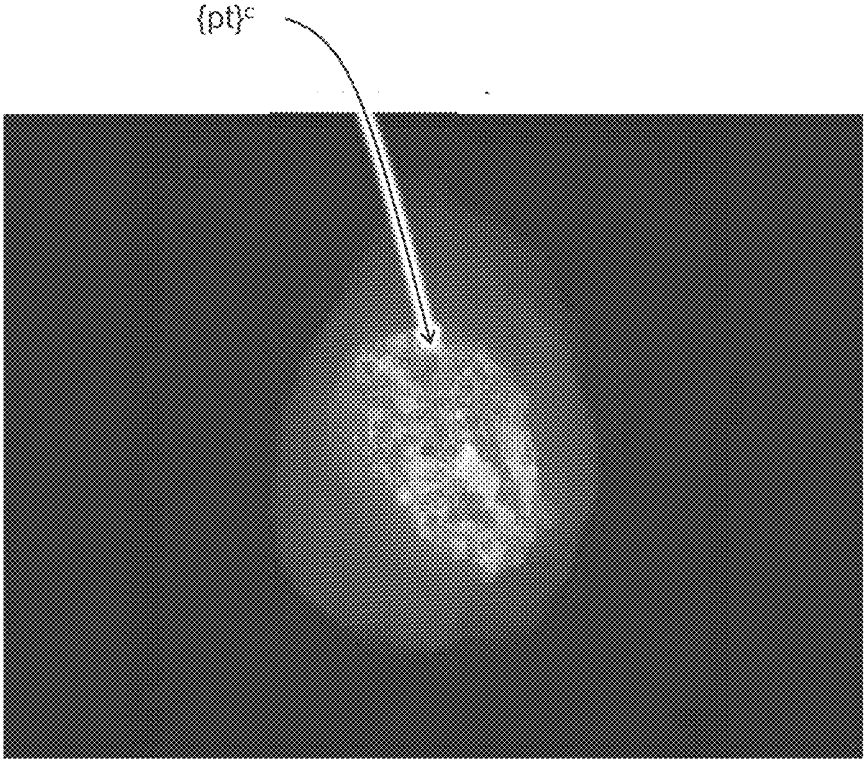
Figure 22D:
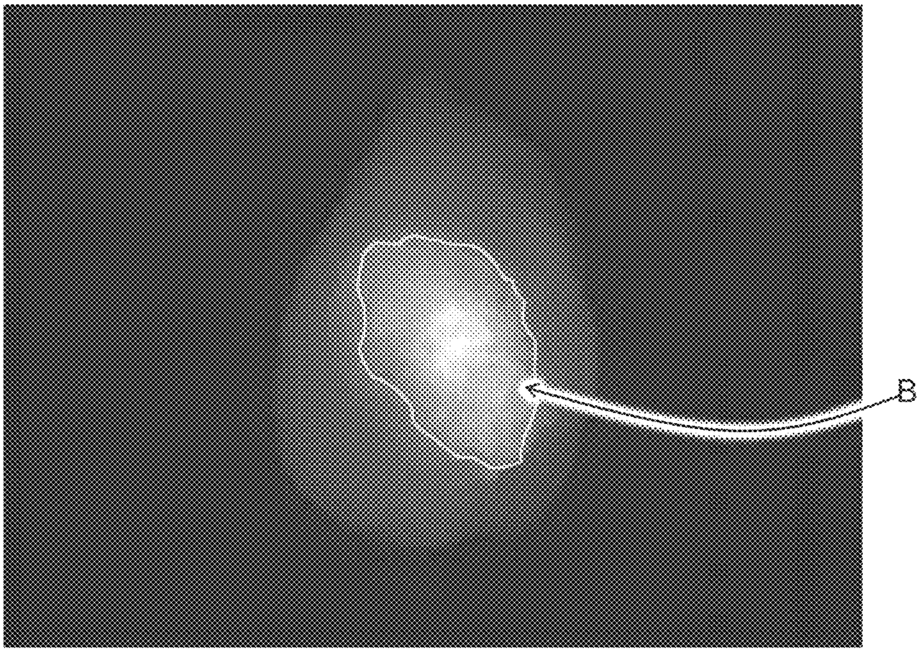
Figure 22E:
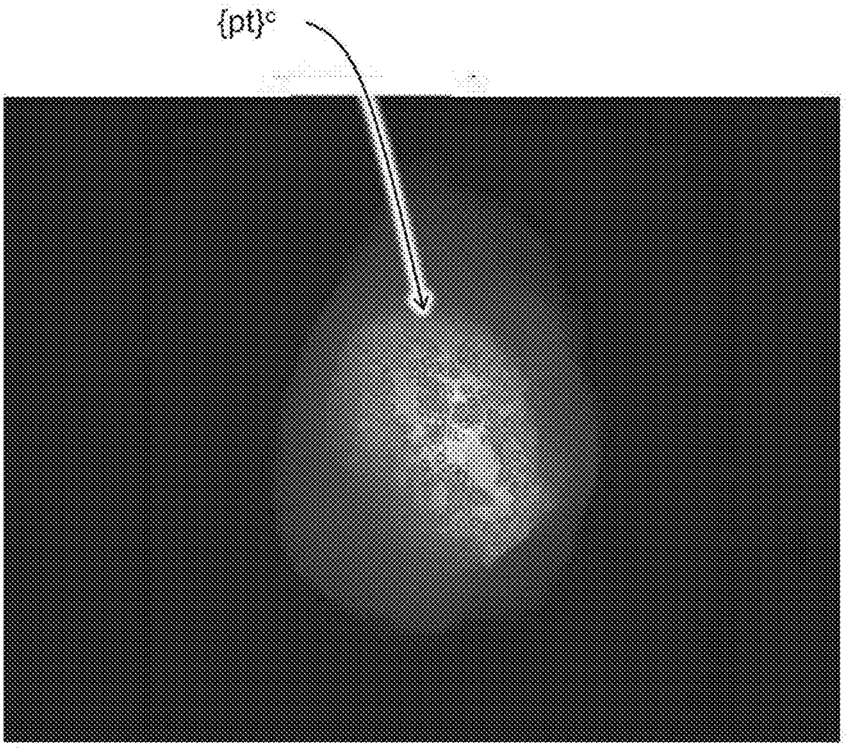
Figure 22F:
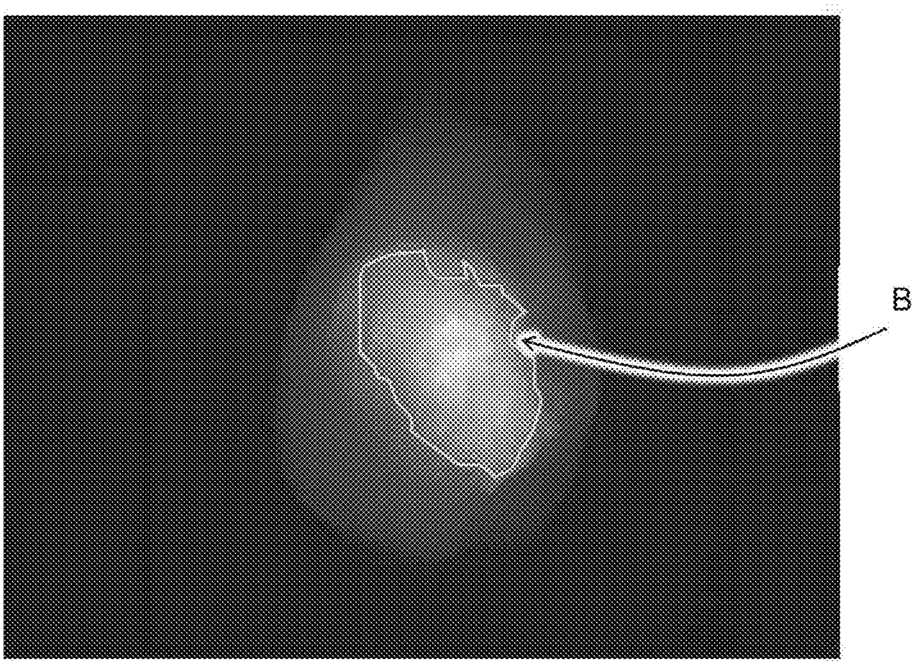

FIG. 22A, . . . , FIG. 22F show further exemplary results obtained for a fluorescence image obtained ex-vivo from the complete tissue resected from the patient.

FIG. 22A shows the filtered set $\{pt\}^a$ of candidate border positions as output by the candidate border position filter section 150 superposed on the original fluorescence image FI.

FIG. 22B shows superposed on the fluorescence image a border B directly constructed from the filtered set $\{pt\}^a$ of candidate border positions retrieved from candidate border position filter section 150.

FIG. 22C shows, superposed on the fluorescence image a set $\{pt\}^c$ of candidate border positions retrieved from further candidate border position matching section 152.

FIG. 22D shows superposed on the fluorescence image a border B constructed from set $\{pt\}^c$ of candidate border positions shown in FIG. 22C.

FIG. 22E shows, superposed on the fluorescence image a set $\{pt\}^n$ of candidate border positions retrieved from the candidate border position merging section 153.

FIG. 22F shows superposed on the fluorescence image a border B constructed from set $\{pt\}^n$ of candidate border positions shown in FIG. 22E.

Figure 23A:
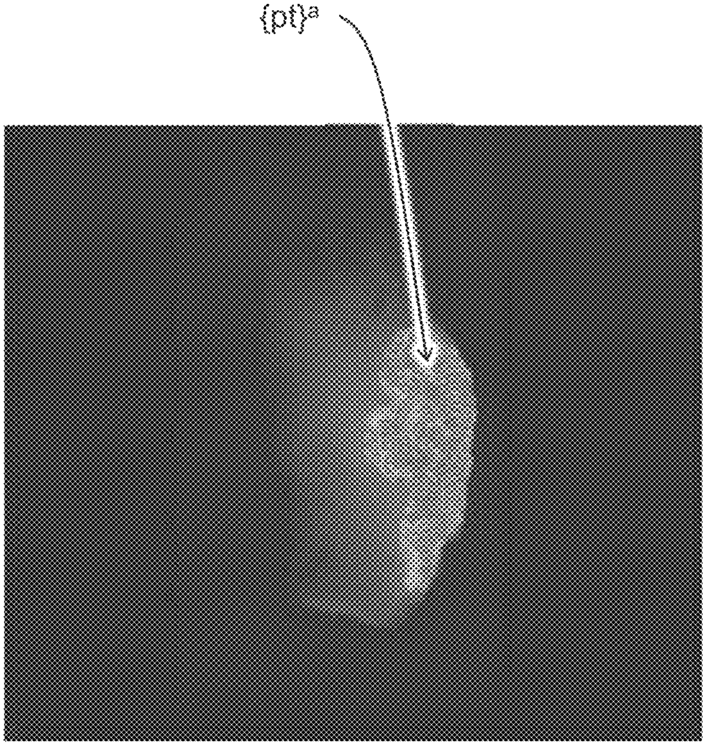
FIG. 23A-23F show sixth exemplary results derived with a fluorescence image obtained ex-vivo from a slice of the resected tissue.
Figure 23B:
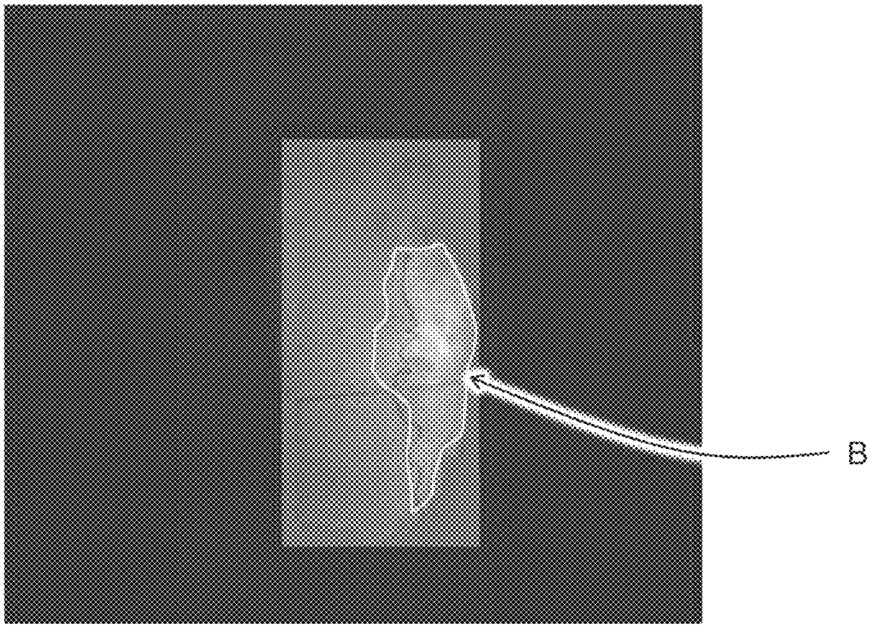
Figure 23C:
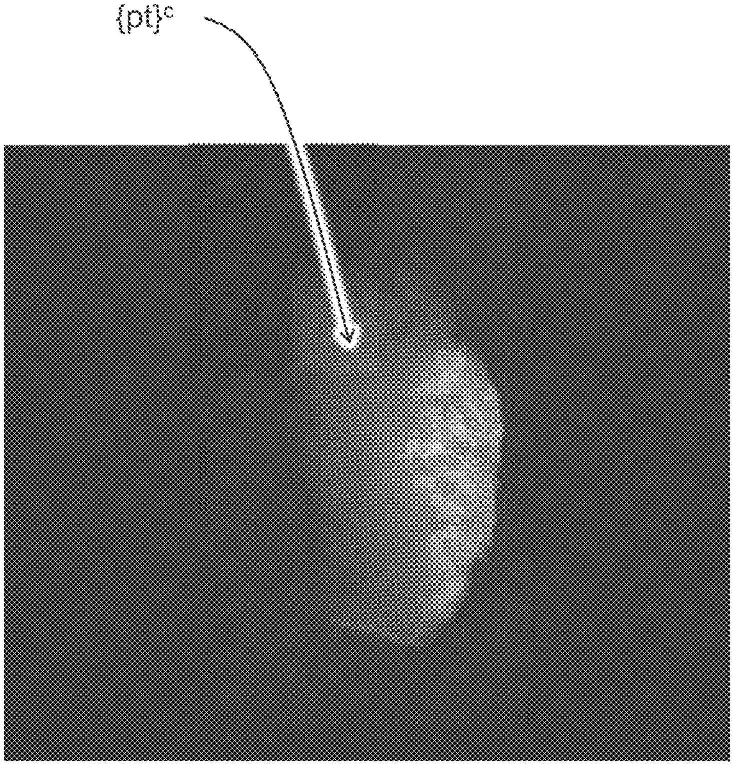
Figure 23D:
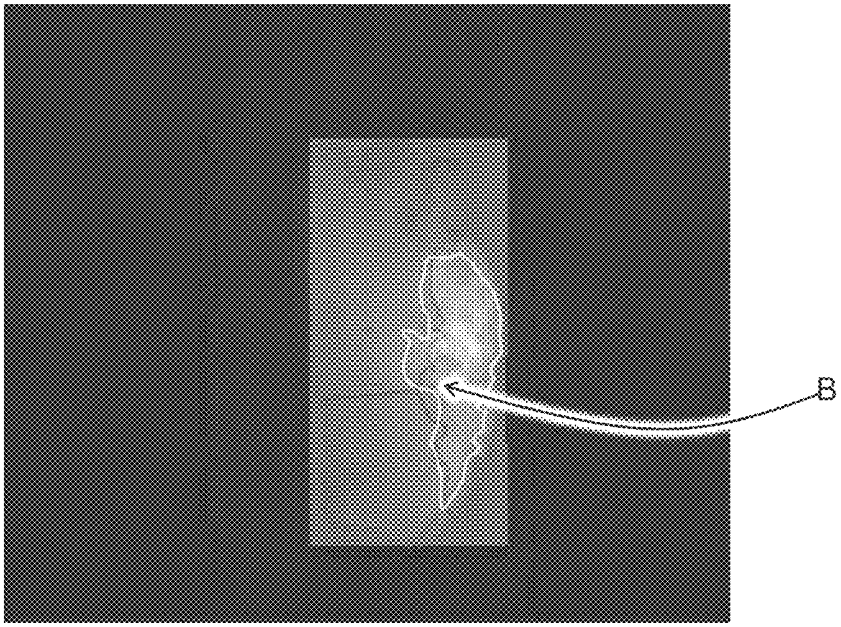
Figure 23E:
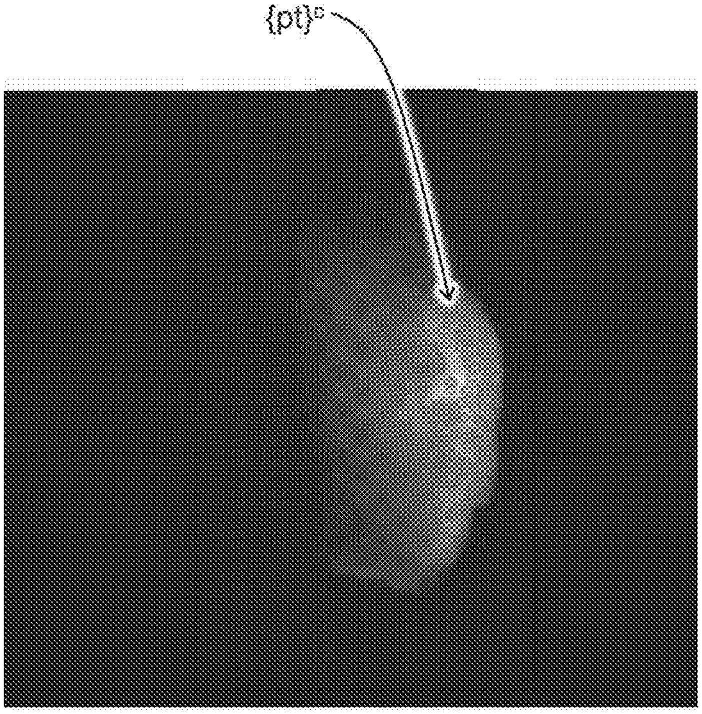
Figure 23F:
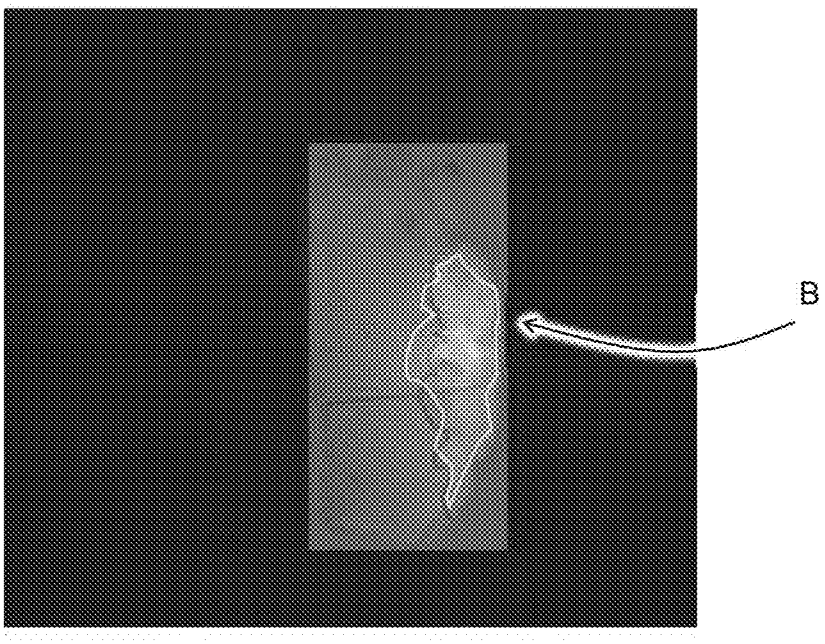

FIG. 23A, . . . , FIG. 23F show further exemplary results obtained for a fluorescence image obtained ex-vivo from a slice of the resected tissue.

FIG. 23A shows the filtered set $\{pt\}^n$ of candidate border positions as output by the candidate border position filter section 150 superposed on the original fluorescence image FI.

FIG. 23B shows superposed on the fluorescence image a border B directly constructed from the filtered set $\{pt\}^a$ of candidate border positions retrieved from candidate border position filter section 150.

FIG. 23C shows, superposed on the fluorescence image a set $\{pt\}^c$ of candidate border positions retrieved from further candidate border position matching section 152.

FIG. 23D shows superposed on the fluorescence image a border B constructed from set $\{pt\}^c$ of candidate border positions shown in FIG. 23C.

FIG. 23E shows, superposed on the fluorescence image a set $\{pt\}^n$ of candidate border positions retrieved from the candidate border position merging section 153.

FIG. 23F shows superposed on the fluorescence image a border B constructed from set $\{pt\}^n$ of candidate border positions shown in FIG. 23E.

From the exemplary results presented in example III, it was concluded that the border B constructed from the filtered set $\{pt\}^a$ of candidate border positions best matched the margin of the tumor indicated by a pathologist. For example for the fluorescence image obtained in-vivo the border constructed as shown in FIG. 21B provides the best correspondence with analysis of a pathologist.

Example IV

FIG. 24A to 24F show results for a fluorescence image obtained from a slice of tissue comprising a tongue carcinoma rendered fluorescent with the tracer ONM-100. ONM-100 consists of polymeric micelles labeled with IndoCyanine Green (ICG). Chemically, the ONM-100 drug substance comprises a diblock copolymer of polyethyleneglycol (PEG) (~113 repeating units) and a poly(methyl methacrylate) derivative covalently conjugated to functionalized ICG as the fluorophore. The ICG content was determined by a qualified method from its molecular weight of 37.5±12.5 kD.

Figure 24A:
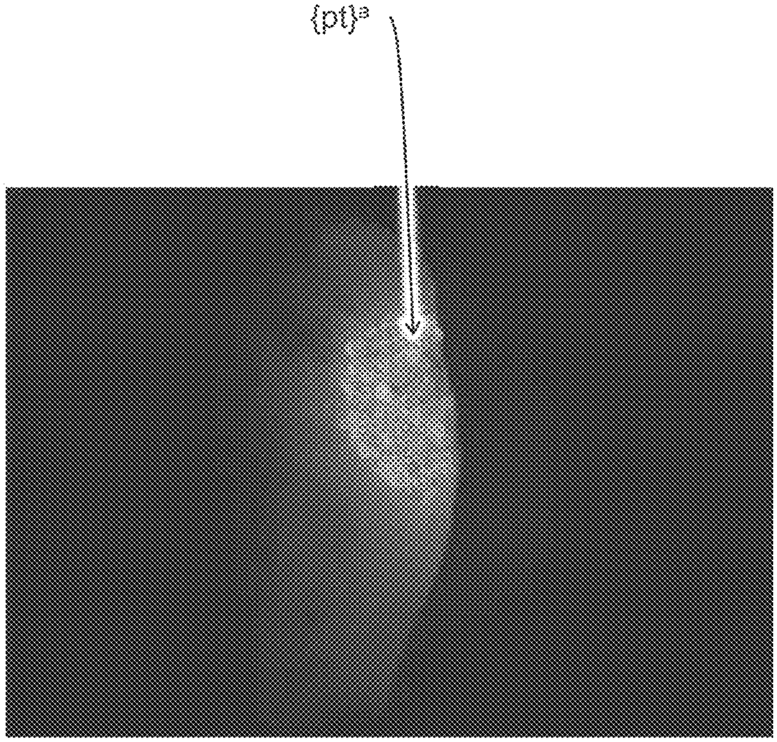
FIG. 24A-24F show seventh results derived with a fluorescence image obtained from a slice of tissue.

FIG. 24A shows the filtered set $\{pt\}^a$ of candidate border positions as output by the candidate border position filter section 150 superposed on the original fluorescence image FI.

Figure 24B:
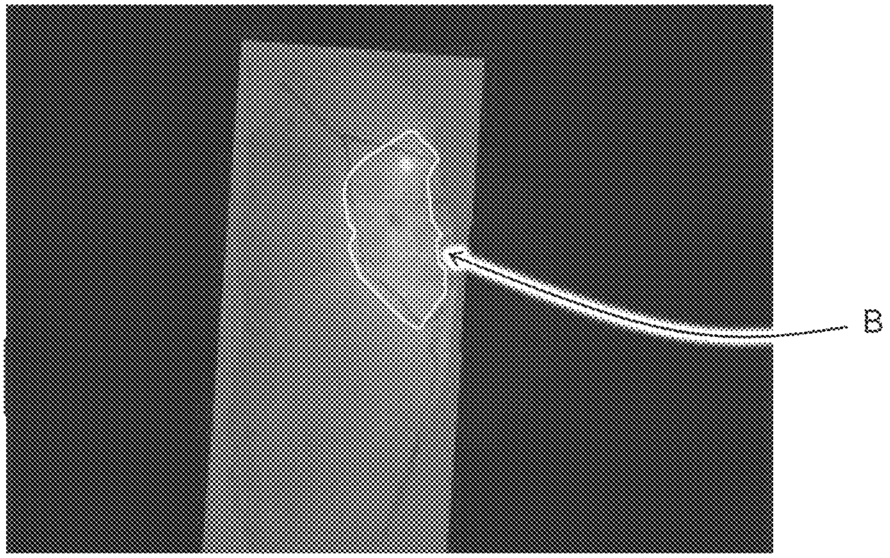

FIG. 24B shows superposed on the fluorescence image a border B directly constructed from the filtered set $\{pt\}^a$ of candidate border positions retrieved from candidate border position filter section 150.

Figure 24C:
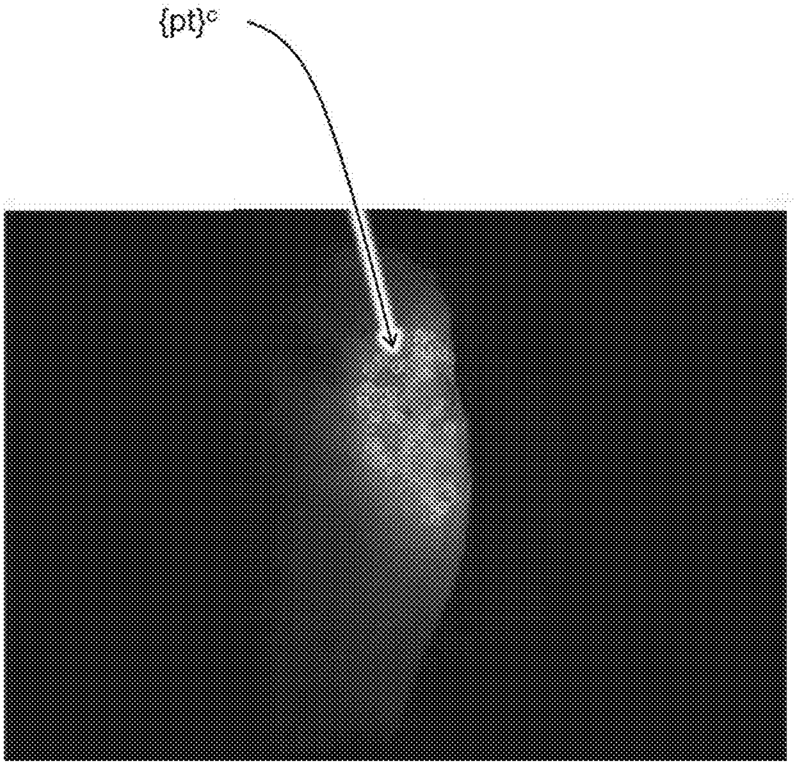

FIG. 24C shows, superposed on the fluorescence image a set $\{pt\}^c$ of candidate border positions retrieved from further candidate border position matching section 152.

Figure 24D:
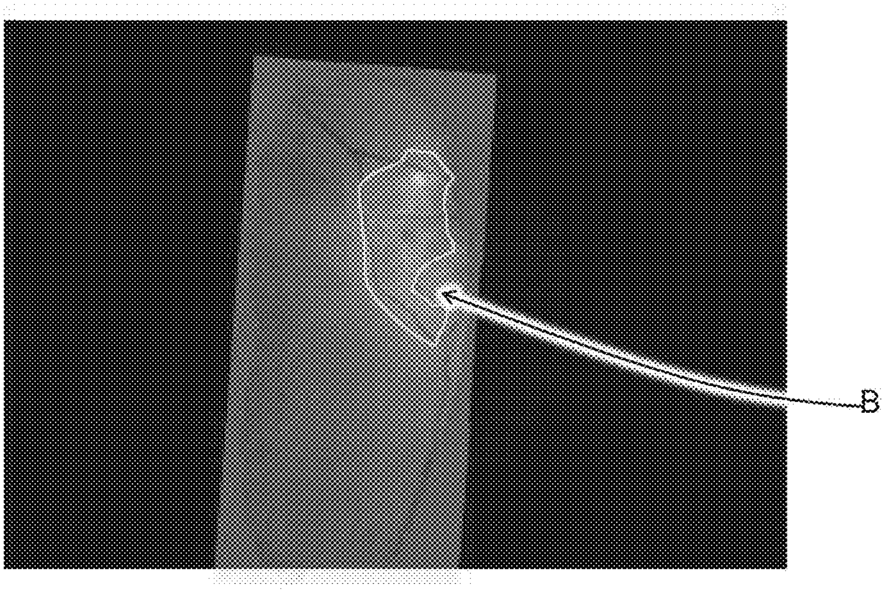

FIG. 24D shows superposed on the fluorescence image a border B constructed from set $\{pt\}^c$ of candidate border positions shown in FIG. 24C.

Figure 24E:
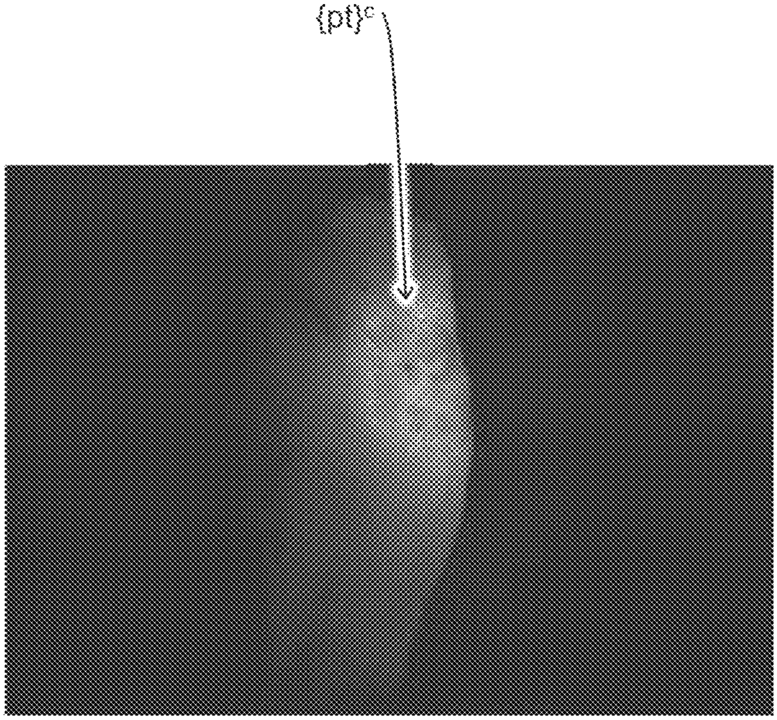

FIG. 24E shows, superposed on the fluorescence image a set $\{pt\}^n$ of candidate border positions retrieved from the candidate border position merging section 153.

Figure 24F:
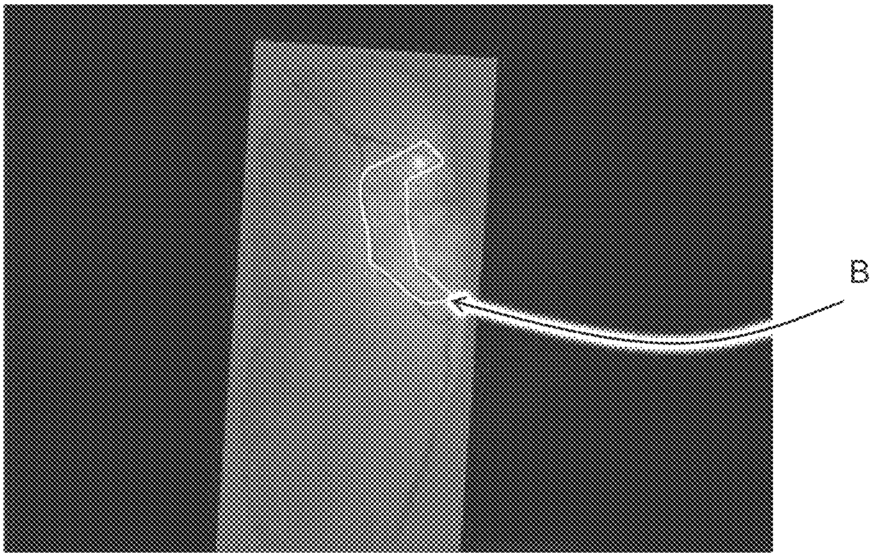

FIG. 24F shows superposed on the fluorescence image a border B constructed from set $\{pt\}^n$ of candidate border positions shown in FIG. 24E.

Figure 25:
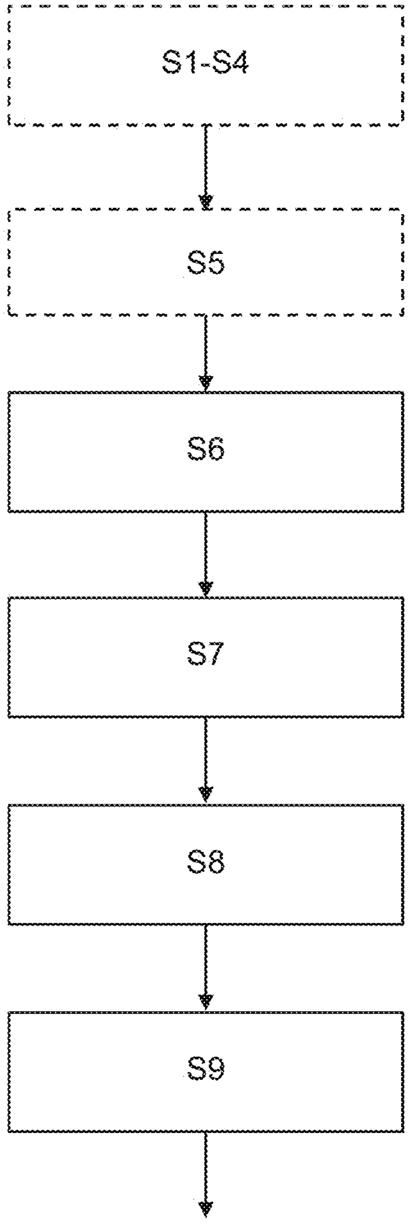
FIG. 25. schematically shows steps of an improved inspection method of inspecting a fluorescence image of a mammal tissue.

FIG. 25. schematically shows steps S5-S9 of an improved inspection method of inspecting a fluorescence image obtained from a mammal tissue. The fluorescence image is obtained with preparatory steps S1-S4 as follows.

In preparatory step S1 the mammal tissue is rendered photosensitive with a fluorescent agent. The fluorescent agent serves to visualize different types of tissue such as tumor tissue and tumor free tissue. In one example the fluorescent agent is a targeted fluorescent tracer such as Cetuximab-IRDye800CW or hexyl aminolevulinate, also briefly referred to as hexvix for imaging tumor tissue and/or infection and track medicinal therapy. In another example, the fluorescent agent is an untargeted fluorescent dye such as Indocyanine green (ICG) for imaging tissue perfusion. The excitation light with which the tissue is to be irradiated, in-vivo or ex-vivo is typically in the infra-red range. A fluorescent agent can be administered to the patient or may be used to impregnate the tissue.

In preparatory step S3 the mammal tissue being rendered photosensitive with the fluorescent agent is irradiated with excitation light and in preparatory step S4 a fluorescence image is captured of the mammal tissue. The fluorescence image comprises an array of pixels having respective fluorescence signal values. The fluorescence signal values comprise a first number of fluorescence signal values representing the mammal tissue in the fluorescence image. The first number is the number of pixels of the fluorescence image (FI) if only the mammal tissue is captured in the image, but can a smaller number if for example also a background is present in the image.

In step S6 of the improved inspection method a reference value is determined such that a second number of fluorescence signal values comprised in the first number of fluorescence signal values, is smaller than or equal to the reference value and the remainder of the first number of fluorescence signal values exceeds the reference value. The second number is a predetermined fraction of the first number.

In step S7 an average fluorescence signal value $\mu_R$ and a standard deviation $\sigma_R$ is determined is determined of the fluorescence signal values comprised in the second number of fluorescence signal values.

In step S8 an image segmentation is performed to distinguish in the fluorescence image FI a target region TR and a reference region RR to denote a remaining portion in the mammal tissue MT. This step is performed pixelwise. That is, it is determined per pixel (p) that it is part of the target region TR if an excess contrast-to-noise ratio mCNR (p) for the pixel exceeds a predetermined threshold value ($T_{CNR}$) and it is determined that the pixel is part of the reference region RR otherwise. Therein the excess contrast-to-noise ratio mCNR (p) of a pixel is defined as $$\tilde{m}CNR(p) = \frac{FI(p) - \mu_R}{c \cdot \sigma_R} \tag{1b}$$

Therein FI(p) is the fluorescence signal value of the pixel (p) and c is a regularization parameter. Optimal values are a threshold value of 1 and a value 2 for the regularization parameter c.

In step S9 at least one contour B of the target region TR is identified. In one example the at least one contour comprises a primary contour B that indicates a border of the target area with the reference area. In another example the at least one contour comprises a secondary contour that extends at a distance outside a border of the target area with the reference area to extend the target area with a safety area, to mitigate the risk that tissue near the target area that appears to be normal later develops into tumor tissue. In a specific implementation of the secondary contour B' extends at a distance outside the border in a manner that avoids an intersection of a specified anatomical structure. In an example both the primary contour and the secondary contour are identified.

An embodiment of the improved method is described with reference to FIG. 26. In this example the method is applied for ex-vivo inspection of a mammal tissue, wherein the mammal tissue is arranged on a background. In this example an average fluorescence signal value and the standard deviation of fluorescence signal values are determined from a portion BP of the fluorescence image FI that is designated as representing the background. With a user interface, a human operator can easily indicate a rectangular or square portion BP in the image wherein no mammal tissue is represented. Then statistical properties of the image data in this portion are determined and used to perform a preliminary segmentation indicated as step S5 in FIG. 25 wherein a preliminary segmentation is performed to segment the fluorescence image (FI) into a foreground region and a background region based on the statistical properties of the background region as estimated from the designated portion BP. Typically the estimated statistical properties comprise an average fluorescence signal value and a standard deviation of fluorescence signal values of the background. These statistical properties can be efficiently estimated from a minimum and a maximum fluorescence value identified in the designated portion BP as follows.

$$\mu_{est} = \frac{\min + \max}{2} \tag{3a}$$

$$\sigma_{est} = \frac{\max - \min}{2\sqrt{3}} \tag{3b}$$

Therein min, max respectively are the minimum fluorescence value and the maximum fluorescence value of all fluorescence values in the fluorescence image.

In the preliminary image segmentation S5 it is determined per pixel whether or not its fluorescence signal value (FSV) significantly exceeds an average background fluorescence signal value. If it is determined that a fluorescence signal value (FSV) of a pixel significantly exceeds the average background fluorescence signal value then that pixel is classified as part of the foreground region otherwise it is determined as part of the background region. As an example it is determined that a fluorescence signal value (FSV) of a pixel significantly exceeds the average background fluorescence signal value if a difference between its fluorescence signal value (FSV) and the background fluorescence signal value exceeds a regularization parameter times the standard deviation of the fluorescence signal values of the background. The regularization parameter is for example greater than 1, for example in a range of 1.05 to 5, for example about 2.

In one example the average fluorescence signal value and the standard deviation are estimated in a calibration step, wherein prior to capturing the fluorescence image a calibration fluorescence image is captured of the background only and the average fluorescence signal value and the standard deviation are determined are determined of the fluorescence signal values in the calibration fluorescence image.

A rough but useful estimation of the average fluorescence signal value can obtained as specified in equations (3a), (3b) above.

Figure 26:
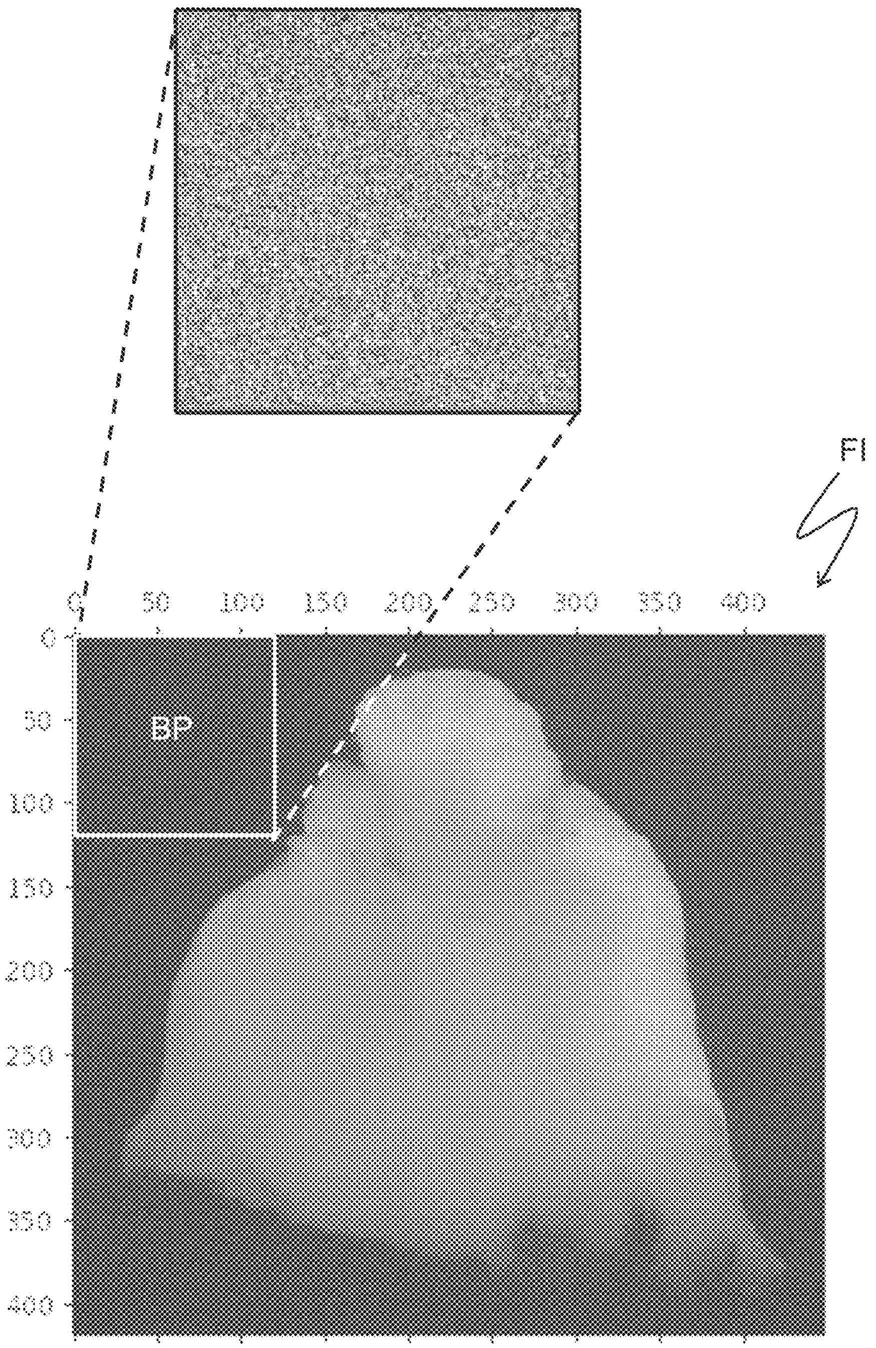
FIG. 26 shows an optional step of the improved inspection method.

In the example shown in FIG. 26 the following statistical properties of the background were estimated therewith:

$\mu_{est} \approx 5.18$; $\sigma_{est} \approx 1.59$

Based on this estimation pixels having a fluorescence value of at least 8.36 were identified as foreground FG, i.e. representing the mammal tissue and pixels having a lower fluorescence value as background BG.

FIG. 27A schematically shows how the fluorescence image (FI) is partitioned into a background area BG and a foreground area FG with a boundary B.

FIG. 27B shows a further correction of the boundary to a corrected boundary B'. The further correction is achieved by a dilation of the foreground FG by 1 pixel. The fluorescence signal values in the fluorescence image (FI) comprise a first number N1 of fluorescence signal values in the foreground. These represent the mammal tissue in the fluorescence image.

Figure 28A:
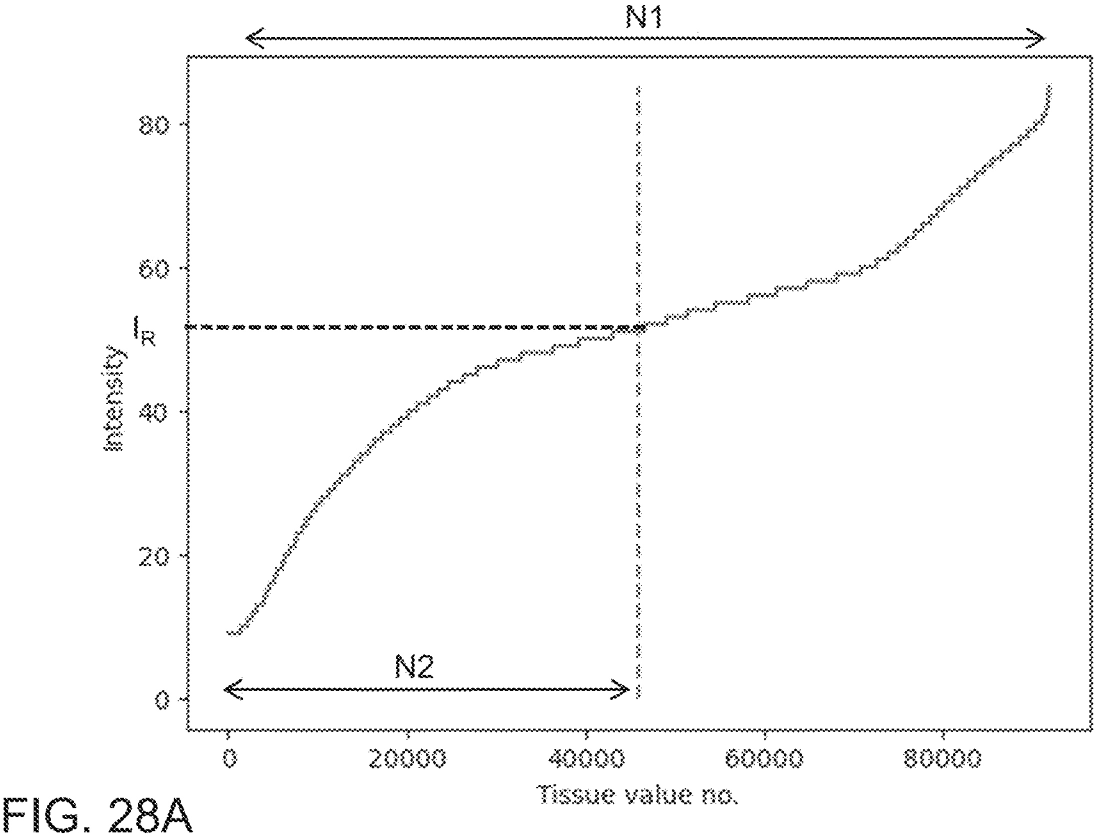
FIGS. 28A and 28B shows a segmentation step of the improved inspection method.

FIG. 28A shows that a reference value $I_R$ is determined such that a second number N2 of fluorescence signal values comprised in the first number N1 of fluorescence signal values is smaller than or equal to the reference value $I_R$ and the remainder of the first number of fluorescence signal values exceeds the reference value $I_R$. The second number N2 is a predetermined fraction of the first number N1. In this example the predetermined fraction is 0.5. This implies that the reference value IR is the median of the fluorescence signal values comprised in the first number N1 of fluorescence signal values. In a further analysis it is determined that the fluorescence signal values comprised in the second number N2 of fluorescence signal values have the following statistical properties. $\mu_R \approx 37.54$; $\mu_R \approx 12.91$. Therein $\mu_{RR}$ and $\sigma_{RR}$ respectively are is the estimated average value and the estimated standard deviation of the fluorescence signal values comprised in the second number N2 of fluorescence signal values.

Figure 28B:
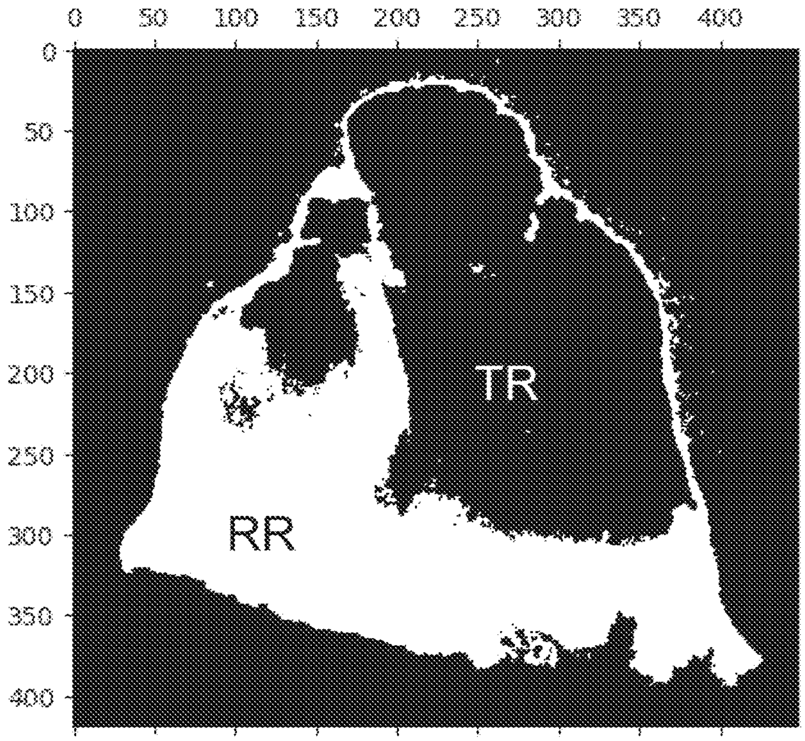

Based on these statistical properties an image segmentation is performed to distinguish in the fluorescence image a target region TR and a reference region RR, wherein the reference region denotes a remaining portion in the mammal tissue other than that denoted by the target region. In FIG. 28B pixels for which the excess contrast-to-noise ratio mCNR (p) for said pixel exceeds a predetermined threshold value ($T_{CNR}$) are identified as part of the target region TR indicated in black in FIG. 28B. The remaining pixels, indicated in white are identified as being part of the reference region RR. The excess contrast-to-noise ratio mCNR (p) of a pixel is defined as $$\tilde{m}CNR(p) = \frac{FI(p) - \mu_R}{c \cdot \sigma_R} \quad (1b)$$

Therein FI(p) is the fluorescence signal value of the pixel (p) and c is a regularization parameter. In the present example c has the value 2 and the predetermined threshold value ($T_{CNR}$) has the value 1.

Figure 29A:
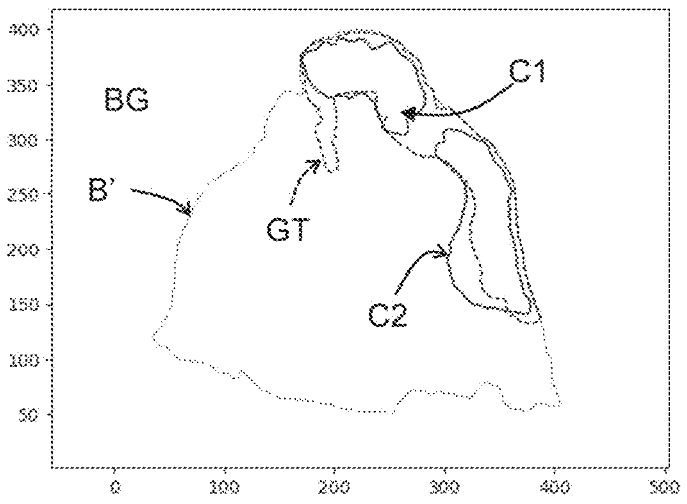
FIGS. 29A, 29B and 29C show application of the method to fluorescence images obtained from sample tissues.
Figure 29B:
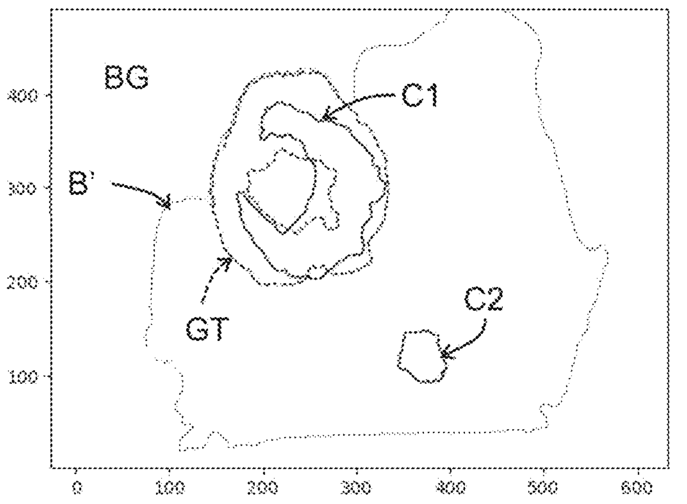
Figure 29C:
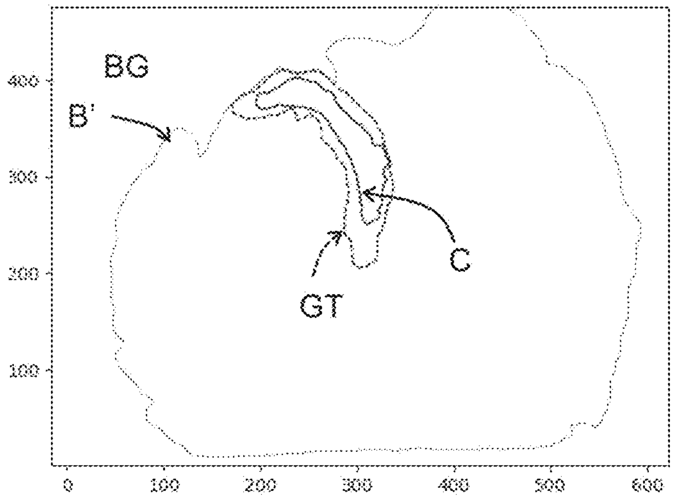
Figure 30A:
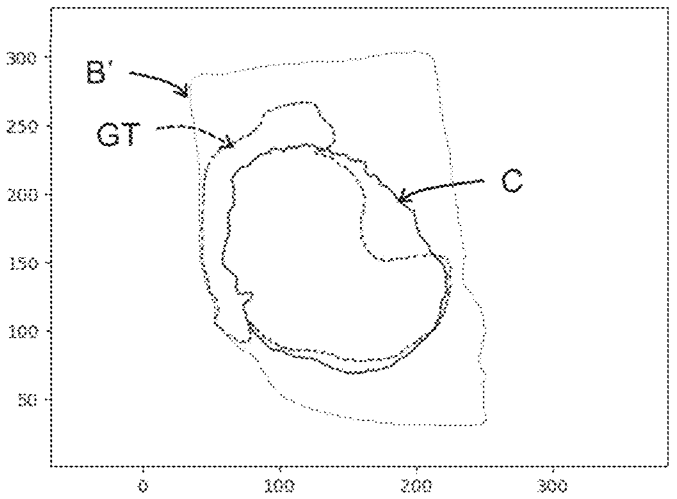
FIGS. 30A, 30B and 30C show application of the method to fluorescence images obtained from further sample tissues.
Figure 30B:
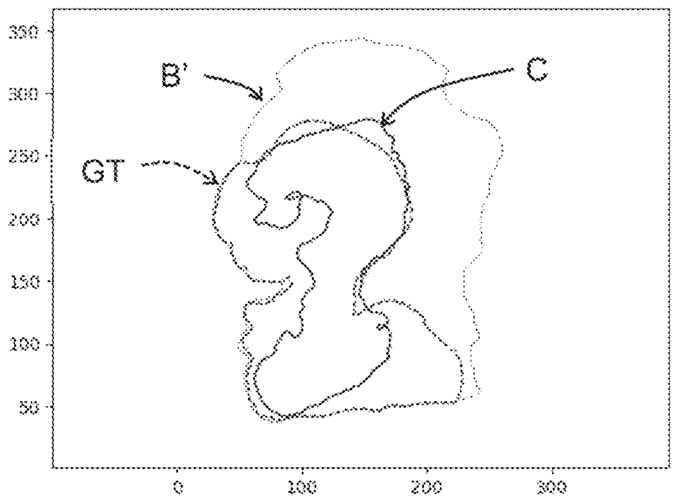
Figure 30C:
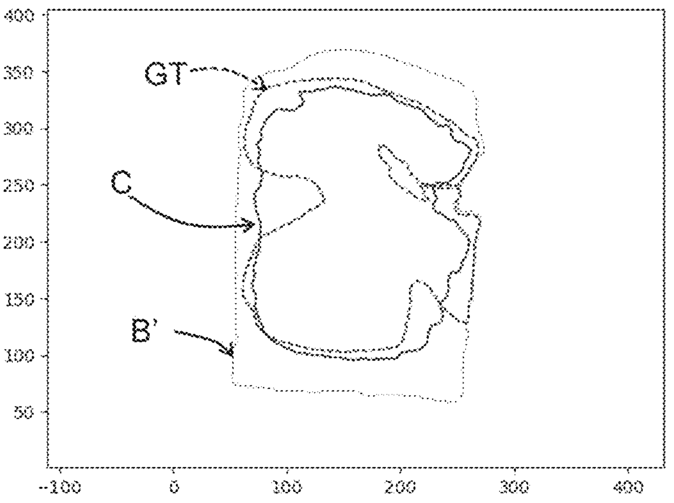

FIG. 29A, 29B, 29C and FIGS. 30A, 30B and 30C show various examples wherein the method as described above is applied. The examples shown in FIGS. 29A, 29B and 29C are penile squamous carcinoma tissue slices from tissue resected from a first patient. The examples shown in FIGS. 30A, 30B and 30C are penile squamous carcinoma tissue slices from tissue resected from a second patient. The fluorescence images were obtained with a PEARL imaging device after the tissue was rendered fluorescent with cetuximab-IRDye800CW, i.e. the wavelength range captured is in the range of 800 nm. Therein the reference B' indicates the corrected boundary of the mammal tissue with respect to the background. References C, C1 and C2 indicate contours of a target region in the tissue estimated by the method. The ground truth, i.e. the contour of tumor tissue as determined by a pathologist is indicated by the reference GT.

Figure 31:
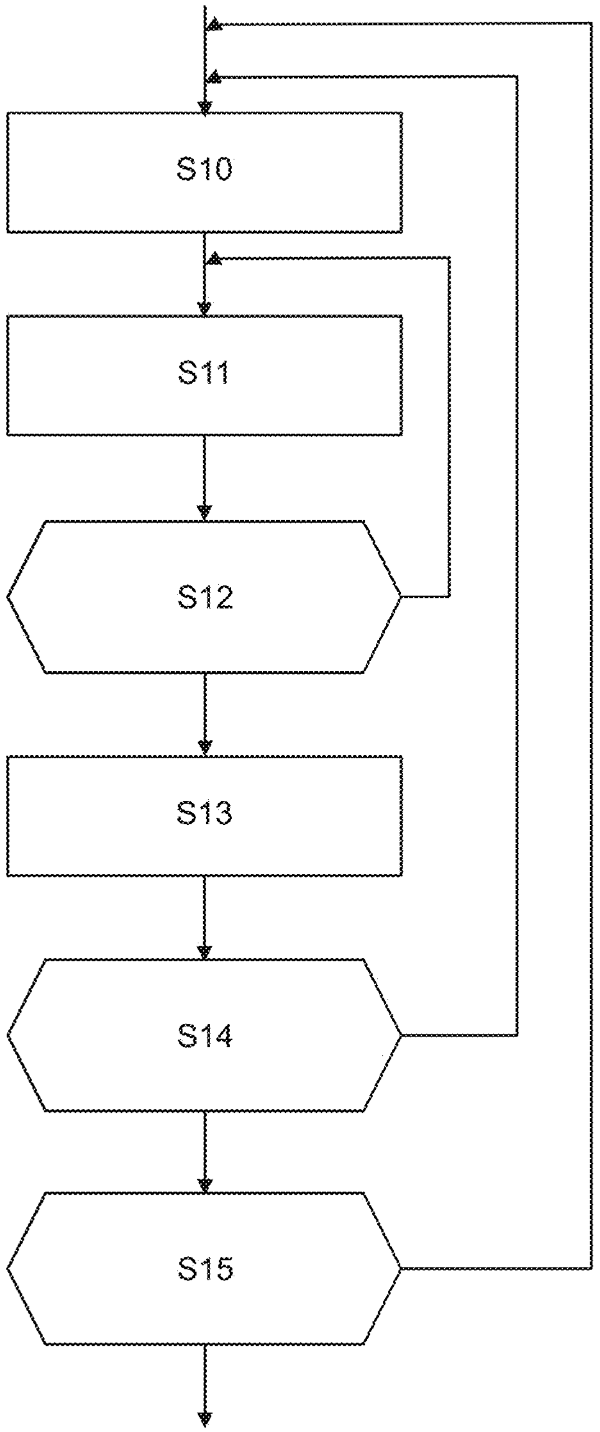
FIG. 31 schematically shows steps of another improved inspection method of inspecting a fluorescence image of a mammal tissue.

The method as described above can be used in combination with a scanline based method. An example of a scan trajectory based method is schematically illustrated in FIG. 31.

The inspection method illustrated therein comprises a step S10 wherein at least one fluorescence signal value vector of fluorescence signal values in the fluorescence image along a scan trajectory is obtained. For practical purposes the scan trajectory is typically a line aligned with a principle axis of the fluorescence image.

In step S11 for a threshold value ts one or more candidate scan trajectory sections (typically scanline sections) are determined in which the fluorescence signal value exceeds the threshold value ts. This is repeated for a plurality of threshold values. In step S12 it is verified whether or not the procedure has been performed for all threshold values of the plurality.

The remaining sections of the scan trajectory are considered as reference sections, and statistical properties are derived of the fluorescence signal values of the pixels forming part thereof. Typically the average value $\mu_{rs}$ and the standard deviation $\sigma_{rs}$ of these fluorescence signal values are determined. As the value found for these statistical properties depends on the selection of the threshold value ts, they can be written as $\mu_{rs}$ (ts) and $\sigma_{rs}$ (ts) respectively.

Having determined these statistical properties it is determined which of the pixels (p) on the scan trajectory comply with the requirement mCNR(p)≥tr, wherein:

$$\tilde{m}CNR(p) = \frac{FI(p) - \mu_{rs}(ts)}{c \cdot \sigma_{rs}(ts)} \quad (1b')$$

Therein c is a regularization parameter that is selected from a range of 1.5 to 3, for example about 2 and tr is a threshold, for example of a value 1. In step S13 it is determined for which threshold value ts of the plurality of threshold values the respective set of candidate scan trajectory sections best matches the set of one or more scan trajectory sections that are obtained using the mCNR requirement referred to above. In an example the extent to which the identified scan trajectory sections match is determined by the F-measure as specified above.

Alternatively, an optimal value $t_{opt}$ is determined as $$t_{opt} = \underset{ts}{\operatorname{argmin}} |ts - (\mu_{rs}(ts) + 2 * \sigma_{rs}(ts))| \quad (9)$$

In the embodiment of FIG. 31, the procedure in steps S10-S13 is repeated for a plurality of mutually different scan trajectories of a set of scan trajectories. To that end it is verified in step S14 whether the steps S10-S13 have been performed for all scan trajectories of a set of scan trajectories. Hence for each scan trajectory in the set of scan trajectories the value $t_{opt}$ is determined as well as the partitioning of the scan trajectory into scan trajectory sections on the basis of the value $t_{opt}$. As noted the scan trajectories are preferably lines aligned with a primary axis of the fluorescence image. For example the set of all horizontal lines, or a subset of horizontal lines.

In the embodiment shown the procedure in steps S10-S14 is also repeated for a plurality of sets of scan trajectories. To that end it is verified in step S15 whether the steps S10-S14 have been performed for sets of scan trajectories, for example for the set of horizontal scanlines and vertical scanlines.

The method of FIG. 31 can be used in combination with the method of FIG. 25 in various ways. In one example the method of FIG. 25 provides an indication of a range where the optimal threshold value $t_{opt}$ is expected to be. For example the range is selected as $$\mu_r \le t_{opt} \le \mu_r + 4 * \sigma_r \quad (10a)$$

or $$\mu_r + \sigma_r \le t_{opt} \le \mu_r + 3 * \sigma_r \quad (10b)$$

In another example the method of FIG. 25 provides an extension range to limit a range of extension of the scan trajectory. The extension range may for example indicate a line segment that crosses a contour as indicated by the method of FIG. 25 and that extends a predetermined distance at both sides of the crossing position. Alternatively the method of FIG. 25 may indicate an extension range for a scan trajectory through the target region and extending a predetermined distance at both sides of the target region.

In a still further example, the method of FIG. 25 provides an indication of an orientation of a contour of a target region to be identified. The indication is for example a main axis of a contour identified in the method of FIG. 25. Using this information the method of FIG. 25 can be optimally performed by performing the scan trajectory based analysis with scanlines transverse to the main direction.

A suitable definition of the main axis is a line segment that minimizes an average distance measure between that line segment and the points of the contour. As an example the distance measure is the Euclidian distance measure but other options are available too. A main axis can be found with the OpenCV tool "fitLine".

For practical purposes, the fluorescence image (FI) is rotated prior to performing the method of FIG. 31. In that case the rotation aligns the main axis of the contour with a coordinate axis of the fluorescence image and the scan lines are directed along another coordinate axis of the fluorescence image (FI).

In the method of FIG. 31 described above, the threshold value ts is varied to determine for the threshold value $t_{opt}$ for which it is achieved that the respective set of candidate scan trajectory sections of a scan trajectory best matches the set of one or more scan trajectory sections that are obtained using the mCNR requirement referred to above. Therein the statistical properties $\mu_{rs}$ and $\sigma_{rs}$ are estimated from the sections of the scan trajectory that are not identified as candidate scan trajectory sections. In an alternative approach it is presumed that the scan trajectory has a crossing at a presumed position and that the statistical properties $\mu_{rs}$ and $\sigma_{rs}$ are estimated from the scan trajectory section at the side of the presumed crossing having the lowest average fluorescence value. Based on the mCNR measure with these estimated statistical properties the scan trajectory is partitioned into reference scan trajectory sections and target scan trajectory sections and it is determined if the presumed crossing coincides with a transition from a reference scan trajectory section to a target scan trajectory section or reversely. If this is the case, the presumed crossing is a candidate contour point. This approach is described in more detail in European patent application 23154545.0 filed by the same Applicant on 1 Feb. 2023. The method of FIG. 1 can provide the locations of the contour therein as heuristic information to restrict the search range of the optimal crossing positions in the alternative approach of the method of FIG. 31.

Figure 32:
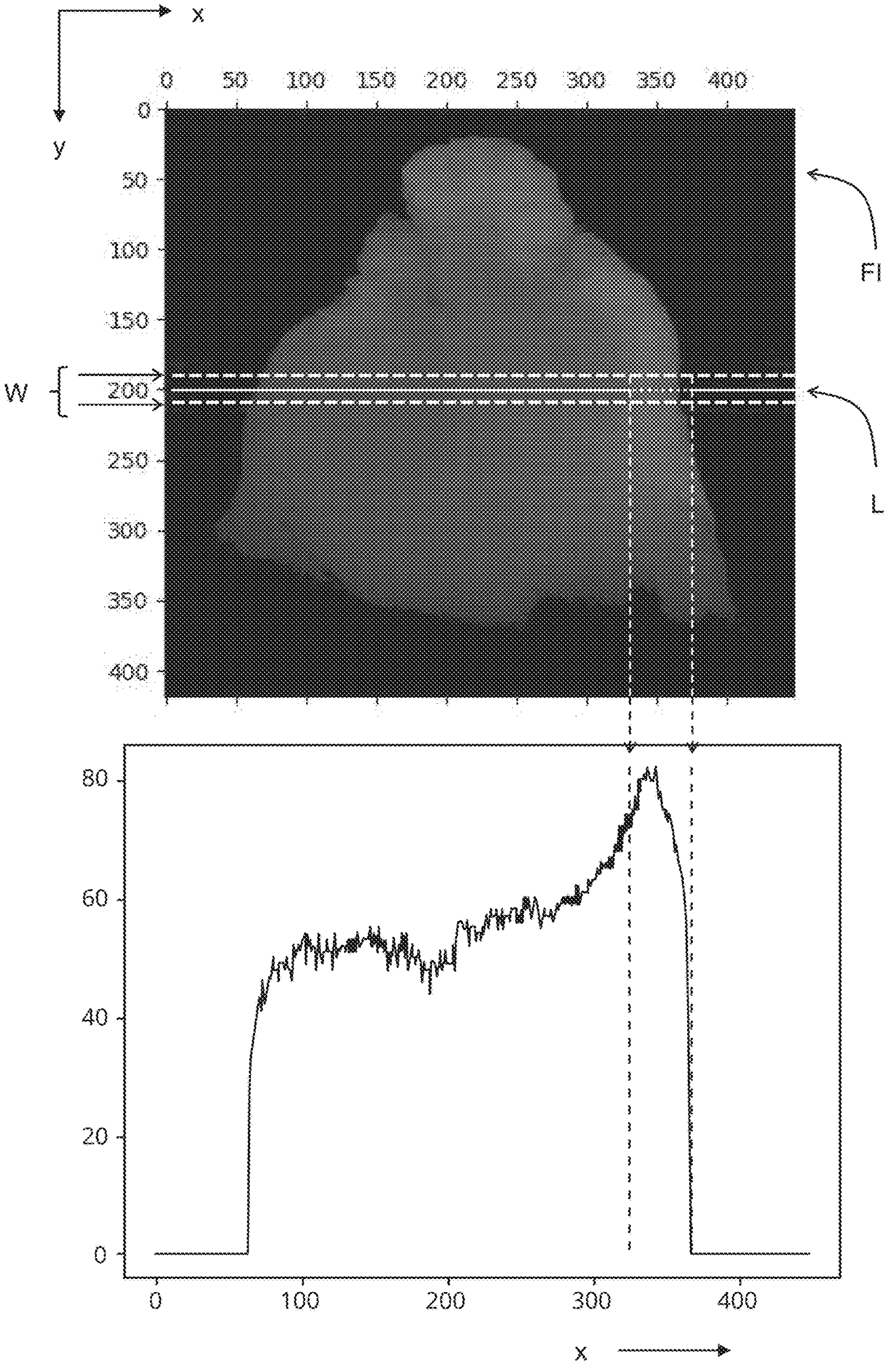
FIGS. 32-34 show application of the embodiment of FIG. 31 to a fluorescence image of sample tissue.

The method of FIG. 31 is illustrated with reference to FIG. 32. On top, FIG. 32 shows a fluorescence image (FI) obtained from a sample of a mammal tissue. The bottom shows intensity values along a scan trajectory L in the fluorescence image (FI). In the example shown, each intensity value on the scan line is obtained as the Gaussian weighted average of the pixels in the strip W having the same x-coordinate.

Figure 33:
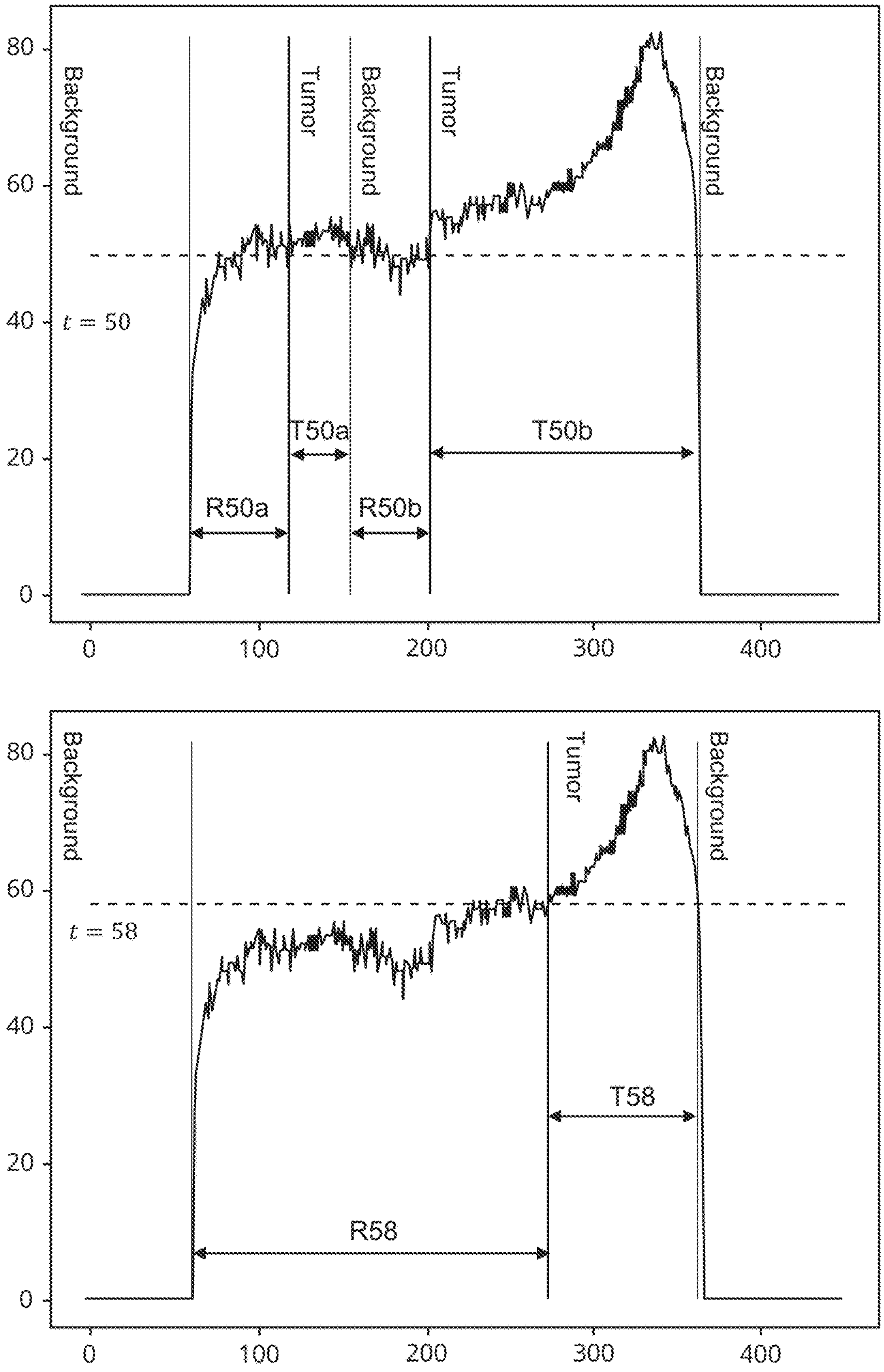

FIG. 33 shows how in step S11 for each threshold value of a plurality of threshold values a respective set of candidate scan trajectory sections is determined in which the fluorescence signal value exceeds the threshold value. The upper part of FIG. 33 shows a first example, wherein the threshold value 50 causes a partitioning with two candidate target sections T50*a* and T50*b* and two reference sections R50*a* and R50*b*. The lower part of FIG. 33 shows a partitioning with one candidate target section T58 and one reference section R58 for the threshold value 58.

For each threshold value, the statistical properties the statistical properties $\mu_{rs}$ and $\sigma_{rs}$ are estimated from the fluorescence signal values in the one or more reference sections of the scan trajectory, and based on these statistical properties an alternative partitioning of the scan trajectory is determined according to the mCNR criterion. The threshold $t_{opt}$ is identified for which the threshold based partitioning best matches the mCNR-based partitioning using the statistical properties of the one or more reference sections.

Figure 34:
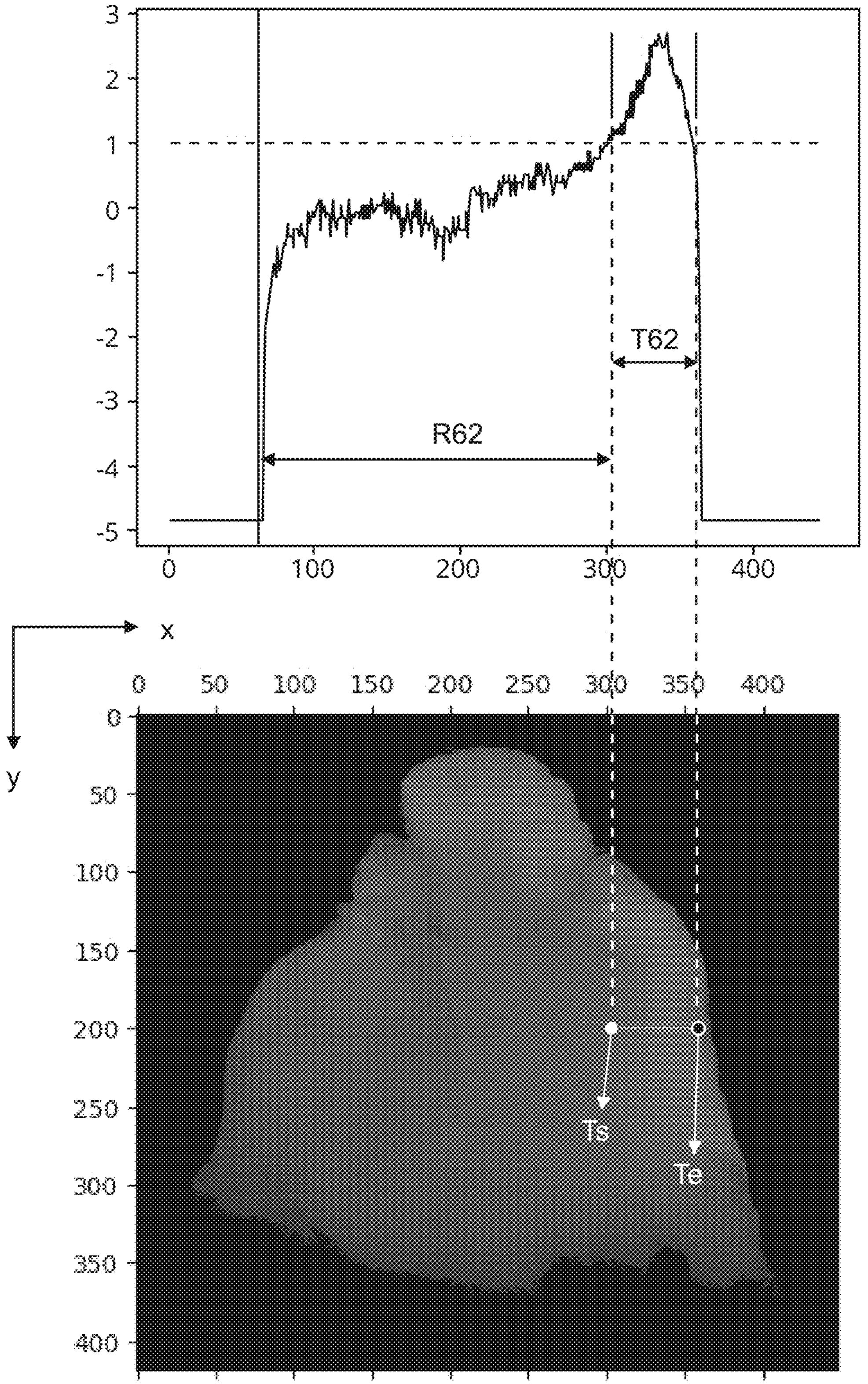

As shown in FIG. 34, in step S13 of the method of FIG. 31 it is found for this scanline that the optimal threshold is 62. Therewith the scanline is partitioned into reference section R62 and target section T62, as shown in the upper part of FIG. 34. As shown in the lower part of FIG. 34 therewith contour points Ts and Te are identified that respectively indicate the start of the target region T62 and the end of the target region when traversing the scanline in the positive x-direction.

Figure 35:
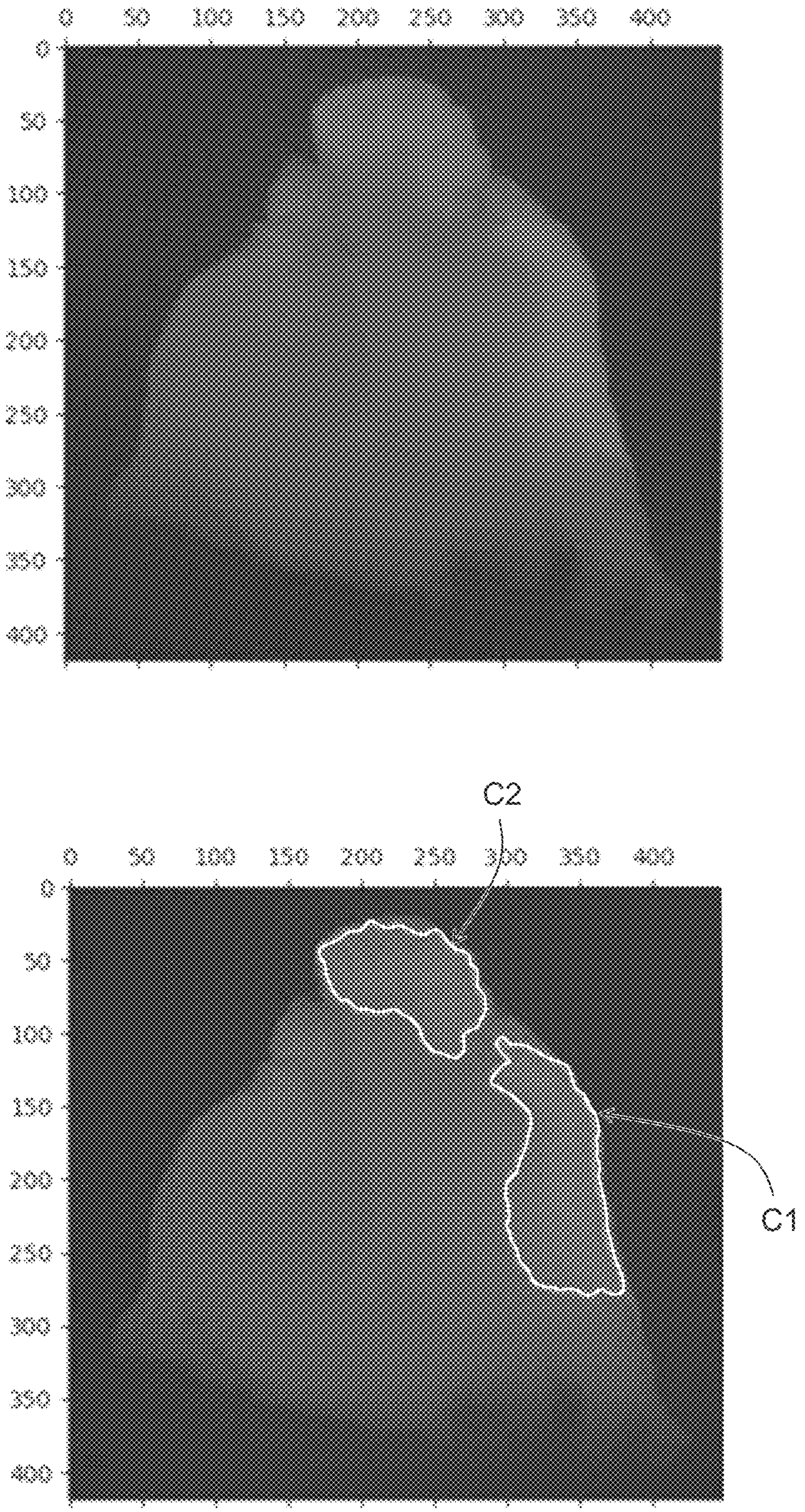
FIGS. 35-38 show application of the embodiment of FIG. 31 using heuristic information from the method of claim 1.

As another example, FIG. 35 shows how the method of FIG. 25 is applied to identify a first contour C1 and a second contour C2 see the lower part of FIG. 35 to the fluorescence image shown in the upper part of FIG. 35.

Figure 36:
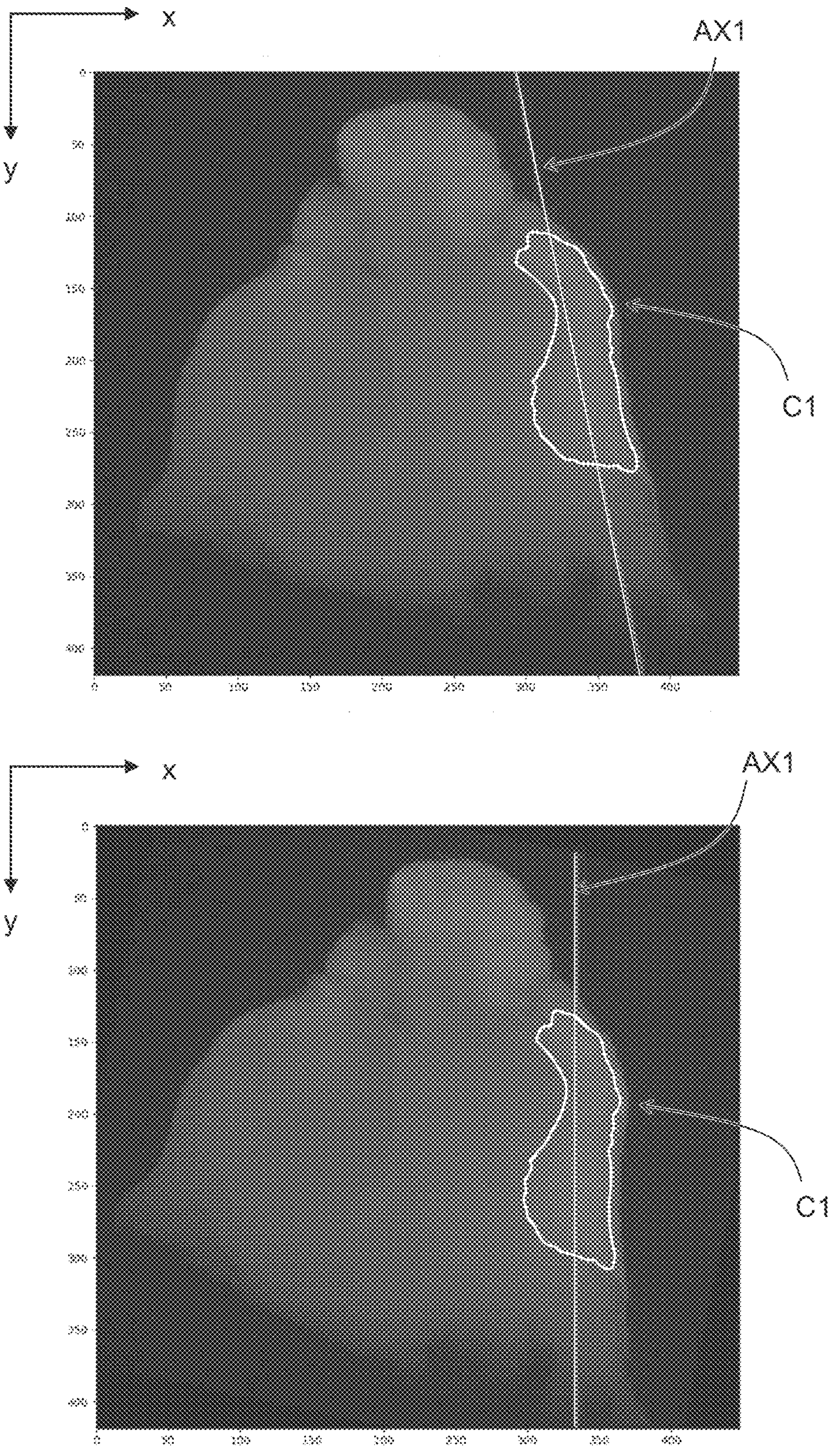

The upper part of FIG. 36 shows how a main axis AX1 of the target region with contour C1 is determined. The lower part of FIG. 36 shows how the fluorescence image (FI) is rotated such that the main axis AX1 is aligned with one of the principle axes (here the y-axis) of the fluorescence image (FI). It is noted that for contours with more complex shapes, multiple lines could be used to fit.

The fluorescence image (FI) rotated in this manner can be optimally scanned with scanlines directed according to the x-axis. Furthermore the location of the contour C1 can provide heuristic information that reduces the scanline based approach in FIG. 31. For example the heuristic information indicates a spatial search range or indicates an intensity search range.

Figure 37:
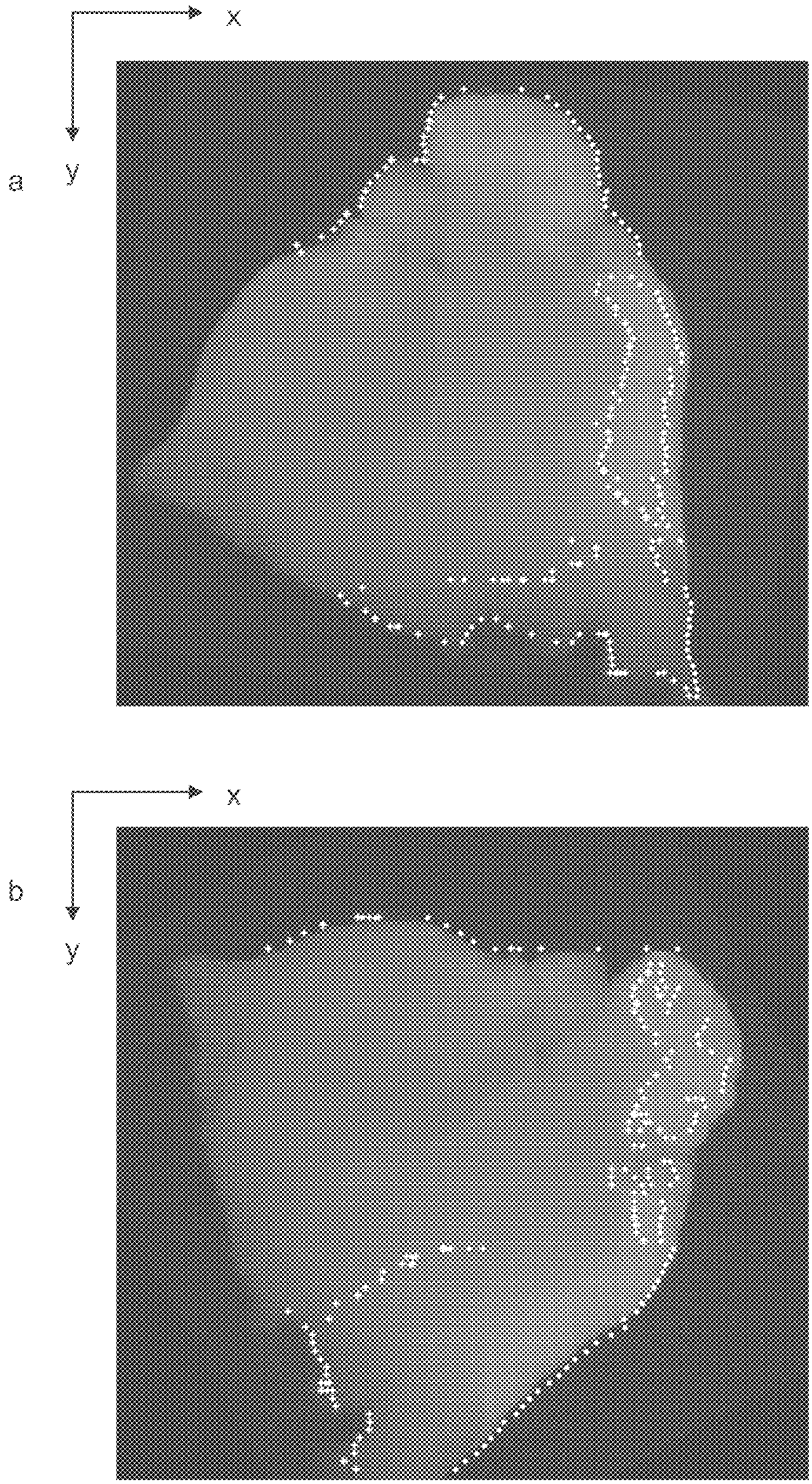

In the example shown in the upper part of FIG. 37 indicates the start points (+) and end points (·) of target sections identified with the threshold based version of the method of FIG. 31 using the heuristic information of the method of FIG. 1 and having the image aligned with the first contour C1 indicated in FIG. 35. The lower part of FIG. 37 indicates the start points (+) and end points (·) of target sections identified with the threshold based version of the method of FIG. 31 using the heuristic information of the method of FIG. 1 and having the image aligned with the second contour C2 indicated in FIG. 35.

Figure 38:
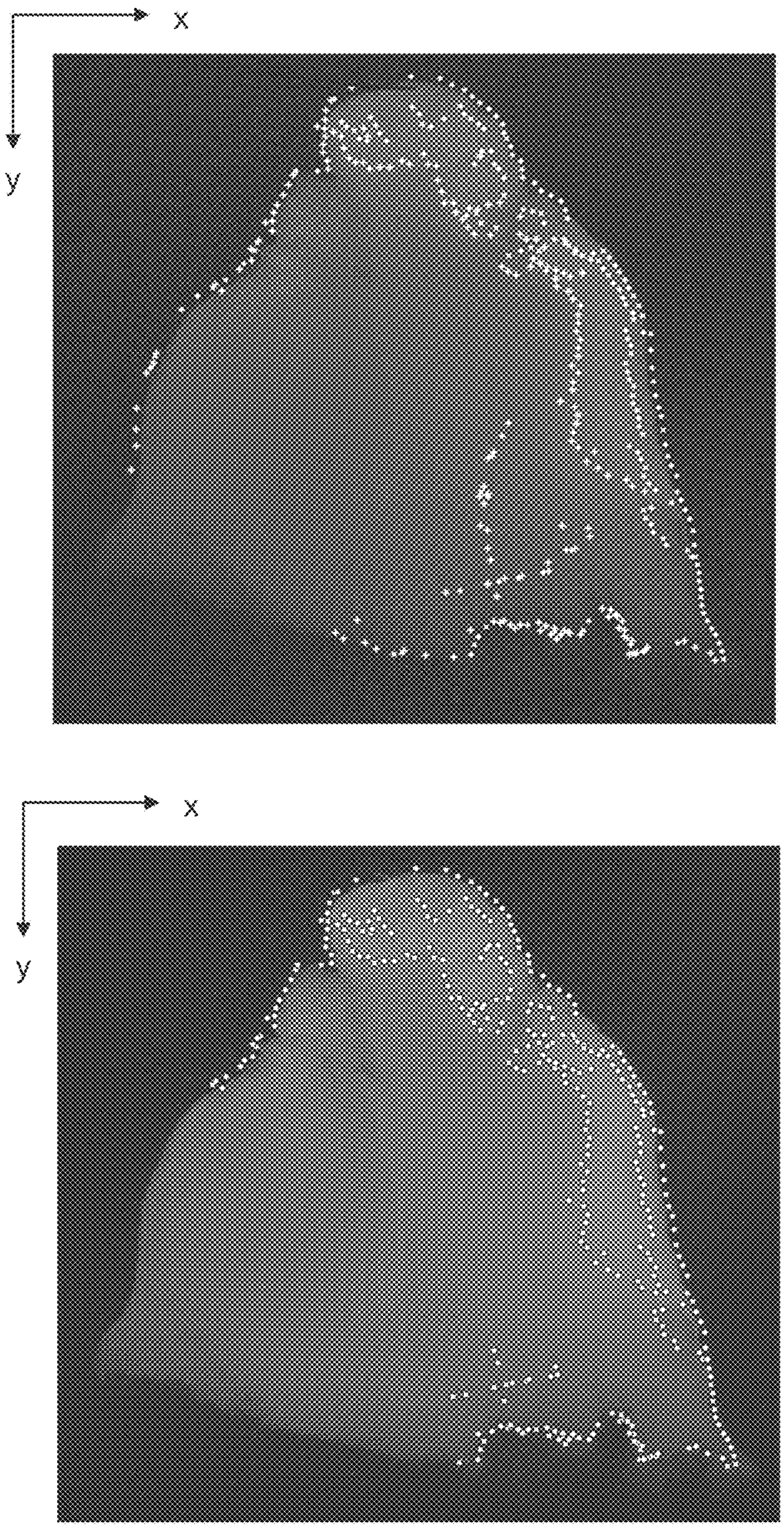

The upper part of FIG. 38 shows the points identified for each of the contours mapped into the original image.

The lower part of FIG. 38 shows how in a subsequent step isolated points are removed. A point is considered isolated if a local point density is lower than a threshold value, that is if it is the case that in a region of predetermined size centered around the point the ratio of the number of points and the size of the region is less than a predetermined value. Typically the size of the region is in a range selected from 100 to 1000 pixels, and the minimum number of points required to be present in the region is selected in a range from 5 to 50. Best results are obtained if the number of points is in a range of 1/30 to 1/20 the size of the range. In this example region has a radius of 40 pixels, i.e. the area of the region comprises about 500 pixels and the minimum number of points is 20.

In an additional or alternative processing step, clusters of points having a maximum pixel intensity less than a reference value are rejected. The reference value is for example the global intensity mean plus a factor of the standard deviation, as a modifiable parameter. In a further additional or alternative processing step a cluster of points is rejected if its area (to be computed) is lower than a certain fraction of the total image area.

Figure 39:
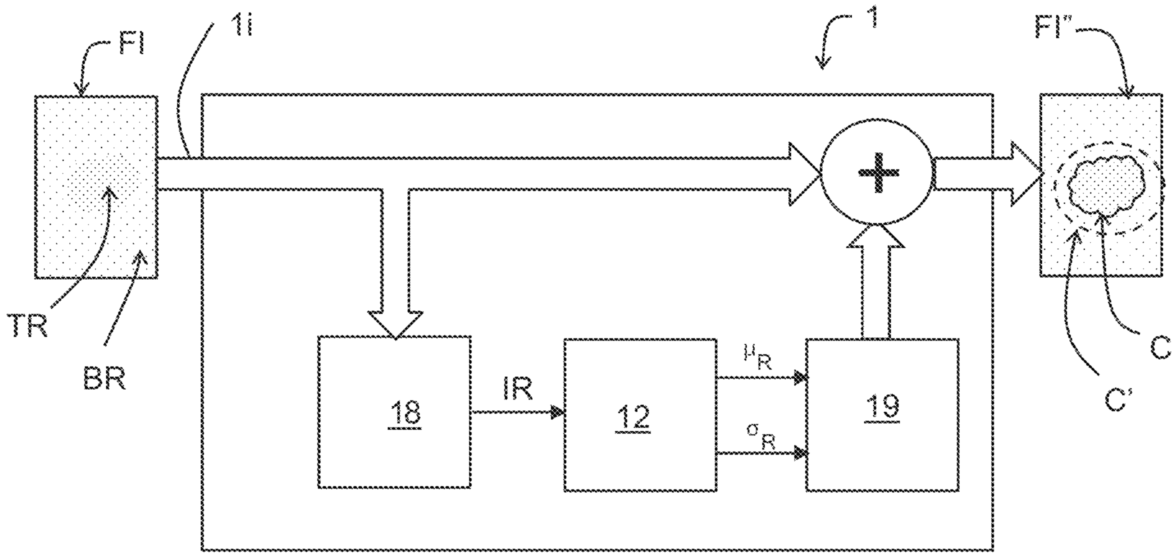
FIG. 39 schematically shows an inspection device according to an embodiment of the invention.

FIG. 39 schematically shows an inspection device 1 for inspection of a mammal tissue that is configured to obtain a fluorescence image FI of the mammal tissue MT being rendered photosensitive with a fluorescent agent and being irradiated with excitation light. The fluorescence image FI comprises an array of pixels having respective fluorescence signal values. The fluorescence signal values comprise a first number N1 of fluorescence signal values that representing the mammal tissue in the fluorescence image. In case a background is present in the image the first number is less than the total number of pixels in the fluorescence image (FI). Otherwise the first number N1 may be equal to the total number of pixels. In the example shown the an inspection device 1 obtains the fluorescence image (FI) from an external input 1*i*. Alternatively the inspection device may include a camera for capturing the image. Also the inspection device may include a proper excitation light source.

The inspection device 1 comprises a reference value determination module 18 that is configured to determine a reference value IR such that a second number N2 of fluorescence signal values comprised in the first number of fluorescence signal values is smaller than or equal to the reference value IR and the remainder of the first number of fluorescence signal values exceeds the reference value. In one example the second number is a predetermined fraction of the first number for example the N2/N1=0.5, in which case the reference value is the median. A statistical property evaluation module 12 determines an average fluorescence signal value ($\mu_R$) and a standard deviation ($\sigma_R$) of the fluorescence signal values comprised in the second number N2 of fluorescence pixel values.

A segmentation module 19 performs an image segmentation to distinguish in the fluorescence image (FI) a target region (TR) to denote a portion in the mammal tissue (MT) that is identified as tumorous tissue and a reference region (RR) to denote a remaining portion in the mammal tissue (MT). The segmentation module operates in a pixelwise manner in that it determines per pixel (p) that it is part of the target region (TR) if an excess contrast-to-noise ratio mCNR (p) for said pixel exceeds a predetermined threshold value ($T_{CNR}$) and to determine that the pixel is part of the reference region (RR) otherwise, wherein the excess contrast-to-noise ratio mCNR (p) of a pixel is defined as $$\tilde{m}CNR(p) = \frac{FI(p) - \mu_R}{c \cdot \sigma_R} \tag{1b}$$

wherein FI(p) is the fluorescence signal value of the pixel (p) and c is a regularization parameter. Optimal values are $T_{CNR}$=1 and c=2.

The segmentation module 19 further is configured to identify a contour C of the target region. The contour C is a primary contour that indicates a border of the target area with the reference area. The segmentation module 19 further is configured to identify a secondary contour C' that extends at a distance outside a border of the target area with the reference area. In the example shown the segmentation module 19 is configured to generate the secondary contour C' such that it extends at a distance outside the border in a manner that avoids an intersection of a specified anatomical structure.

Figure 40:
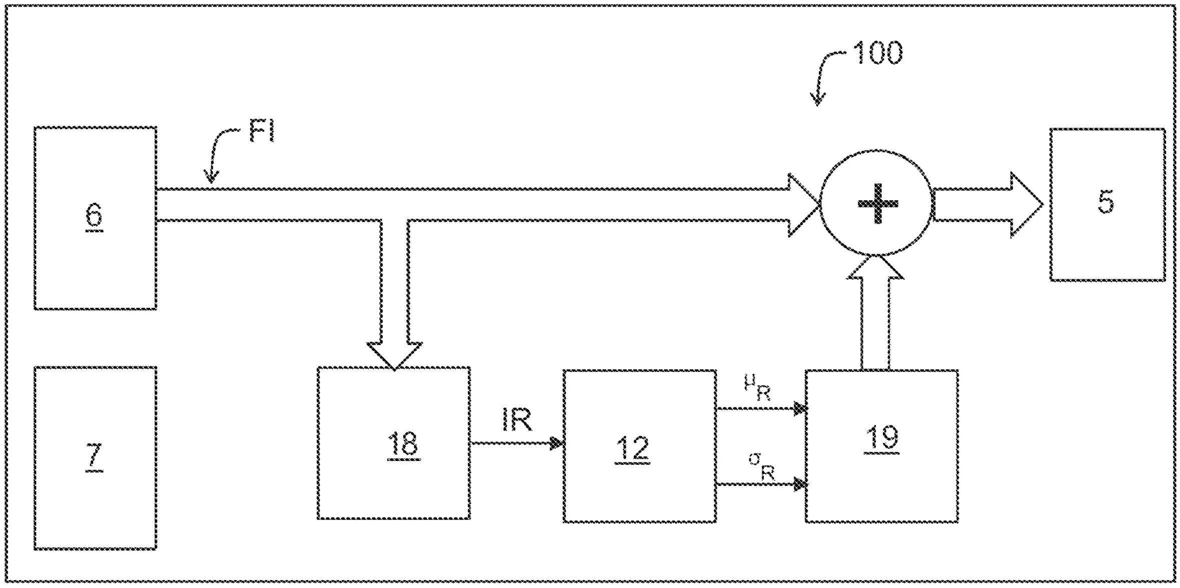
FIG. 40 schematically shows a medical treatment device according to an embodiment of the invention.

FIG. 40 shows a medical treatment device 100 that comprises in addition to the elements of the inspection device further a source 7 of excitation light for irradiating a mammal tissue a camera 2 to obtain a fluorescence image FI of the mammal tissue and a treatment equipment 5 to perform a medical treatment to excise or irradiate the tumor in accordance with the constructed contour or to activate a therapeutic substance in the range specified by the constructed contour.

The present invention renders it possible to more accurately identify a contour of an affected tissue, e.g. a tissue affected by a tumor, or an infected tissue. A precise knowledge of the location of the contour is of crucial importance for treatment. This is for example important for surgical removal of an affected tissue, to ascertain that no affected tissue remains after surgery, but also to ascertain that not more healthy tissue is removed than necessary. Likewise the precise knowledge of the location of the contour is crucial for applying photodynamic therapy. Therewith a therapeutic substance is locally activated within the region of the tissue that is indicated as affected. Outside the indicated region the therapeutic substance is not activated, so as to mitigate damage of healthy tissue.

In one example, the therapeutic substance may be activated to act as a chemotherapeutic agent within a region indicated as comprising a tumor. In another example the therapeutic substance may be activated to have an antimicrobial activity within a region indicated as comprising a infected tissue.

The photodynamic therapy hence involves at least the following steps. A fluorescence image is obtained in-vivo of a mammal tissue that has been rendered photosensitive with a fluorescent agent and irradiated with excitation light. The so obtained fluorescence image comprises an array of pixels having respective fluorescence signal values.

The fluorescent agent is used to visualize affected tissue, such as tumor tissue or an infected tissue. In one example the fluorescent agent is a targeted fluorescent tracer such as Cetuximab-IRDye800CW or hexvix for imaging tumor tissue and/or infection and track medicinal therapy. In another example, the fluorescent agent is an untargeted fluorescent dye such as Indocyanine green (ICG) for imaging tissue perfusion.

Exemplary agents for imaging an infected tissue are vancomycin-IRDye800CW and 1D9-IRDye800CW. Therein 1D9 is a monoclonal antibody against *Staphylococcus aureus* (including MRSA). Further examples are presented in the references included in the ANNEX.

An example of the latter application is illustrated in FIG. 41A, 41B and FIG. 42A-42F.

Figure 41A:
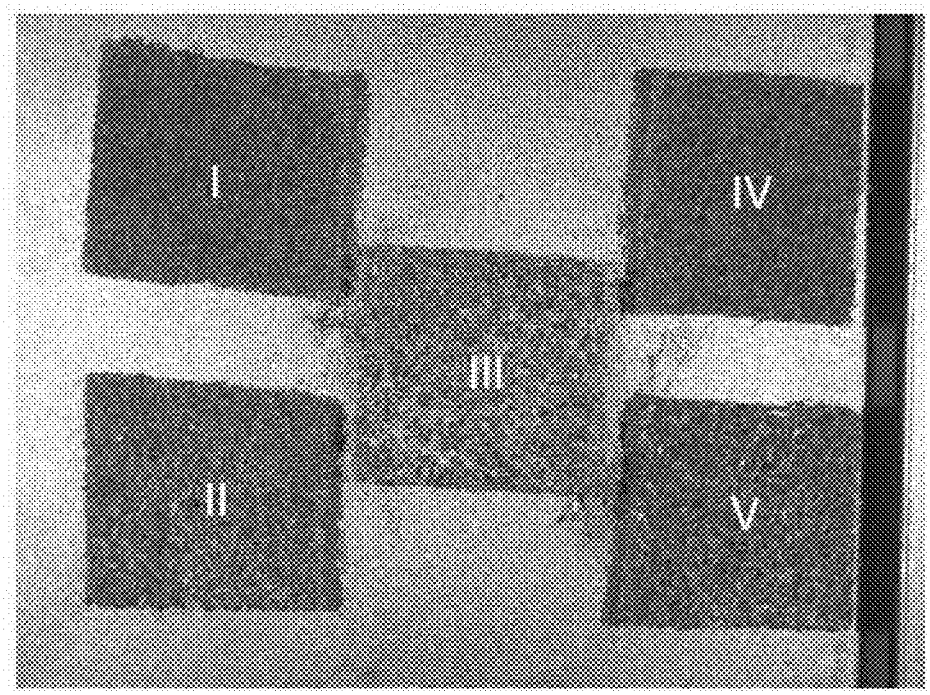
FIG. 41A, 41B respectively show a tray with samples imaged with visible light and a fluorescence image thereof.

FIG. 41A shows an image of a tray with five samples, I-V of a foam which are prepared as specified in the table below.

Figure 41B:
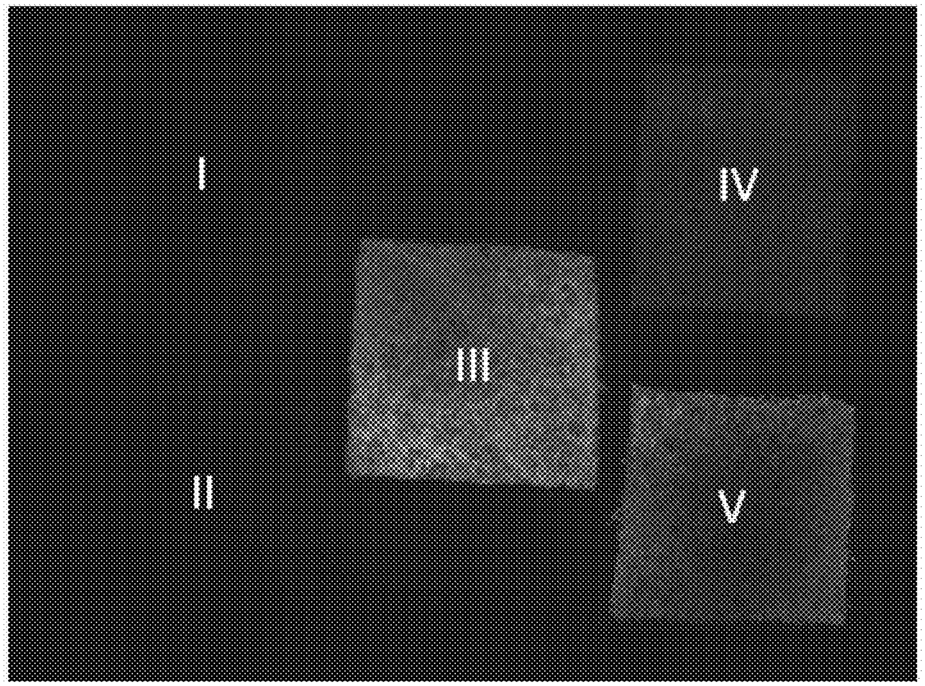

FIG. 41B shows a fluorescence image using a Pearl imaging system at a wavelength of 800 nm, obtained from the same tray with samples.

| Sample | Tracer (Y/N) | Bacteria present (Y/N) |
|---|---|---|
| I | N | N |
| II | N | Y |
| III | Y | Y: |
| IV | Y | N |
| V | Y | Y |

The first sample I is a sterile foam, wherein further no tracer is present.

The second sample, foam II has been immersed in a solution comprising a *Staphylococcus aureus* culture but not comprising a tracer.

The third sample, foam III has been immersed in a solution comprising a *Staphylococcus aureus* culture and using an amount of 10 μL of a tracer tIRDye800CW solution.

The fourth sample. Foam IV has been immersed in a sterile solution comprising the tracer tIRDye800CW.

The fifth sample, foam V has been immersed in a solution comprising a *Staphylococcus aureus* culture and an amount of 20 μL of a tracer tIRDye800CW solution.

Figure 42A:
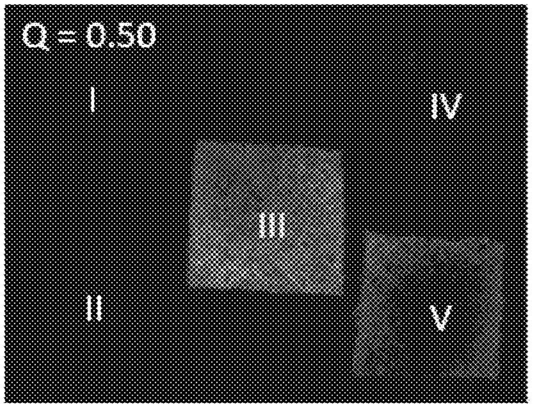
FIG. 42A-42F show segmentations of the image in FIG. 41B according to different quantiles.
Figure 42B:
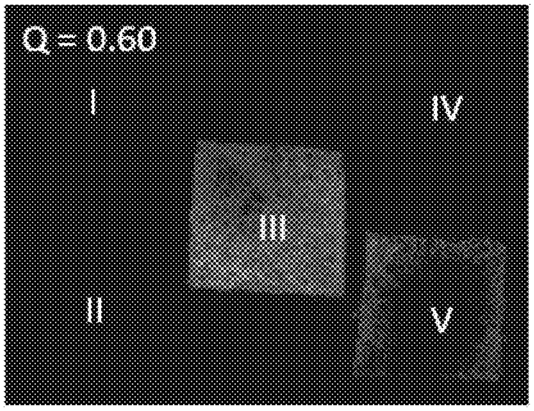
Figure 42C:
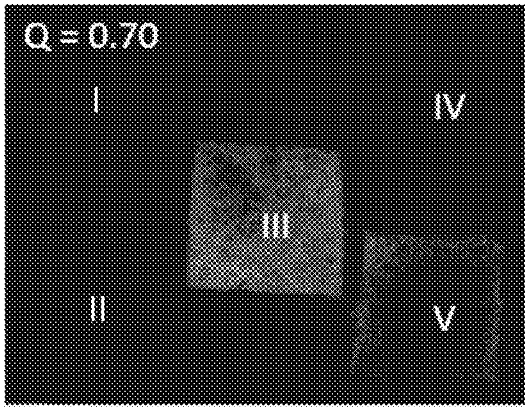
Figure 42D:
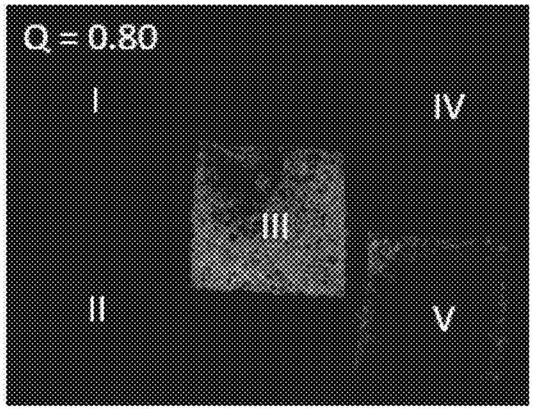
Figure 42E:
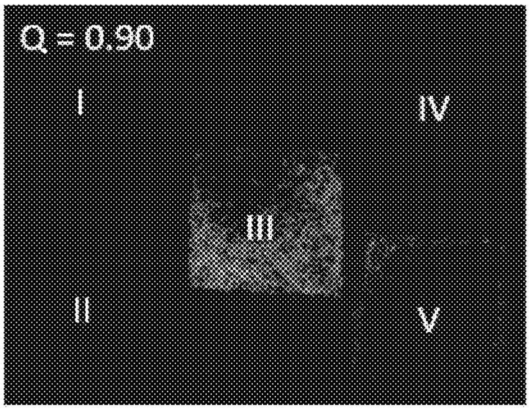
Figure 42F:
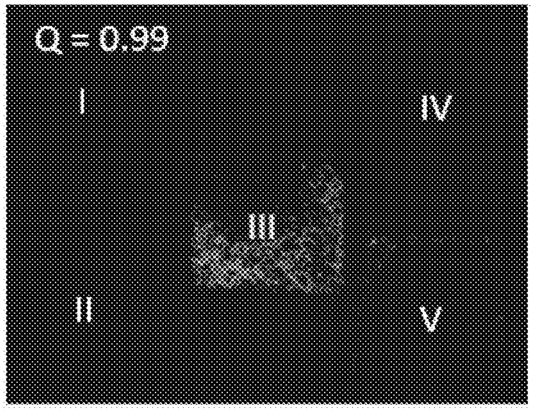

FIG. 42A-42F show segmentations of the fluorescence image of FIG. 41B according to different quartile settings Q ranging from Q=0.50 in FIG. 42A to Q=0.99 in FIG. 42F. Hence, what is shown therein are the fraction (1−Q) of pixels having a fluorescence intensity higher than the fraction Q of non-selected pixels.

According the reference value used in step S7 to determine the average fluorescence signal value $\mu_R$ and the standard deviation $\sigma_R$ is such that a fraction Q of the pixels have a fluorescence intensity less than the reference value and the fraction 1−Q has a fluorescence intensity greater than or equal to the reference value. It has been found that best results are obtained with a value Q=0.70.

As part of the present research the inventors conjectured that the fluorescent radiation observed at the border of an affected tissue, e.g. a tumorous tissue or an infected tissue, is stray radiation, i.e. fluorescent radiation that originates from the affected tissue that is scattered in the healthy tissue near the border. The inventors further conjectured that as a result, the intensity of the fluorescent radiation is expected to decline in a direction away from the border according to an exponential function i.e.

$$I(d) = I_0 e^{-\alpha \cdot d} \tag{11}$$

Wherein $I_0$ is the intensity measured at a position of the border of the affected tissue, and I(d) is the intensity at a position in the healthy tissue at a distance d from the border position, and wherein a is a constant. Based on this observations the following method is described with reference to FIG. 43A-C.

Figure 43A:
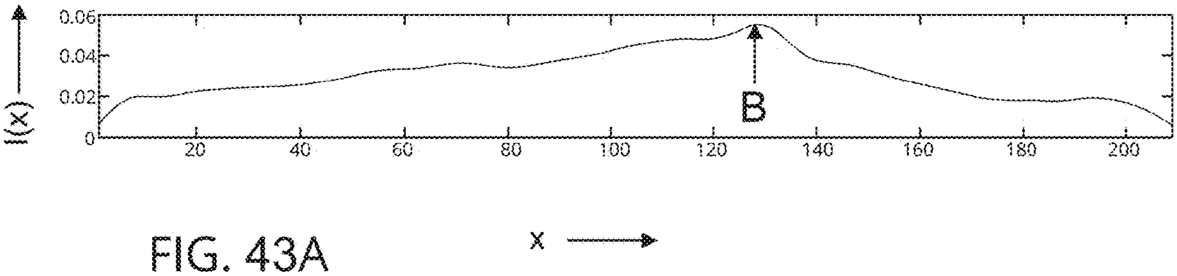
FIGS. 43A, 43B, and 43C demonstrate a further approach for detection of a border position between a normal tissue and an affected tissue.

FIG. 43A shows a measured fluorescence value I(x) as a function of a position along a scanning path in the fluorescence image. In this case the scanning path is a scan line in the x-direction of the image, but the scan-line may have any other direction. Also the scanning path may be a curved path. As shown in FIG. 43A, the scan range extends from 0 to about 210 pixels. Due to the relatively high value of the function I(x) at the position B, it is presumed that pixel having coordinate x=130 represents a portion of the affected tissue. It is now shown how a border of the affected tissue at a position left of B is determined.

Figure 43B:
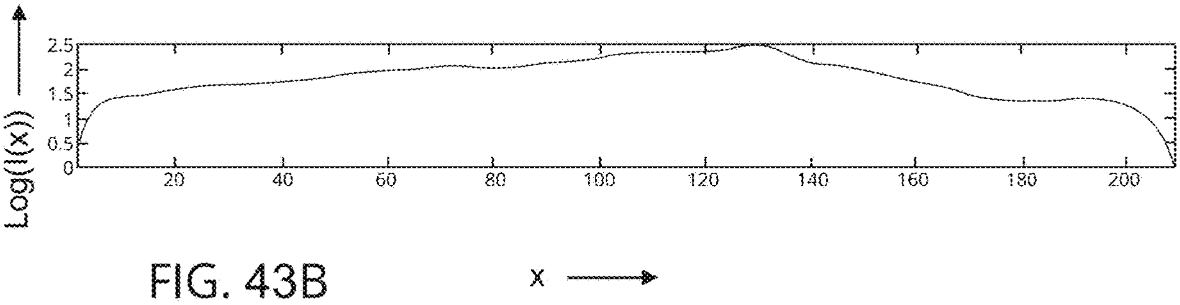

FIG. 43B shows the logarithmic value log (I(x)) of the measured fluorescence value I(x). In view of the observations above, the value log (I(x)) is expected to decline in a direction away from the border according to the function $$\log(I(d)) = -\alpha \cdot d \cdot \log(I(x0)) \tag{12}$$

Accordingly, the function log (I(x)) is expected to have linear portions for areas in the healthy tissue, near the affected tissue. To identify these areas, the linearity of the function log (I(x)) as a function of x is determined by matching the curve in a sliding window with a linear function. By way of example the sliding window has length of 30 pixels and a linear function is matched with least squares method. Also a different length may be applicable, however the length should not be too small, in order to have an adequate signal to noise ratio. Preferably the length is at least 10 pixels. In order to have a sufficiently high resolution, the length should not be too large. However, this depends on the resolution of the image ($mm \cdot pixel^{-1}$). For the present case, wherein the resolution is 85 μm, the length of the sliding window is preferably not larger than 70 pixels. However, in case the resolution is higher with a certain factor, then also the maximum length of the window can be larger with that factor. The sliding window is symmetric to avoid a bias in the Linearity function. However, it may be contemplated to use an asymmetric window instead and to compensate the bias.

Figure 43C:
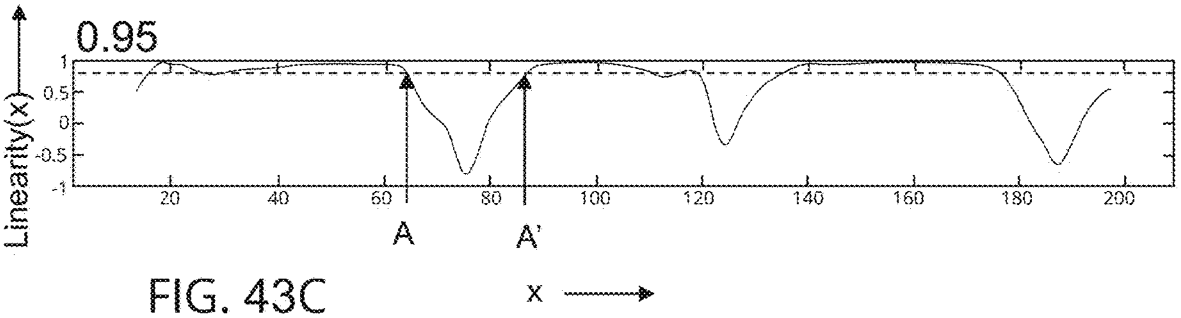

In FIG. 43C the correlation of the function log (I(x)) within the sliding window is shown as Linearity (x). Therein the value 1 indicates the extreme case that the function log (I(x)) within the sliding window is exactly linear, and the value 0 indicates that the function log (I(x)) within the sliding window maximally deviates from a linear function. It is noted that the function Linearity (x) will also approach 1 in regions wherein the intensity I(x) is constant. For practical purposes it is presumed that the function log (I(x)) is linear if the function Linear (x) is at least 0.95, as is indicated by the dashed line in FIG. 43C. In the direction of the x-axis, the function decreases below this threshold value at position A. This is considered the location where the scanline intersects the border of the affected tissue.

At this point is the transition from the region wherein the function log (I(x)) linearly increases to the region wherein the function log (I(x)) assumes a more constant value. The point A' indicates the position along the scanline where the more constant value has been achieved. Likewise a location where the affected tissue borders the health tissue at a position right of B can be determined.

The method may be repeated with different scanlines. For example in this case, wherein the scanlines extend in the direction x, the border positions can be determined for respective scanlines with different y-coordinates, to estimate the contour of the affected tissue within the healthy tissue. The method may alternatively or additionally be applied with scanlines in different directions The method as described with reference to FIG. 43A-43C can be used autonomously, but can also be used as a preprocessing step for further analyses. For example, based on the contour identified herewith it can be estimated which number of pixels in the image represents affected tissue and which number represents healthy tissue. For example, if the image of the tissue comprises an area having a size of NO pixels representing affected tissue and an area having a size of N2 pixels having healthy tissue, then the predetermined fraction used for determining the reference value IR is N2/(N0+N2). Also the method is applicable as a preprocessing step in the method described in international patent application PCT/NL2024/050047 filed by the same Applicant. Therein this preprocessing step may be used to determine a tentatively assigned position.

Alternatively the method as described with reference to FIG. 43A-43C can be used as a post-processing step to apply corrections to a segmentation result obtained with another method.

In summary, the inspection method as elucidated herewith with reference to FIG. 43A-43C comprises the following steps.

It is presumed that a fluorescence image has been captured of a mammal tissue that has been rendered photosensitive with a fluorescent agent and irradiated with excitation light, the fluorescence image (FI) comprising an array of pixels having respective fluorescence signal values.

The fluorescence image may be obtained ex-vivo so as to verify that an affected tissue has been completely removed during surgery. Alternatively the fluorescence image may be obtained in-vivo for the purpose of assisting a surgeon during operation.

The fluorescent agent is used to visualize affected tissue, such as tumor tissue or an infected tissue. Exemplary agents for imaging an infected tissue are vancomycin-IRDye800CW and 1D9-IRDye800CW. Therein 1D9 is a monoclonal antibody against *Staphylococcus aureus* (including MRSA). Further examples are presented in the references included in the ANNEX.

At least one sequence of fluorescence values I(x) is obtained from pixels along positions x of a scan path. A logarithmic value is determined of each of the values of the sequence of fluorescence values I(x). Alternatively it may be contemplated to compute the logarithmic value of all fluorescence values I(x) in the image and to subsequently obtain a sequence of logarithmic values log (I(x)) from pixels along positions x of a scan path. However it is generally preferred to first obtain the sequence of fluorescence values and to subsequently apply the logarithmic function so that the logarithmic function need not be applied to pixels that are not involved in the computation.

Then it is determined to which extent a sequence of logarithmic values log (I(x)) locally approximates a linear function.

A transition from healthy tissue to affected tissue boundary is estimated at a location where the linearity starts to decrease significantly, e.g. decreases below a threshold value, e.g. 0.95.

The scan path can be a scanline in an arbitrary direction but may alternatively be a curved path. Nevertheless a scan line or a scan path with a negligible curvature is preferred to avoid that the curvature of the path would affect the linearity of a sequence of values in the boundary regions.

ANNEX: FURTHER REFERENCES

Empowering antimicrobial photodynamic therapy of *Staphylococcus aureus* infections with potassium iodide. Bispo M, Suhani S, van Dijl J M. J Photochem Photobiol B. 2021 December; 225:112334. doi: 10.1016/j.jphotobiol.2021.112334.

Comparison of two fluorescent probes in preclinical non-invasive imaging and image-guided debridement surgery of Staphylococcal biofilm implant infections. Park H Y, Zoller S D, Hegde V, Sheppard W, Burke Z, Blumstein G, Hamad C, Sprague M, Hoang J, Smith R, Romero Pastrana F, Czupryna J, Miller L S, López-Álvarez M, Bispo M, van Oosten M, van Dijl J M, Francis K P, Bernthal N M. Sci Rep. 2021 Jan. 15; 11(1):1622. doi: 10.1038/s41598-020-78362-7.

Fighting *Staphylococcus aureus* infections with light and photoimmunoconjugates. Bispo M, Anaya-Sanchez A, Suhani S, Raineri E J M, López-Álvarez M, Heuker M, Szymański W, Romero Pastrana F, Buist G, Horswill A R, Francis K P, van Dam G M, van Oosten M, van Dijl J M. JCI Insight. 2020 Nov. 19; 5(22):e139512. doi: 10.1172/jci.insight.139512.

A Facile and Reproducible Synthesis of Near-Infrared Fluorescent Conjugates with Small Targeting Molecules for Microbial Infection Imaging. Reeßing F, Bispo M, López-Alvarez M, van Oosten M, Feringa B L, van Dijl J M, Szymański W. ACS Omega. 2020 Aug. 26; 5(35):22071-22080. doi: 10.1021/acsomega.0c02094.

Novel in vivo mouse model of shoulder implant infection. Sheppard W L, Mosich G M, Smith R A, Hamad C D, Park H Y, Zoller S D, Trikha R, McCoy T K, Borthwell R, Hoang J, Truong N, Cevallos N, Clarkson S, Hori K R, van Dijl J M, Francis K P, Petrigliano F A, Bernthal N M. J Shoulder Elbow Surg. 2020 July; 29(7):1412-1424. doi: 10.1016/j.jse.2019.10.032.

Multimodal imaging guides surgical management in a preclinical spinal implant infection model. Zoller S D, Park H Y, Olafsen T, Zamilpa C, Burke Z D, Blumstein G, Sheppard W L, Hamad C D, Hori K R, Tseng J C, Czupryna J, McMannus C, Lee J T, Bispo M, Romero Pastrana F, Raineri E J, Miller J F, Miller L S, van Dijl J M, Francis K P, Bernthal N M. JCI Insight. 2019 Feb. 7; 4(3):e124813. doi: 10.1172/jci.insight.124813.

Noninvasive optical and nuclear imaging of *Staphylococcus*-specific infection with a human monoclonal antibody-based probe. Romero Pastrana F, Thompson J M, Heuker M, Hoekstra H, Dillen C A, Ortines R V, Ashbaugh A G, Pickett J E, Linssen M D, Bernthal N M, Francis K P, Buist G, van Oosten M, van Dam G M, Thorek D L J, Miller L S, van Dijl J M. Virulence. 2018 Jan. 1; 9(1):262-272. doi: 10.1080/21505594.2017.1403004.

Real-time in vivo imaging of invasive- and biomaterial-associated bacterial infections using fluorescently labelled vancomycin. van Oosten M, Schäfer T, Gazendam J A, Ohlsen K, Tsompanidou E, de Goffau M C, Harmsen H J, Crane L M, Lim E, Francis K P, Cheung L, Olive M, Ntziachristos V, van Dijl J M, van Dam G M. Nat Commun. 2013; 4:2584. doi: 10.1038/ncomms3584.

The invention claimed is:

1. An image inspecting method to inspect a luminescence image, in particular a fluorescence image, represented as an array of pixels, $N_1$ in number, and having respective fluorescence signal values ($F_I(p)$), the method comprising a procedure for indicating in the fluorescence image a border between a target region representing an affected tissue, and a reference region outside the target region, comprising:

accessing a pre-determined fraction (f) having a range [0,1];

determining a reference value ($I_R$) such that there are said fraction (f) of the number ($N_1$) of pixels in the array having fluorescence signal values ($F_I(p)$) being smaller than a reference value ($I_R$);

computing an average background signal level ($\mu_R$) as the average value over the fluorescence signal values ($F_I$ (p)) in the array being smaller than the reference value ($I_R$);

computing a variation level as the standard deviation ($\sigma_R$) of the fluorescence signal values ($F_I$(p)) being smaller than the reference value $I_R$;

computing per pixel an excess contrast-to-noise ratio from (i) the fluorescence signal value, (ii) the average background signal level, (iii) the variation level and using an adjustable regularisation parameter, where the excess contrast-to-noise ratio represents an amount of excess of a local contrast-to-noise ratio to a statistical global contrast-to-noise ratio that is based on the global signal variations represented by fluorescence signal values compared to the reference value in relative to the standard deviation; and indicating the border by pixels having an excess contrast-to-noise ratio larger than a predetermined threshold value.

2. The image inspection method of claim 1, comprising determining per pixel that it is part of the target region if an excess contrast-to-noise ratio mCNR (p) for said pixel exceeds a predetermined threshold value ($T_{CNR}$) and determining that the pixel is part of the reference region otherwise, wherein the excess contrast-to-noise ratio mCNR (p) of a pixel is defined as $$\hat{m}CNR(p) = \frac{FI(p) - \mu_R}{c \cdot \sigma_R} \tag{1b}$$

wherein FI(p) is the fluorescence signal value of the pixel (p) and c is a regularization parameter;

identifying at least one contour of the target region.

3. The method according to claim 2, wherein the fluorescence image is further captured of a background, and wherein the method further comprises:

performing a preliminary image segmentation to distinguish in the fluorescence image a foreground region representing the mammal tissue and a background region representing the background, comprising determining per pixel that it is part of the foreground region if the fluorescence signal value significantly exceeds an average fluorescence signal value determined for the background taking into account a standard deviation of fluorescence signal values in the background and determining that the pixel is part of the background region otherwise.

4. The method according to claim 3, wherein the average fluorescence signal value and the standard deviation of fluorescence signal values are determined from a portion of the fluorescence image that is designated as representing the background.

5. The method according to claim 1, further comprising a scan trajectory based evaluation that includes:

obtaining at least one fluorescence signal value vector of fluorescence signal values in the fluorescence image along a scan trajectory;

for each threshold value of a plurality of threshold values determining a respective set of candidate scan trajectory sections in which the fluorescence signal value exceeds the threshold value and determining statistical properties of sections of the scan trajectory not being candidate scan trajectory sections; and determining for which threshold value of the plurality of threshold values the respective set of candidate scan trajectory sections best matches the image segmentation of the fluorescence image along the scan trajectory according to an excess contrast-to-noise ratio based segmentation using the determined statistical properties.

6. The method according to claim 1, further comprising for at least one contour determining at least one main axis;

obtaining at least one fluorescence signal value vector of fluorescence signal values in the fluorescence image along a scan line that is orthogonal to the main axis;

based on information of the contour at points of intersection with the scan line, selectively performing an identification of one or more sections of the scan line where an excess contrast-to-noise ratio exceeds a predetermined level, said scan line sections each comprising a respective first end point indicative for a transition from normal tissue to tumorous tissue or infected tissue and a respective second end point indicative for a transition from tumorous tissue or infected tissue to normal tissue.

7. An inspection device for inspection of a luminescence image, in particular a fluorescence image represented as an array of pixels having respective fluorescence signal values ($F_I$(p)) and configured to carry-out the method of claim 1.

8. The inspection device according to claim 7, further being configured to perform the following operations for indicating the border:

obtaining respective fluorescence signal vectors ($F_L$( . . . )) for respective scan trajectories, wherein the respective values of a respective fluorescence signal vector ($F_L$( . . . )) are an indication of a magnitude of the fluorescence signal in the fluorescence image at respective positions of the scan trajectory;

wherein the scan trajectory extends through a tissue area;

evaluating respective excess contrast-to-noise ratio vectors ($mCNR_{LM}$( . . . )) for respective fluorescence signal vectors ($F_L$( . . . )), respective values of respective excess contrast-to-noise ratio vectors ($mCNR_{LM}$( . . . ) being computed for respective positions of the scan trajectory as $$mCNR_{LM}(p) = \frac{F_L(p) - F_B - c \cdot S}{c \cdot S}, \tag{1a}$$

wherein $F_B$ is a reference fluorescence signal value being an average value of reference fluorescence signal values of the fluorescence image, S being a standard deviation of the reference fluorescence signal values and c being the regularization parameter;

wherein the image inspection device is configured to repeat the following steps for each of a plurality of positions along the scan trajectory:

tentatively assign a position from said plurality of positions along the scan trajectory as a presumed point of the border indicating the border of the target region;

compute the average of the fluorescence signal values of the fluorescence signal vector ($F_L$( . . . )), corresponding to positions of the scan trajectory at a first side of the tentatively assigned position to obtain the quantity FB0;

compute the average of the fluorescence signal values of the fluorescence signal vector (FL ( . . . )), corresponding to positions of the scan trajectory at a second side opposite the first side of the tentatively assigned position to obtain the quantity FB1;

If FB0>FB1 then it is presumed that the tumor is represented in the first side and the value FB1 represents the reference fluorescence signal value FB and the standard deviation(S) is the standard deviation of the fluorescence signal values at the second side;

If FB0<FB1 then it is presumed that the tumor is represented in the second side and the value FB0 represents the reference fluorescence signal value FB and the standard deviation(S) is the standard deviation of the fluorescence signal values at the first side;

identifying a tentatively assigned position as a candidate border position if the excess contrast-to-noise ratio vector ($mCNR_{LM}$( . . . )) has a zero-crossing at the tentatively assigned position; and indicating the border based on the set of candidate border positions obtained for the respective scan trajectories.

9. The inspection device according to claim 8, configured to indicate the border as a primary curve that interconnects peripheral ones of the transition positions.

10. The inspection device of claim 7, wherein the fluorescence image is obtained from a tissue sample taken from the subject and arranged on a background and wherein the image inspection device is configured to identify an area in the fluorescence image that represents the tissue sample as the tissue area and to identify an area in the fluorescence image of the background as the background area.

11. The inspection device of claim 7, further being configured to determine a first maximum intensity in the tissue area of the fluorescence image, to determine a second maximum intensity along a scan trajectory and to skip further processing steps for the scan trajectory if the second maximum intensity is less than a predetermined fraction of the first maximum intensity.

12. The inspection device according to claim 7, further being configured to:

determine an average fluorescence signal value ($\mu_R$) and a standard deviation ($\sigma_R$) of the fluorescence signal values comprised in the second number of fluorescent pixel values;

perform an image segmentation to distinguish in the fluorescence image a target region to denote a portion in the mammal tissue that is identified as tumorous tissue or infected tissue and a reference region to denote a remaining portion in the mammal tissue, wherein the device is configured to determine per pixel (p) that it is part of the target region if an excess contrast-to-noise ratio mCNR (p) for said pixel exceeds a predetermined threshold value ($T_{CNR}$) and to determine that the pixel is part of the reference region otherwise, wherein the excess contrast-to-noise ratio mCNR (p) of a pixel is defined as $$\tilde{m}CNR(p) = \frac{FI(p) - \mu_R}{c \cdot \sigma_R} \tag{1b}$$

wherein FI(p) is the fluorescence signal value of the pixel and c is regularization parameter; and identify a contour of the target region.

13. The inspection device according to claim 8, configured to indicate the border as a secondary curve that encloses a primary curve that interconnects the peripheral ones of the transition positions, and that extends at a distance outside the primary curve dependent on the type of tumor present in the tissue.

14. The inspection device according to claim 8, wherein the indication $F_L(p)$ of the magnitude of the fluorescence signal in the fluorescence image at the position of the scan trajectory is an average value of fluorescence signal values of pixels in the fluorescence image within a one-dimensional window comprising the position and being directed transverse to a direction of the scan trajectory.

15. The inspection device according to claim 8, further being configured to perform a low-pass filtering of the excess contrast-to-noise ratio vector.

16. An image inspecting method to inspect a luminescence image, in particular a fluorescence image, represented as an array of pixels, $N_1$ in number, and having respective fluorescence signal values ($F_I(p)$), the method comprising a procedure for indicating in the fluorescence image a border between a target region representing a tumour and a reference region outside the target region, comprising:

obtaining at least one sequence of respective logarithmic fluorescence signal values of respective subsequent pixels that are arranged along a scan trajectory within the fluorescence image, wherein the scan trajectory starts in a position identified as being part of the reference region in the fluorescence image;

computing an indicator for a local linearity of the logarithmic fluorescence signal value as a function of the position in the at least one sequence;

identifying a position in the sequence wherein the indicator indicates that the logarithmic fluorescence signal value as a function of the position in the sequence is no longer linear, the identified position being a candidate border position for the border between the normal tissue and the tumor tissue or infected tissue; and indicating the border by pixels having an excess contrast-to-noise ratio larger than a predetermined threshold value.

* * * * *